United States Patent
Bolli et al.

(10) Patent No.: US 9,303,023 B2
(45) Date of Patent: Apr. 5, 2016

(54) PYRAZOLE AND IMIDAZOLE DERIVATIVES USEFUL AS OREXIN ANTAGONISTS

(75) Inventors: Martin Bolli, Allschwil (CH); Christoph Boss, Allschwil (CH); Christine Brotschi, Allschwil (CH); Markus Gude, Allschwil (CH); Bibia Heidmann, Allschwil (CH); Thierry Sifferlen, Allschwil (CH); Jodi T. Williams, Allschwil (CH)

(73) Assignee: ACTELION PHARMACEUTICALS LTD., Allschwill (CH)

( * ) Notice: Subject to any disclaimer, the term of this patent is extended or adjusted under 35 U.S.C. 154(b) by 90 days.

(21) Appl. No.: 14/000,172

(22) PCT Filed: Feb. 17, 2012

(86) PCT No.: PCT/IB2012/050733
§ 371 (c)(1), (2), (4) Date: Aug. 16, 2013

(87) PCT Pub. No.: WO2012/110986
PCT Pub. Date: Aug. 23, 2012

(65) Prior Publication Data
US 2013/0324579 A1    Dec. 5, 2013

(30) Foreign Application Priority Data

Feb. 18, 2011    (WO) .............. 2011/050680

(51) Int. Cl.
| | | |
|---|---|---|
| C07D 413/12 | (2006.01) | |
| C07D 413/14 | (2006.01) | |
| C07D 417/12 | (2006.01) | |
| C07D 417/14 | (2006.01) | |
| A61K 31/4155 | (2006.01) | |
| A61K 31/4178 | (2006.01) | |
| A61K 31/422 | (2006.01) | |
| A61P 25/28 | (2006.01) | |
| A61P 25/22 | (2006.01) | |
| A61P 25/20 | (2006.01) | |

(52) U.S. Cl.
CPC .......... *C07D 413/12* (2013.01); *A61K 31/4155* (2013.01); *A61K 31/4178* (2013.01); *A61K 31/422* (2013.01); *C07D 413/14* (2013.01); *C07D 417/12* (2013.01); *C07D 417/14* (2013.01)

(58) Field of Classification Search
CPC ... C07D 413/12; C07D 413/14; C07D 417/14
See application file for complete search history.

(56) References Cited

U.S. PATENT DOCUMENTS

| | | |
|---|---|---|
| 7,763,638 B2 | 7/2010 | Aissaoui et al. |
| 8,063,099 B2 | 11/2011 | Aissaoui et al. |
| 8,288,419 B2 | 10/2012 | Bur et al. |
| 2009/0082394 A1 | 3/2009 | Jenck |
| 2010/0234420 A1 | 9/2010 | Jenck |
| 2011/0105491 A1 | 5/2011 | Aissaoui et al. |
| 2011/0212968 A1 | 9/2011 | Aissaoui et al. |

FOREIGN PATENT DOCUMENTS

| | | |
|---|---|---|
| EP | 2 402 322 A1 | 1/2012 |
| WO | WO 2005/060959 A1 | 7/2005 |
| WO | WO 2005/118548 A1 | 12/2005 |
| WO | WO 2006/110626 A1 | 10/2006 |
| WO | WO 2007/061763 A2 | 5/2007 |
| WO | WO 2007/105177 A1 | 9/2007 |
| WO | WO 2009/014674 A1 | 1/2009 |
| WO | WO 2009/016560 A2 | 2/2009 |
| WO | WO 2009/047723 A2 | 4/2009 |
| WO | WO 2009/077954 A1 | 6/2009 |
| WO | WO 2010/004507 A1 | 1/2010 |
| WO | WO 2010/038200 A1 | 4/2010 |
| WO | WO 2010/044054 A1 | 4/2010 |
| WO | WO 2010/051236 | 5/2010 |

OTHER PUBLICATIONS

Borgland, S.L., et al., "Orexin A in the VTA is Critical for the Induction of Synaptic Plasticity and Behavioral Sensitization to Cocaine", Neuron., vol. 49, pp. 589-601, (Feb. 16, 2006).
Chemelli, R.M., et al., "Narcolepsy in Orexin Knockout Mice: Molecular Genetics of Sleep Regulation", Cell, vol. 98, pp. 437-451, (Aug. 20, 1999).
Eicher, T., et al., "The Chemistry of Heterocycles: Structure, Reactions, Synthesis and Applications", 2nd Edition, 2003, Wiley, ISBN 978-3-527-30720-3 (Table of Contents Only).
Gould, P.L., "Salt Selection for Basic Drugs", International Journal of Pharmaceutics, vol. 33, pp. 201-217, (1986).
Jeanty, M., et al. "Synthesis of 4-and 6-Azaindoles via the Fischer Reaction", Organic Letters, (2009), vol. 11, No. 22, pp. 5142-5145, (Article states, "Published on web Oct. 19, 2009", contents of which have not been verified by the undersigned).

(Continued)

*Primary Examiner* — Susanna Moore
(74) *Attorney, Agent, or Firm* — Hoxie & Associates, LLC

(57) ABSTRACT

The present invention relates to pyrazole and imidazole derivatives of formula (I)

Formula (I)

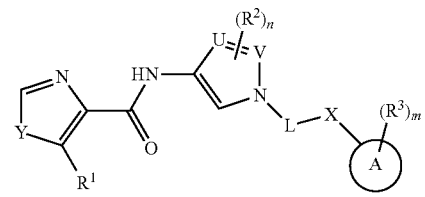

wherein U, V, L, X, Y, $R^1$, $(R^2)_n$ and $(R^3)_m$ and ring A are as described in the description, to their preparation, to pharmaceutically acceptable salts thereof, and to their use as pharmaceuticals, to pharmaceutical compositions containing one or more compounds of formula (I), and especially to their use as orexin receptor antagonists.

12 Claims, No Drawings

(56) References Cited

OTHER PUBLICATIONS

Jenck, F., et al., "Promotion of Sleep by Targeting the Orexin System in Rats, Dogs and Humans", Nature Medicine (Advanced Online Publication), published online Jan. 28, 2007, doi:10.1038/nm1544.

Kang, J.E., et al., "Amyloid-β Dynamics Are Regulated by Orexin and the Sleep-Wake Cycle", Sciencexpress, www.scienceexpress.org, Sep. 24, 2009, doi:10.1126/science.1180962, pp. 1-8.

Katrizky, C.W., et al., "Comprehensive Heterocyclic Chemistry II", (1996), Elsevier, ISBN 0-08-042072-9 (Book Information for vols. 1-11), http://www.elsevier.com/wps/find/bookdescription.cws_home/30116/ . . . .

Nollet, M., et al., "Activation of Orexin Neurons in Dorsomedial/Perifornical Hypothalamus and Antidepressant Reversal in a Rodent Model of Depression", Neuropharmacology, doi:10.1016/j.neuropharm.2011.04.022, (2011), pp. 1-11.

Prud'Homme, M.J., et al., "Nutritional Status Modulates Behavioural and Olfactory Bulb Fos Responses to Isoamyl Acetate or Food Odour in Rats: Roles of Orexins and Leptin", Neuroscience, vol. 162, pp. 1287-1298, (2009).

Remington, "The Science and Practice of Pharmacy, 21st Edition (2005), Part 5, Pharmaceutical Manufacturing" [published by Lippincott Williams & Wilkins], (Table of Contents Only).

Sakurai, T., et al., "Orexins and Orexin Receptors: A Family of Hypothalamic Neuropeptides and G Protein-Coupled Receptors that Regulate Feeding Behavior", Cell, vol. 92, pp. 573-585, (Feb. 20, 1998).

Shimada, I., et al., "Synthesis and Structure-Activity Relationships of a Series of Substituted 2-(1H-furo[2,3-g]indazol-1-yl)ethylamine Derivatives as 5-HT$_{2C}$ Receptor Agonists", Bioorganic & Medicinal Chemistry, vol. 16, pp. 1966-1982, (2008), (Article states, "Available online Nov. 4, 2007", contents of which have not been verified by the undersigned).

International Search Report for International Application PCT/IB2012/050733 with mailing date of Apr. 25, 2012.

Written Opinion for International Application PCT/IB2012/050733 issued on Aug. 21, 2013.

PYRAZOLE AND IMIDAZOLE DERIVATIVES USEFUL AS OREXIN ANTAGONISTS

CROSS REFERENCE TO RELATED APPLICATIONS

This application is a United States Application under 35 U.S.C. 371 claiming benefit of PCT Application No. PCT/IB2012/050733, filed on Feb. 17, 2012, which claims the benefit of PCT Application No. PCT/IB2011/050680, filed on Feb. 18, 2011, the contents of each of which are incorporated herein by reference.

The present invention relates to novel pyrazole and imidazole derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451). Furthermore, in vitro and in vivo evidence for a critical role of orexin signaling in the ventral tegmental area in neural plasticity relevant to addiction has been published (S. L. Borgland et al. Neuron, 2006, 49, 589-601).

Thus, orexin receptors may have numerous implications in pathologies as known from the literature, such as dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions. The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548) advanced to clinical development for primary insomnia. In the rat, the compound has been shown for example to decrease alertness, characterized by decreases in both active wake and locomotion; and to dose-dependently increase the time spent in both REM and NREM sleep (F. Jenck et al., Nature Medicine 2007, 13, 150-155). The compound has also been shown to enhance memory function in a rat model (WO2007/105177). The compound furthermore decreased brain levels of amyloid-beta (Aβ) as well as Aβ plaque deposition after acute sleep restriction in amyloid precursor protein transgenic mice [J E Kang et al., "Amyloid-beta dynamics are regulated by orexin and the sleep-wake cycle.", Science 2009, 326(5955): 1005-1007]. The accumulation of the Aβ in the brain extracellular space is hypothesized to be a critical event in the pathogenesis of Alzheimer's disease. The so-called and generally known "amyloid cascade hypothesis" links Aβ to Alzheimer's disease and, thus, to the cognitive dysfunction, expressed as impairment of learning and memory. The compound is also active in an animal model of conditioned fear: the rat fear-potentiated startle paradigm (WO2009/0047723) which relates to emotional states of fear and anxiety diseases such as anxieties including phobias and post traumatic stress disorders (PTSDs). The compound has, in addition, been shown to induce antidepressant-like activity in a mouse model of depression, when administered chronically [Nollet et al., NeuroPharm 2011, 61(1-2):336-46]; and to attenuate the natural activation induced by orexin A in fasted hungry rats exposed to food odors [M J Prud'homme et al., "Nutritional status modulates behavioural and olfactory bulb Fos responses to isoamyl acetate or food odour in rats: roles of orexins and leptin." Neuroscience 2009, 162(4), 1287-1298].

The compound (R)-2-[(S)-1-(3,4-Dimethoxy-benzyl)-6,7-dimethoxy-3,4-dihydro-1H-isoquinolin-2-yl]-N-isopropyl-2-phenyl-acetamide has been shown to be active in the rat fear-potentiated startle paradigm; and in an animal model related to addictions [EP 2402322].

The present invention provides novel pyrazole and imidazole derivatives, which are non-peptide antagonists of human orexin receptors. These compounds are in particular of potential use in the treatment of diseases related to the orexin system, especially comprising all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

1) A first aspect of the invention relates to compounds of the formula (I)

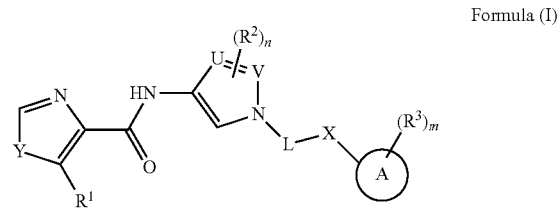

Formula (I)

wherein $R^1$ represents aryl or 5- to 10-membered heteroaryl (notably phenyl or 5- or 6-membered heteroaryl), wherein the aryl or 5- to 10-membered heteroaryl independently is unsubstituted, or mono-, di-, or tri-substituted; wherein the substituents are independently selected from the group consisting of:
- $(C_{1-4})$alkyl, $(C_{1-4})$alkoxy, halogen, cyano, $(C_{1-3})$fluoroalkyl, $(C_{1-3})$fluoroalkoxy; and
- —$NR^4R^5$, wherein $R^4$ and $R^5$ are independently hydrogen or $(C_{1-4})$alkyl; or $R^4$ and $R^5$ together with the nitrogen atom to which they are attached to form a saturated 5- to 7-membered ring optionally containing an oxygen atom; and phenyl or 5- or 6-membered heteroaryl, wherein the phenyl or 5- or 6-membered heteroaryl independently is unsubstituted, or mono-, or di-substituted; wherein the substituents are independently selected from the group consisting of $(C_{1-4})$alkyl, $(C_{1-4})$alkoxy, halogen, cyano, $(C_{1-3})$fluoroalkyl, $(C_{1-3})$fluoroalkoxy;
wherein at maximum one substituent selected from —$NR^4R^5$ and phenyl or 5- or 6-membered heteroaryl is present;

U represents CH, and V represents N; or U represents N and V represents CH;

$(R^2)_n$ represents one or two optional substituents (i.e. n represents the integer 0, 1, or 2), wherein each $R^2$ independently is $(C_{1-3})$alkyl; and Y represents O or S; and ring A represents aryl or 5- to 10-membered heteroaryl, wherein said aryl or 5- to 10-membered heteroaryl independently is optionally substituted with $(R^3)_m$; wherein $(R^3)_m$ represents one, two or three optional substituents (i.e. m represents the integer 0, 1, 2, or 3), wherein each $R^3$ independently is selected from the group consisting of:

$(C_{1-4})$alkyl, $(C_{1-4})$alkoxy, halogen, cyano, $(C_{1-3})$fluoroalkyl, $(C_{1-3})$fluoroalkoxy; and phenyl or 5- or 6-membered heteroaryl, wherein the phenyl or 5- or 6-membered heteroaryl independently is unsubstituted, or mono-, or di-substituted; wherein the substituents are independently selected from the group consisting of $(C_{1-4})$alkyl, $(C_{1-4})$alkoxy, halogen, cyano, $(C_{1-3})$fluoroalkyl, $(C_{1-3})$fluoroalkoxy;

wherein at maximum one phenyl or 5- or 6-membered heteroaryl substituent is present;

or $(R^3)_m$ represents two substituents which form a non-aromatic 5- or 6-membered ring fused to ring A, wherein said 5- or 6-membered ring optionally contains one or two oxygen atoms;

L represents a group —$(CH_2)_m$—, wherein m represents the integer 2 or 3; wherein said group L is optionally substituted (preferably at the carbon atom which is adjacent to X) with $R^6$; wherein $R^6$, if present, represents $(C_{1-3})$alkyl; and X represents a direct bond, O, S or $NR^7$ (notably a direct bond, O or $NR^7$);

wherein, in case X represents $NR^7$, $R^7$ represents hydrogen or $(C_{1-3})$alkyl; or, additionally, $R^7$ and $R^6$ may form a 5- to 7-membered saturated ring including the nitrogen to which $R^7$ is attached to; or $R^7$ together with one of the substituents $R^3$ may form a non-aromatic 5- to 7-membered ring including the nitrogen to which $R^7$ is attached to, which ring is fused to ring A; wherein $R^6$ is absent; and the remaining of said substituents $R^3$, if present, independently are selected from the group consisting of $(C_{1-4})$alkyl, $(C_{1-4})$alkoxy, halogen, cyano, $(C_{1-3})$fluoroalkyl, and $(C_{1-3})$fluoroalkoxy.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

The present invention also includes isotopically labelled, especially $^2H$ (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2H$ (deuterium) labelled compounds of formula (I) and salts thereof are within the scope of the present invention. Substitution of hydrogen with the heavier isotope $^2H$ (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Where the plural form is used for compounds, salts, pharmaceutical compositions, diseases and the like, this is intended to mean also a single compound, salt, or the like.

Any reference to compounds of formula (I) is to be understood as referring also to the salts (and especially the pharmaceutically acceptable salts) of such compounds, as appropriate and expedient.

The term "pharmaceutically acceptable salts" refers to non-toxic, inorg. or organic acid and/or base addition salts. Reference can be made to "Salt selection for basic drugs", *Int. J. Pharm.* (1986), 33, 201-217.

The term "halogen" means fluorine, chlorine, or bromine, preferably fluorine or chlorine.

The term "alkyl", used alone or in combination, refers to a saturated straight or branched chain alkyl group containing one to six carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl.

The term "cycloalkyl", used alone or in combination, refers to a saturated cyclic alkyl group containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl and cyclohexyl. Preferred is cyclopropyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$ fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a ($C_{1-3}$)fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are ($C_1$)fluoroalkoxy groups such as trifluoromethoxy and difluoromethoxy.

Examples of rings where "$R^4$ and $R^5$ together with the nitrogen atom to which they are attached to form a saturated 5- to 7-membered ring optionally containing an oxygen atom" are notably a pyrrolidine, a piperidine, a morpholine, or (less preferred) an azepane ring.

Examples of rings where "$R^7$ and $R^6$ form a 5- to 7-membered saturated ring including the nitrogen to which $R^7$ is attached to" are notably a pyrrolidine, or a piperidine, or an azepane ring.

The term "aryl", alone or in combination, means notably a phenyl, or a naphthyl group. The aryl group may be unsubstituted or substituted as explicitly defined.

For the substituent $R^1$ aryl represents notably phenyl. Examples of aryl groups as used for substituent $R^1$ are phenyl, 3-chlorophenyl, 3-fluorophenyl, 2-fluorophenyl, 3-cyanophenyl, 3-methylphenyl, 3,4-dimethylphenyl, 4-methoxyphenyl, 3-methoxy-4-methylphenyl, 3-dimethylamino-phenyl, 4-trifluoromethylphenyl, 3-trifluoromethylphenyl, 3-trifluoromethoxyphenyl, 3-pyrrolidin-1-yl-phenyl, 3-morpholin-4-yl-phenyl, and biphenyl-3-yl.

For ring A aryl represents notably phenyl. Examples of aryl groups as used for ring A are phenyl, 4-fluorophenyl, 3-fluorophenyl, and 3-methoxyphenyl.

For the particular sub-group of aryl groups wherein "$R^7$ together with one of the substituents $R^3$ may form a non-aromatic 5- to 7-membered ring including the nitrogen to which $R^7$ is attached to, which ring is fused to ring A" said fused non-aromatic 5- to 7-membered ring is notably a fused pyrrolidine, or a fused piperidine ring. An example of such group (including ring A) is 2,3-dihydro-indol-1-yl.

For the particular sub-group of aryl groups wherein "$(R^3)_m$ represents two substituents which form a non-aromatic 5- or 6-membered ring fused to ring A, wherein said 5- or 6-membered ring optionally contains one or two oxygen atoms" the aryl is preferably phenyl. Examples of such aryl groups fused to a non-aromatic 5- or 6-membered ring are indanyl, tetrahydronaphthyl, 2,3-dihydrobenzofuranyl, chromanyl, chromenyl, benzo[1,3]dioxolyl, 2,3-dihydro-benzo[1,4]dioxinyl, and benzo[b][1,4]dioxinyl. Particular examples of fragments forming a non-aromatic 5- or 6-membered ring fused to said aryl are selected from the group consisting of —$(CH_2)_n$—, wherein n represents the integer 3 or 4; —$(CH_2)_p$—O—, wherein p represents the integer 1 or 2; —CH=CH—$CH_2$—O—; —O—$(CH_2)_q$—O—, wherein q represents the integer 1 or 2; and —O—CH=CH—O—. Particular examples of aryl groups carrying such substituents forming a non-aromatic 5- or 6-membered ring fused to ring A are benzo[1,3]dioxol-5-yl, and 2,3-dihydro-benzo[1,4]dioxinyl (especially benzo[1,3]dioxol-5-yl).

The term "heteroaryl", if not explicitly stated otherwise, means a 5- to 10-membered monocyclic, or bicyclic, aromatic ring containing 1 to a maximum of 4 (notably 1 to a maximum of 3) heteroatoms independently selected from oxygen, nitrogen and sulfur. Examples of such heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, and triazolyl; 6-membered monocyclic heteroaryl such as pyridyl, pyrimidyl, pyridazinyl, and pyrazinyl; and bicyclic 8- to 10-membered heteroaryl such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, pyrrolo[3,2-d]pyrimidinyl, pyrrolo[2,3-d]pyrimidinyl, 4H-furo[3,2-b]pyrrolyl, pyrrolo[2,1-b]thiazolyl, imidazo[2,1-b]thiazolyl and purinyl.

In a sub-embodiment, certain heteroaryl groups may be attached to the rest of the molecule at a (nucleophilic) nitrogen atom that is part of the heteroaryl ring. Examples of such groups are the 5-membered heteroaryl groups pyrrol-1-yl, imidazol-1-yl, pyrazol-1-yl, and triazol-1-yl; and the bicyclic 8- or 9-membered heteroaryl groups indol-1-yl, isoindol-2-yl, indazol-1-yl, benzimidazol-1-yl, benzotriazol-1-yl, 1H-pyrrolo[3,2-b]pyridin-1-yl, 1H-pyrrolo[2,3-b]pyridin-1-yl, 1H-pyrrolo[3,2-c]pyridin-1-yl, 1H-pyrrolo[2,3-c]pyridin-1-yl, 7H-pyrrolo[2,3-d]pyrimidin-7-yl, 5H-pyrrolo[3,2-d]pyrimidin-5-yl, 4H-furo[3,2-b]pyrrol-4-yl, 7H-purin-7-yl, and 9H-purin-9-yl. Notably the above-mentioned bicyclic groups (and especially the groups indol-1-yl, benzimidazol-1-yl, 1H-pyrrolo[3,2-b]pyridin-1-yl, 1H-pyrrolo[2,3-b]pyridin-1-yl, 1H-pyrrolo[3,2-c]pyridin-1-yl, 1H-pyrrolo[2,3-c]pyridin-1-yl, 7H-pyrrolo[2,3-d]pyrimidin-7-yl, purin-7-yl, and 9H-purin-9-yl) form are a particular subgroup of heteroaryl for ring A in case X represents a direct bond.

In another sub-embodiment heteroaryl groups may be attached to the rest of the molecule at a carbon atom that is part of the heteroaryl ring. For example the 6-membered heteroaryl groups, notably pyrimidin-2-yl, and (especially) the bicyclic 8- to 10-membered heteroaryl groups, notably indol-3-yl, and 1H-pyrrolo[3,2-b]pyridin-3-yl form a further particular subgroup of heteroaryl for ring A in case X represents a direct bond.

In another sub-embodiment, certain heteroaryl groups may be attached to the rest of the molecule at a carbon atom which is in alpha position to at least one (preferably two) heteroatom(s) (especially N, or O) that is/are part of the heteroaryl. Examples of such groups are the 5-membered heteroaryl groups oxazol-2-yl, thiazol-2-yl, imidazol-2-yl, and pyrazol-3-yl; the 6-membered heteroaryl groups pyridin-2-yl, pyrimid-2-yl, pyrimid-4-yl, pyridazin-3-yl, and pyrazin-2-yl; and the bicyclic heteroaryl groups benzimidazol-2-yl, benzoxazol-2-yl, benzothiazol-2-yl, quinolin-2-yl, quinazolin-2-yl, and quinoxalin-2-yl. Notably the above-mentioned 6-membered groups and 9- or 10-membered bicyclic groups (and especially the groups pyridin-2-yl, pyrimid-2-yl, pyrimid-4-yl, pyrazin-2-yl, benzimidazol-2-yl, benzoxazol-2-yl, quinolin-2-yl, quinazolin-2-yl, and quinoxalin-2-yl) form a particular subgroup of heteroaryl for ring A in case X represents O, S, or $NR^7$.

Examples of heteroaryl groups as used for the substituent $R^1$ are furanyl, oxazolyl, isoxazolyl (especially isoxazol-3-yl, 3-methyl-isoxazol-5-yl), oxadiazolyl, thienyl, thiazolyl, isothiazolyl, thiadiazolyl, pyrrolyl, imidazolyl, pyrazolyl, triazolyl, pyridyl (especially 6-methoxy-pyridin-3-yl), pyrimidyl (especially pyrimidin-4-yl), pyridazinyl, and pyrazinyl.

The heteroaryl groups as mentioned above may be unsubstituted or substituted as explicitly defined.

For the particular sub-group of heteroaryl groups wherein "$(R^3)_m$ represents two substituents which form a non-aromatic 5- or 6-membered ring fused to ring A, wherein said 5- or 6-membered ring optionally contains one or two oxygen atoms" the heteroaryl is preferably 6-membered heteroaryl ring. Examples of such heteroaryl groups fused to a non-aromatic 5- or 6-membered ring are 2,3-dihydro-[1,4]dioxino-pyridinyl groups (such as especially 2,3-dihydro-[1,4]dioxino[2,3-b]pyridinyl or 2,3-dihydro-[1,4]dioxino[2,3-c]pyridinyl), and [1,3]dioxolopyridinyl groups (such as especially [1,3]dioxolo[4,5-b]pyridinyl or [1,3]dioxolo[4,5-c]pyridinyl). Particular examples of fragments forming a non-aromatic 5- or 6-membered ring fused to said heteroaryl are selected from the group consisting of —(CH$_2$)$_n$—, wherein n represents the integer 3 or 4; —(CH$_2$)$_p$—O—, wherein p represents the integer 1 or 2; and —O—(CH$_2$)$_q$—O—, wherein q represents the integer 1 or 2.

Further embodiments of the invention are presented hereinafter:

2) A further embodiment relates to compounds according to embodiment 1), wherein R$^1$ represents phenyl or 5- or 6-membered heteroaryl, wherein the phenyl or 5- or 6-membered heteroaryl independently is unsubstituted, or mono-, or di-substituted; wherein the substituents are independently selected from the group consisting of:
- (C$_{1-4}$)alkyl, (C$_{1-4}$)alkoxy, halogen, cyano, (C$_{1-3}$)fluoroalkyl, (C$_{1-3}$)fluoroalkoxy; and
- —NR$^4$R$^5$, wherein R$^4$ and R$^5$ are independently (C$_{1-4}$)alkyl; or R$^4$ and R$^5$ together with the nitrogen atom to which they are attached to form a saturated 5- to 7-membered ring optionally containing an oxygen atom; and phenyl;
- wherein at maximum one substituent selected from —NR$^4$R$^5$ and phenyl is present.

3) A further embodiment relates to compounds according to embodiment 1), wherein R$^1$ represents phenyl or 5- or 6-membered heteroaryl, wherein the phenyl or 5- or 6-membered heteroaryl independently is unsubstituted, or mono-, or di-substituted; wherein the substituents are independently selected from the group consisting of:
- (C$_{1-4}$)alkyl, (C$_{1-4}$)alkoxy, halogen, cyano, (C$_{1-3}$)fluoroalkyl, (C$_{1-3}$)fluoroalkoxy; and
- —NR$^4$R$^5$, wherein R$^4$ and R$^5$ are independently (C$_{1-4}$)alkyl; or R$^4$ and R$^5$ together with the nitrogen atom to which they are attached to form a saturated 5- or 6-membered ring optionally containing an oxygen atom;
- wherein at maximum one —NR$^4$R$^5$ substituent is present.

4) A further embodiment relates to compounds according to embodiment 1), wherein R$^1$ represents phenyl or 5- or 6-membered heteroaryl, wherein the phenyl or 5- or 6-membered heteroaryl independently is unsubstituted, or mono-, or di-substituted; wherein the substituents are independently selected from the group consisting of:
- (C$_{1-4}$)alkyl, (C$_{1-4}$)alkoxy, halogen, cyano, (C$_{1-3}$)fluoroalkyl, and (C$_{1-3}$)fluoroalkoxy.

5) A further embodiment relates to compounds according to embodiment 1), wherein R$^1$ represents phenyl which is unsubstituted, or mono-, or di-substituted; wherein the substituents are independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$)alkyl, (C$_{1-4}$)alkoxy, and halogen).

6) A further embodiment relates to compounds according to any one of embodiments 1) to 5), wherein U represents CH, and V represents N.

7) A further embodiment relates to compounds according to any one of embodiments 1) to 5), wherein U represents N and V represents CH.

8) A further embodiment relates to compounds according to any one of embodiments 1) to 7), wherein (R$^2$)$_n$ is absent (i.e. n is 0) or (R$^2$)$_n$ represents two substituents methyl substituents.

9) A further embodiment relates to compounds according to any one of embodiments 1) to 8), wherein Y represents O.

10) A further embodiment relates to compounds according to any one of embodiments 1) to 8), wherein Y represents S.

11) A further embodiment relates to compounds according to any one of embodiments 1) to 10), wherein L represents a group —(CH$_2$)$_m$—, wherein m represents the integer 2 or 3; wherein, in case m represents the integer 2, said group L is optionally substituted at the carbon atom which is adjacent to X with R$^6$; wherein R$^6$, if present, represents methyl; or, in case X represents NR$^7$, R$^7$ and R$^6$ additionally may form a piperidine or (notably) a pyrrolidine ring including the nitrogen to which R$^7$ is attached to.

12) A further embodiment relates to compounds according to any one of embodiments 1) to 10), wherein L represents a group —(CH$_2$)$_m$—, wherein m represents the integer 2 or 3.

13) A further embodiment relates to compounds according to any one of embodiments 1) to 12), wherein ring A represents aryl or 5- to 10-membered heteroaryl, wherein said aryl or 5- to 10-membered heteroaryl independently is optionally substituted with (R$^3$)$_m$; wherein
- (R$^3$)$_m$ represents one, two or three optional substituents (i.e. m represents the integer 0, 1, 2, or 3), wherein each R$^3$ independently is selected from the group consisting of:
  - (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$)alkyl, (C$_{1-4}$)alkoxy, halogen); and
  - phenyl;
- wherein at maximum one phenyl substituent is present;
- or (R$^3$)$_m$ represents two substituents which form a fragment —O—(CH$_2$)$_q$—O—, wherein q represents the integer 1 or 2 (especially 1);
- or, in case X represents NR$^7$, (R$^3$)$_m$ additionally may represent one substituent, wherein R$^7$ together with said substituent R$^3$ forms a non-aromatic 5- to 7-membered ring including the nitrogen to which R$^7$ is attached to, which ring is fused to ring A.

14) A further embodiment relates to compounds according to any one of embodiments 1) to 12), wherein
ring A represents 6- to 10-membered heteroaryl, wherein said 6- to 10-membered heteroaryl is optionally substituted with (R$^3$)$_m$; wherein
- (R$^3$)$_m$ represents one, two or three optional substituents (i.e. m represents the integer 0, 1, 2, or 3; especially m is 0 or 1), wherein each R$^3$ independently is selected from the group consisting of:
  - (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$) alkyl, (C$_{1-4}$)alkoxy, and halogen);
- or ring A represents phenyl, wherein said phenyl is optionally substituted with (R$^3$)$_m$; wherein
- (R$^3$)$_m$ represents one, two or three optional substituents (i.e. m represents the integer 0, 1, 2, or 3; especially m is 0 or 1), wherein each R$^3$ independently is selected from the group consisting of:
  - (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$) alkoxy, and halogen);
- or (R$^3$)$_m$ represents two substituents which form a fragment —O—(CH$_2$)$_q$—O—, wherein q represents the integer 1 or 2 (especially 1);
- or, in case X represents NR$^7$, (R$^3$)$_m$ additionally may represent one substituent, wherein R$^7$ together with said substituent R$^3$ forms a non-aromatic 5- to 7-membered ring including the nitrogen to which R$^7$ is attached to, which ring is fused to ring A.

15) A further embodiment relates to compounds according to any one of embodiments 1) to 12), wherein ring A represents 6- to 10-membered heteroaryl, wherein said 6- to 10-membered heteroaryl is optionally substituted with $(R^3)_m$; wherein $(R^3)_m$ represents one, two or three optional substituents (i.e. m represents the integer 0, 1, 2, or 3; especially m is 0 or 1), wherein each $R^3$ independently is selected from the group consisting of:

$(C_{1-4})$alkyl, $(C_{1-4})$alkoxy, halogen, cyano, $(C_{1-3})$fluoroalkyl, and $(C_{1-3})$fluoroalkoxy (especially $(C_{1-4})$alkyl, $(C_{1-4})$alkoxy, and halogen).

16) A further embodiment relates to compounds according to any one of embodiments 1) to 15), wherein X represents a direct bond, O or $NR^7$.

17) A further embodiment relates to compounds according to any one of embodiments 1) to 15), wherein X represents O or $NR^7$.

18) A further embodiment relates to compounds according to any one of embodiments 1) to 15), wherein X represents $NR^7$.

19) A further embodiment relates to compounds according to any one of embodiments 1) to 15), wherein X represents O.

20) A further embodiment relates to compounds according to any one of embodiments 1) to 15), wherein X represents a direct bond.

21) A further embodiment relates to compounds according to any one of embodiments 1) to 18), wherein, in case X represents $NR^7$, $R^7$ represents hydrogen or $(C_{1-3})$alkyl; or, additionally, $R^7$ and $R^6$ may form a piperidine or (notably) a pyrrolidine ring including the nitrogen to which $R^7$ is attached to; or X being $NR^7$ together with $(R^3)_m$ and ring A represents 2,3-dihydro-indol-1-yl.

22) A further embodiment relates to compounds according to any one of embodiments 1) to 18), wherein, in case X represents $NR^7$, $R^7$ represents hydrogen or $(C_{1-3})$alkyl (especially hydrogen).

23) A further embodiment relates to compounds according to any one of embodiments 1) to 18), wherein X together with $(R^3)_m$ and ring A represents 2,3-dihydro-indol-1-yl.

24) A further embodiment relates to compounds according to any one of embodiments 1) to 10), wherein L represents a group —$(CH_2)_m$—, wherein m represents the integer 2 or 3;

X represents a direct bond; and ring A represents a group selected from the group consisting of pyrrol-1-yl, imidazol-1-yl, pyrazol-1-yl, triazol-1-yl, indol-1-yl, isoindol-2-yl, indazol-1-yl, benzimidazol-1-yl, benzotriazol-1-yl, 1H-pyrrolo[3,2-b]pyridin-1-yl, 1H-pyrrolo[2,3-b]pyridin-1-yl, 1H-pyrrolo[3,2-c]pyridin-1-yl, 1H-pyrrolo[2,3-c]pyridin-1-yl, 7H-pyrrolo[2,3-d]pyrimidin-7-yl, 5H-pyrrolo[3,2-d]pyrimidin-5-yl, 4H-furo[3,2-b]pyrrol-4-yl, 7H-purin-7-yl, and 9H-purin-9-yl; wherein each of said groups independently is optionally substituted with $(R^3)_m$; wherein $(R^3)_m$ represents one, or two optional substituents (i.e. m represents the integer 0, 1, or 2; especially m is 0 or 1), wherein each $R^3$ independently is selected from the group consisting of $(C_{1-4})$alkyl, $(C_{1-4})$alkoxy, and halogen; or L represents a group —$(CH_2)_m$—, wherein m represents the integer 2 or 3;

X represents a direct bond; and ring A represents a group selected from the group consisting of pyrimidin-2-yl, indol-3-yl, and 1H-pyrrolo[3,2-b]pyridin-3-yl; wherein each of said groups independently is optionally substituted with $(R^3)_m$; wherein $(R^3)_m$ represents one, or two optional substituents (i.e. m represents the integer 0, 1, or 2; especially m is 0 or 1), wherein each $R^3$ independently is selected from the group consisting of $(C_{1-4})$alkyl, $(C_{1-4})$alkoxy, and halogen; or L represents a group —$(CH_2)_m$—, wherein m represents the integer 2 or 3;

X represents a O or $NR^7$;

$R^7$ represents hydrogen or $(C_{1-3})$alkyl; and ring A represents a group selected from the group consisting of oxazol-2-yl, thiazol-2-yl, imidazol-2-yl, pyrazol-3-yl, pyridin-2-yl, pyrimid-2-yl, pyrimid-4-yl, pyridazin-3-yl, pyrazin-2-yl, benzimidazol-2-yl, benzoxazol-2-yl, benzothiazol-2-yl, quinolin-2-yl, quinazolin-2-yl, and quinoxalin-2-yl; wherein each of said groups independently is optionally substituted with $(R^3)_m$; wherein $(R^3)_m$ represents one, or two optional substituents (i.e. m represents the integer 0, 1, or 2), wherein each $R^3$ independently is selected from the group consisting of $(C_{1-4})$alkyl, $(C_{1-4})$alkoxy, and halogen.

25) A further embodiment relates to compounds according to any one of embodiments 1) to 10), wherein L represents a group —$(CH_2)_m$—, wherein m represents the integer 2 or 3;

X represents a direct bond; and ring A represents a group selected from the group consisting of indol-1-yl, benzimidazol-1-yl, 1H-pyrrolo[3,2-b]pyridin-1-yl, 1H-pyrrolo[2,3-b]pyridin-1-yl, 1H-pyrrolo[3,2-c]pyridin-1-yl, 1H-pyrrolo[2,3-c]pyridin-1-yl, 7H-pyrrolo[2,3-d]pyrimidin-7-yl, 7H-purin-7-yl, and 9H-purin-9-yl; wherein each of said groups independently is optionally substituted with $(R^3)_m$; wherein $(R^3)_m$ represents one, or two optional substituents (i.e. m represents the integer 0, 1, or 2; especially m is 0 or 1), wherein each $R^3$ independently is selected from the group consisting of $(C_{1-4})$alkyl, $(C_{1-4})$alkoxy, and halogen; or L represents a group —$(CH_2)_m$—, wherein m represents the integer 2 or 3;

X represents a direct bond; and ring A represents a group selected from the group consisting of pyrimidin-2-yl, indol-3-yl, and 1H-pyrrolo[3,2-b]pyridin-3-yl; wherein each of said groups independently is optionally substituted with $(R^3)_m$; wherein $(R^3)_m$ represents one, or two optional substituents (i.e. m represents the integer 0, 1, or 2; especially m is 0 or 1), wherein each $R^3$ independently is selected from the group consisting of $(C_{1-4})$alkyl, $(C_{1-4})$alkoxy, and halogen; or L represents a group —$(CH_2)_m$—, wherein m represents the integer 2 or 3;

X represents a O or $NR^7$;

$R^7$ represents hydrogen or $(C_{1-3})$alkyl; and ring A represents a group selected from the group consisting of pyridin-2-yl, pyrimid-2-yl, pyrimid-4-yl, pyrazin-2-yl, benzimidazol-2-yl, benzoxazol-2-yl, quinolin-2-yl, quinazolin-2-yl, and quinoxalin-2-yl wherein each of said groups independently is optionally substituted with $(R^3)_m$; wherein $(R^3)_m$ represents one, or two optional substituents (i.e. m represents the integer 0, 1, or 2), wherein each $R^3$ independently is selected from the group consisting of $(C_{1-4})$alkyl, $(C_{1-4})$alkoxy, and halogen.

26) A further embodiment relates to compounds according to any one of embodiments 1) to 25), wherein, in case X represents a direct bond, ring A is a bicyclic heteroaryl group.

27) A further embodiment relates to compounds according to any one of embodiments 1) to 26), wherein, in case X represents O or $NR^7$, ring A is a heteroaryl group which is attached to X at a carbon atom which is in alpha position to at least one (preferably two) heteroatom(s) (especially N, or O) that is/are part of the heteroaryl.

28) Another embodiment relates to compounds of formula (I) according to embodiment 1) selected from the group consisting of:

5-m-Tolyl-oxazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[2-(6-methoxy-indol-1-yl)-ethyl]-1H-pyrazol-4-yl}-amide;
5-m-Tolyl-oxazole-4-carboxylic acid {1-[2-(6-methoxy-benzoimidazol-1-yl)-ethyl]-1H-pyrazol-4-yl}-amide;
5-m-Tolyl-oxazole-4-carboxylic acid {1-[2-(6-methoxy-pyrrolo[2,3-b]pyridin-1-yl)-ethyl]-1H-pyrazol-4-yl}-amide;
5-(3-Dimethylamino-phenyl)-oxazole-4-carboxylic acid {1-[2-(4,6-dimethoxy-pyrimidin-2-yloxy)-ethyl]-1H-pyrazol-4-yl}-amide;
5-m-Tolyl-oxazole-4-carboxylic acid {1-[2-(4,6-dimethoxy-indol-1-yl)-ethyl]-1H-pyrazol-4-yl}-amide;
5-m-Tolyl-oxazole-4-carboxylic acid {1-[2-(4,6-dimethoxy-pyrimidin-2-yloxy)-ethyl]-1H-pyrazol-4-yl}-amide;
5-Phenyl-oxazole-4-carboxylic acid {1-[2-(4,6-dimethoxy-pyrimidin-2-yloxy)-ethyl]-1H-pyrazol-4-yl}-amide;
5-m-Tolyl-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid [1-(2-benzoimidazol-1-yl-ethyl)-1H-pyrazol-4-yl]-amide;
5-m-Tolyl-oxazole-4-carboxylic acid {1-[2-(5,6-dimethoxy-indol-1-yl)-ethyl]-1H-pyrazol-4-yl}-amide;
5-(3-Fluoro-phenyl)-oxazole-4-carboxylic acid {1-[2-(4,6-dimethoxy-pyrimidin-2-yloxy)-ethyl]-1H-pyrazol-4-yl}-amide;
5-m-Tolyl-oxazole-4-carboxylic acid {1-[2-(2,4-dimethoxy-pyrrolo[2,3-d]pyrimidin-7-yl)-ethyl]-1H-pyrazol-4-yl}-amide;
5-m-Tolyl-oxazole-4-carboxylic acid {1-[2-(4,6-dimethoxy-pyrrolo[2,3-b]pyridin-1-yl)-ethyl]-1H-pyrazol-4-yl}-amide;
5-m-Tolyl-oxazole-4-carboxylic acid {1-[2-(6-fluoro-indol-1-yl)-ethyl]-1H-pyrazol-4-yl}-amide;
5-m-Tolyl-oxazole-4-carboxylic acid {1-[2-(4,6-dimethoxy-pyrimidin-2-ylamino)-ethyl]-1H-imidazol-4-yl}-amide;
5-m-Tolyl-oxazole-4-carboxylic acid {1-[2-(4-methoxy-pyrimidin-2-ylamino)-ethyl]-1H-pyrazol-4-yl}-amide;
5-m-Tolyl-oxazole-4-carboxylic acid {1-[2-(5-methoxy-pyrrolo[2,3-c]pyridin-1-yl)-ethyl]-1H-pyrazol-4-yl}-amide;
5-m-Tolyl-oxazole-4-carboxylic acid {1-[2-(6-methoxy-pyrrolo[3,2-c]pyridin-1-yl)-ethyl]-1H-pyrazol-4-yl}-amide;
5-m-Tolyl-oxazole-4-carboxylic acid {1-[2-(5,6-dichloro-indol-1-yl)-ethyl]-1H-pyrazol-4-yl}-amide;
5-m-Tolyl-oxazole-4-carboxylic acid {1-[2-(2-methyl-benzoimidazol-1-yl)-ethyl]-1H-pyrazol-4-yl}-amide;
5-m-Tolyl-oxazole-4-carboxylic acid {1-[2-(6-chloro-pyrrolo[2,3-b]pyridin-1-yl)-ethyl]-1H-pyrazol-4-yl}-amide;
5-m-Tolyl-oxazole-4-carboxylic acid {1-[2-(benzooxazol-2-ylsulfanyl)-ethyl]-1H-pyrazol-4-yl}-amide;
5-m-Tolyl-oxazole-4-carboxylic acid [1-(2-indol-1-yl-ethyl)-1H-pyrazol-4-yl]-amide;
5-m-Tolyl-oxazole-4-carboxylic acid {1-[3-(4,6-dimethoxy-pyrimidin-2-ylamino)-propyl]-1H-pyrazol-4-yl}-amide;
5-m-Tolyl-thiazole-4-carboxylic acid {1-[2-(quinoxalin-2-ylamino)-ethyl]-1H-pyrazol-4-yl}-amide;
5-m-Tolyl-oxazole-4-carboxylic acid {1-[2-(quinazolin-2-ylamino)-ethyl]-1H-pyrazol-4-yl}-amide;
5-m-Tolyl-oxazole-4-carboxylic acid [1-(2-pyrrolo[2,3-b]pyridin-1-yl-ethyl)-1H-pyrazol-4-yl]-amide;
5-m-Tolyl-oxazole-4-carboxylic acid {1-[2-(7-fluoro-indol-1-yl)-ethyl]-1H-pyrazol-4-yl}-amide;
5-(3-Morpholin-4-yl-phenyl)-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid {1-[2-(5-methyl-indol-1-yl)-ethyl]-1H-pyrazol-4-yl}-amide;
5-m-Tolyl-oxazole-4-carboxylic acid {1-[2-(quinazolin-2-yloxy)-ethyl]-1H-pyrazol-4-yl}-amide;
5-m-Tolyl-oxazole-4-carboxylic acid {1-[2-(benzooxazol-2-ylamino)-ethyl]-1H-pyrazol-4-yl}-amide;
5-m-Tolyl-thiazole-4-carboxylic acid {1-[2-(benzooxazol-2-ylamino)-ethyl]-1H-pyrazol-4-yl}-amide;
5-m-Tolyl-oxazole-4-carboxylic acid {1-[2-(4,6-dimethyl-pyrimidin-2-ylamino)-ethyl]-1H-pyrazol-4-yl}-amide;
5-m-Tolyl-oxazole-4-carboxylic acid {1-[2-(quinoxalin-2-ylamino)-ethyl]-1H-pyrazol-4-yl}-amide;
5-m-Tolyl-oxazole-4-carboxylic acid {1-[2-(quinazolin-2-ylamino)-ethyl]-1H-imidazol-4-yl}-amide;
5-m-Tolyl-oxazole-4-carboxylic acid {1-[2-(7-methyl-indol-1-yl)-ethyl]-1H-pyrazol-4-yl}-amide;
5-m-Tolyl-oxazole-4-carboxylic acid {1-[2-(3-methoxy-phenyl)-ethyl]-1H-pyrazol-4-yl}-amide;
5-m-Tolyl-oxazole-4-carboxylic acid {1-[2-(benzo[1,3]dioxol-5-yloxy)-ethyl]-1H-pyrazol-4-yl}-amide;
5-m-Tolyl-oxazole-4-carboxylic acid {1-[2-(5-fluoro-pyridin-2-ylamino)-ethyl]-1H-pyrazol-4-yl}-amide;
5-m-Tolyl-oxazole-4-carboxylic acid {1-[2-(4,6-dimethyl-pyrimidin-2-yloxy)-ethyl]-1H-pyrazol-4-yl}-amide;
5-m-Tolyl-oxazole-4-carboxylic acid {1-[2-(6-methoxy-purin-7-yl)-ethyl]-1H-pyrazol-4-yl}-amide;
5-m-Tolyl-oxazole-4-carboxylic acid {1-[2-(5-chloro-benzooxazol-2-ylamino)-ethyl]-1H-pyrazol-4-yl}-amide;
5-m-Tolyl-oxazole-4-carboxylic acid {1-[2-(3-methoxy-phenoxy)-ethyl]-1H-pyrazol-4-yl}-amide;
5-m-Tolyl-oxazole-4-carboxylic acid {1-[2-(4-methoxy-pyrrolo[2,3-b]pyridin-1-yl)-ethyl]-1H-pyrazol-4-yl}-amide;
5-Phenyl-oxazole-4-carboxylic acid {1-[2-(2-methyl-benzoimidazol-1-yl)-ethyl]-1H-pyrazol-4-yl}-amide;
5-(4-Trifluoromethyl-phenyl)-oxazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[2-(5-chloro-indol-1-yl)-ethyl]-1H-pyrazol-4-yl}-amide;
5-m-Tolyl-oxazole-4-carboxylic acid {1-[3-(2,3-dihydro-indol-1-yl)-propyl]-1H-pyrazol-4-yl}-amide;
5-m-Tolyl-oxazole-4-carboxylic acid {1-[2-(5,6-dimethoxy-indol-1-yl)-ethyl]-3,5-dimethyl-1H-pyrazol-4-yl}-amide;
5-m-Tolyl-oxazole-4-carboxylic acid [1-(3-indol-1-yl-propyl)-1H-pyrazol-4-yl]-amide;
5-(2-Fluoro-phenyl)-oxazole-4-carboxylic acid {1-[2-(5,6-dimethoxy-indol-1-yl)-ethyl]-1H-pyrazol-4-yl}-amide;
5-m-Tolyl-oxazole-4-carboxylic acid {1-[2-(4-fluoro-pyridin-2-ylamino)-ethyl]-1H-pyrazol-4-yl}-amide;
5-m-Tolyl-oxazole-4-carboxylic acid {1-[2-(2,3-dihydro-indol-1-yl)-ethyl]-1H-pyrazol-4-yl}-amide;
5-m-Tolyl-oxazole-4-carboxylic acid {1-[(R)-2-(4,6-dimethoxy-pyrimidin-2-ylamino)-propyl]-1H-pyrazol-4-yl}-amide;

5-(3-Cyano-phenyl)-oxazole-4-carboxylic acid {1-[2-(4,6-dimethoxy-pyrimidin-2-ylamino)-ethyl]-1H-pyrazol-4-yl}-amide;

5-Phenyl-oxazole-4-carboxylic acid {1-[2-(5,6-dimethoxy-indol-1-yl)-ethyl]-1H-pyrazol-4-yl}-amide;

rac-5-m-Tolyl-oxazole-4-carboxylic acid {1-[1-(4,6-dimethoxy-pyrimidin-2-yl)-pyrrolidin-2-ylmethyl]-1H-pyrazol-4-yl}-amide;

5-m-Tolyl-oxazole-4-carboxylic acid [1-(2-pyrrolo[3,2-b]pyridin-1-yl-ethyl)-1H-pyrazol-4-yl]amide;

5-m-Tolyl-oxazole-4-carboxylic acid {1-[(S)-2-(4,6-dimethoxy-pyrimidin-2-ylamino)-propyl]-1H-pyrazol-4-yl}-amide;

5-m-Tolyl-oxazole-4-carboxylic acid {1-[2-(1-methyl-1H-indol-3-yl)-ethyl]-1H-pyrazol-4-yl}-amide;

5-m-Tolyl-oxazole-4-carboxylic acid {1-[2-(4-methoxy-pyridin-2-ylamino)-ethyl]-1H-pyrazol-4-yl}-amide;

5-(3,4-Dimethyl-phenyl)-thiazole-4-carboxylic acid {1-[2-(5-methoxy-1H-indol-3-yl)-ethyl]-1H-pyrazol-4-yl}-amide;

5-m-Tolyl-oxazole-4-carboxylic acid {1-[3-(6-methoxy-2,3-dihydro-indol-1-yl)-propyl]-1H-pyrazol-4-yl}-amide;

5-(6-Methoxy-pyridin-3-yl)-thiazole-4-carboxylic acid {1-[2-(5-methoxy-1H-indol-3-yl)-ethyl]-1H-pyrazol-4-yl}-amide;

5-m-Tolyl-oxazole-4-carboxylic acid {1-[2-(6-methoxy-pyrrolo[3,2-c]pyridin-1-yl)-ethyl]-3,5-dimethyl-1H-pyrazol-4-yl}-amide;

5-(3-Methoxy-4-methyl-phenyl)-oxazole-4-carboxylic acid {1-[2-(4,6-dimethoxy-pyrimidin-2-ylamino)-ethyl]-1H-pyrazol-4-yl}-amide;

5-m-Tolyl-oxazole-4-carboxylic acid {1-[2-(1H-indol-3-yl)-ethyl]-1H-pyrazol-4-yl}-amide;

5-(4-Methoxy-phenyl)-oxazole-4-carboxylic acid {1-[2-(5,6-dimethoxy-indol-1-yl)-ethyl]-1H-pyrazol-4-yl}-amide;

5-(3-Pyrrolidin-1-yl-phenyl)-oxazole-4-carboxylic acid {1-[2-(4,6-dimethoxy-pyrimidin-2-ylamino)-ethyl]-1H-pyrazol-4-yl}-amide;

5-m-Tolyl-oxazole-4-carboxylic acid [1-(2-indol-1-yl-ethyl)-3,5-dimethyl-1H-pyrazol-4-yl]amide;

5-m-Tolyl-oxazole-4-carboxylic acid {1-[2-(4,6-dimethoxy-5-methyl-pyrimidin-2-ylamino)-ethyl]-1H-pyrazol-4-yl}-amide;

5-(3-Fluoro-phenyl)-oxazole-4-carboxylic acid {1-[2-(5,6-dimethoxy-indol-1-yl)-ethyl]-1H-pyrazol-4-yl}-amide;

5-(3-Methoxy-4-methyl-phenyl)-oxazole-4-carboxylic acid {1-[2-(5-methoxy-1H-indol-3-yl)-ethyl]-1H-pyrazol-4-yl}-amide;

5-Phenyl-oxazole-4-carboxylic acid {1-[2-(4,6-dimethoxy-pyrimidin-2-ylamino)-ethyl]-1H-pyrazol-4-yl}-amide;

5-m-Tolyl-oxazole-4-carboxylic acid {1-[2-(4-methoxy-1H-indol-3-yl)-ethyl]-1H-pyrazol-4-yl}-amide;

5-(3-Methoxy-4-methyl-phenyl)-oxazole-4-carboxylic acid {1-[2-(5,6-dimethoxy-indol-1-yl)-ethyl]-1H-pyrazol-4-yl}-amide;

5-(4-Methoxy-phenyl)-oxazole-4-carboxylic acid {1-[2-(4,6-dimethoxy-pyrimidin-2-ylamino)-ethyl]-1H-pyrazol-4-yl}-amide;

5-m-Tolyl-oxazole-4-carboxylic acid {1-[2-(5-fluoro-1H-indol-3-yl)-ethyl]-1H-pyrazol-4-yl}-amide;

5-m-Tolyl-oxazole-4-carboxylic acid {1-[3-(4-ethoxy-6-methoxy-pyrimidin-2-yl)-propyl]-1H-pyrazol-4-yl}-amide;

5-Biphenyl-3-yl-oxazole-4-carboxylic acid {1-[2-(5-methoxy-1H-indol-3-yl)-ethyl]-1H-pyrazol-4-yl}-amide;

5-Phenyl-thiazole-4-carboxylic acid {1-[2-(5-methoxy-1H-indol-3-yl)-ethyl]-1H-pyrazol-4-yl}-amide;

5-m-Tolyl-oxazole-4-carboxylic acid {1-[2-(5,6-dimethoxy-benzoimidazol-1-yl)-ethyl]-1H-pyrazol-4-yl}-amide;

5-Isoxazol-3-yl-oxazole-4-carboxylic acid {1-[2-(5-methoxy-1H-indol-3-yl)-ethyl]-1H-pyrazol-4-yl}-amide;

5-(3,4-Dimethyl-phenyl)-oxazole-4-carboxylic acid {1-[2-(5-methoxy-1H-indol-3-yl)-ethyl]-1H-pyrazol-4-yl}-amide;

5-(3,4-Dimethyl-phenyl)-oxazole-4-carboxylic acid {1-[2-(4,6-dimethoxy-pyrimidin-2-ylamino)-ethyl]-1H-pyrazol-4-yl}-amide;

5-m-Tolyl-oxazole-4-carboxylic acid {1-[3-(6-methoxy-indol-1-yl)-propyl]-1H-pyrazol-4-yl}-amide;

5-m-Tolyl-oxazole-4-carboxylic acid {1-[3-(4-methoxy-pyrimidin-2-ylamino)-propyl]-1H-pyrazol-4-yl}-amide;

5-m-Tolyl-oxazole-4-carboxylic acid {1-[2-(5-chloro-6-methoxy-indol-1-yl)-ethyl]-1H-pyrazol-4-yl}-amide;

5-(4-Methoxy-phenyl)-oxazole-4-carboxylic acid {1-[2-(5-methoxy-1H-indol-3-yl)-ethyl]-1H-pyrazol-4-yl}-amide;

5-m-Tolyl-thiazole-4-carboxylic acid {1-[2-(5-methoxy-1H-indol-3-yl)-ethyl]-1H-pyrazol-4-yl}-amide;

5-m-Tolyl-oxazole-4-carboxylic acid {1-[2-(2,6-dimethoxy-pyrimidin-4-ylamino)-ethyl]-1H-pyrazol-4-yl}-amide;

5-m-Tolyl-oxazole-4-carboxylic acid {1-[3-(4,6-dimethoxy-pyrimidin-2-yl)-propyl]-1H-pyrazol-4-yl}-amide;

5-m-Tolyl-oxazole-4-carboxylic acid {1-[2-(5-methoxy-1H-indol-3-yl)-ethyl]-1H-imidazol-4-yl}-amide;

5-(3-Fluoro-phenyl)-oxazole-4-carboxylic acid {1-[2-(4,6-dimethoxy-pyrimidin-2-ylamino)-ethyl]-1H-pyrazol-4-yl}-amide;

5-(3,4-Dimethyl-phenyl)-oxazole-4-carboxylic acid {1-[2-(5,6-dimethoxy-indol-1-yl)-ethyl]-1H-pyrazol-4-yl}-amide;

5-m-Tolyl-oxazole-4-carboxylic acid {1-[2-(5-methoxy-1-methyl-1H-indol-3-yl)-ethyl]-1H-pyrazol-4-yl}-amide;

5-(3-Chloro-phenyl)-thiazole-4-carboxylic acid {1-[2-(5-methoxy-1H-indol-3-yl)-ethyl]-1H-pyrazol-4-yl}-amide;

5-(3-Methyl-isoxazol-5-yl)-oxazole-4-carboxylic acid {1-[2-(5-methoxy-1H-indol-3-yl)-ethyl]-1H-pyrazol-4-yl}-amide;

5-(3-Trifluoromethyl-phenyl)-oxazole-4-carboxylic acid {1-[2-(5-methoxy-1H-indol-3-yl)-ethyl]-1H-pyrazol-4-yl}-amide;

5-m-Tolyl-oxazole-4-carboxylic acid {1-[2-(5-methoxy-1H-pyrrolo[3,2-b]pyridin-3-yl)-ethyl]-1H-pyrazol-4-yl}-amide;

5-(3-Trifluoromethoxy-phenyl)-oxazole-4-carboxylic acid {1-[2-(5-methoxy-1H-indol-3-yl)-ethyl]-1H-pyrazol-4-yl}-amide;

5-(2-Fluoro-phenyl)-oxazole-4-carboxylic acid {1-[2-(5-methoxy-1H-indol-3-yl)-ethyl]-1H-pyrazol-4-yl}-amide;

5-(3-Fluoro-phenyl)-oxazole-4-carboxylic acid {1-[2-(5-methoxy-1H-indol-3-yl)-ethyl]-1H-pyrazol-4-yl}-amide;

5-(3-Chloro-phenyl)-oxazole-4-carboxylic acid {1-[2-(5-methoxy-1H-indol-3-yl)-ethyl]-1H-pyrazol-4-yl}-amide; and 5-Phenyl-oxazole-4-carboxylic acid {1-[2-(5-methoxy-1H-indol-3-yl)-ethyl]-1H-pyrazol-4-yl}-amide.

The compounds of formula (I) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I).

For avoidance of any doubt, if compounds are described as useful for the prevention or treatment of certain diseases, such compounds are likewise suitable for use in the preparation of a medicament for the prevention or treatment of said diseases.

The compounds according to formula (I) are useful for the prevention or treatment of diseases related to the orexin system.

Such diseases related to the orexin system may be selected from the group consisting of all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

In a sub-embodiment, such diseases related to the orexin system may be selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders (notably all types of insomnias, especially primary insomnia).

In another sub-embodiment, such diseases related to the orexin system may be selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another sub-embodiment, such diseases related to the orexin system may be selected from the group consisting of eating disorders that comprise metabolic dysfunction; dysregulated appetite control; compulsive obesities; emeto-bulimia or anorexia nervosa.

In another sub-embodiment, such diseases related to the orexin system may be selected from the group consisting of all types of addictions (especially psychoactive substance use, abuse, seeking and reinstatement) that comprise all types of psychological or physical addictions and their related tolerance and dependence components.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake.

Sleep disorders include all types of parasomnias, insomnias, sleep-related dystonias; restless leg syndrome; sleep apneas; jet-lag syndrome; shift-work syndrome, delayed or advanced sleep phase syndrome or insomnias related to psychiatric disorders.

Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance.

Addictions may be defined as addiction to one or more rewarding stimuli, notably to one rewarding stimulus. Such rewarding stimuli may be of either natural or synthetic origin. Psychoactive substance use, abuse, seeking and reinstatement are defined as all types of psychological or physical addictions and their related tolerance and dependence components.

Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In another embodiment, such diseases or disorders related to the orexin system may be defined as comprising notably mental health diseases or disorders relating to orexinergic dysfunctions; especially sleep disorders, anxiety disorders, addiction disorders, cognitive dysfunctions, mood disorders, or appetite disorders; wherein sleep disorders comprise dyssomnias, parasomnias, sleep disorders associated with a general medical condition and substance-induced sleep disorders (especially sleep disorders comprise all types of insomnias, sleep-related dystonias; restless leg syndrome; sleep apneas; jet-lag syndrome; shift work sleep disorder, delayed or advanced sleep phase syndrome, or insomnias related to psychiatric disorders; and, in addition, sleep disorders associated with aging; intermittent treatment of chronic insomnia; situational transient insomnia (new environment, noise) or short-term insomnia due to stress; grief; pain or illness); wherein anxiety disorders comprise generalized anxiety disorders (GAD), obsessive compulsive disorders (OCDs), acute stress disorders, posttraumatic stress disorders (PTSDs), panic anxiety disorders (PADs) including panic attacks, phobic anxieties (PHOBs), specific phobia, social phobia (social anxiety disorder), avoidance, somatoform disorders including hypochondriasis, separation anxiety disorder, anxiety disorders due to a general medical condition, and substance induced anxiety disorders; wherein addiction disorders comprise addictions to one or more rewarding stimuli of either natural or synthetic origin such as cocaine, amphetamines, opiates [of natural or (semi-)synthetic origin such as morphine or heroin], cannabis, ethanol, mescaline, nicotine, and the like}, which substances/drugs may be consumed alone or in combination; or other rewarding stimuli {of either natural origin (such as food, sweet, fat, or sex, and the like), or synthetic origin [such as gambling, or internet/IT (such as immoderate gaming, or inappropriate involvement in online social networking sites or blogging), and the like]; wherein appetite disorders comprise eating disorders (comprising eating disorders associated with excessive food intake and complications associated therewith; anorexias; compulsive eating disorders; obesity (due to any cause, whether genetic or environmental); obesity-related disorders including overeating and obesity observed in Type 2 (non-insulin-dependent) diabetes patients; bulimias including bulimia nervosa; cachexia; and binge eating disorder) and drinking disorders (comprising include polydipsias in psychiatric disorders and all other types of excessive fluid intake); wherein cognitive dysfunctions relate to the enhancement or maintenance of memory in patients who have been diagnosed as having, or being at risk of developing, diseases or disorders in which diminished memory (notably declarative or procedural) is a symptom [in particular dementias such as frontotemporal dementia, or dementia with Lewy bodies, or (especially) Alzheimer's disease]; and wherein mood disorders comprise major depressive episode, manic episode, mixed episode and hypomanic episode; depressive disorders including major depressive disorder, dysthymic disorders; bipolar disorders including bipolar I disorder, bipolar II disorder (recurrent major depressive episodes with hypomanic episodes), cyclothymic disorder; and mood disorders comprise mood disorder due to a general medical condition (including the subtypes with depressive features, with major depressive-like episode, with manic features, and with mixed features), substance-induced mood disorder (including the subtypes with depressive features, with manic features, and with mixed features), such as especially major depressive episode, major depressive disorder, mood disorder due to a general medical condition; and substance-induced mood disorder.

In addition, further diseases related to the orexin system are selected from treating, controlling, ameliorating or reducing the risk of epilepsy, including absence epilepsy; treating or controlling pain, including neuropathic pain; treating or controlling Parkinson's disease; treating or controlling psychosis including acute mania and bipolar disorder; treating or controlling stroke, particularly ischemic or haemorrhagic stroke; blocking an emetic response i.e. nausea and vomiting; treating or controlling agitation, in isolation or co-morbid with another medical condition.

In the context of the present invention, it is to be understood that, in case certain environmental conditions such as stress or fear (wherein stress may be of social origin (e.g. social stress) or of physical origin (e.g. physical stress), including stress caused by fear) facilitate or precipitate any of the disorders or diseases as defined before, the present compounds may be particularly useful for the treatment of such environmentally conditioned disorder or disease.

Preparation of Compounds of Formula (I):

Compounds of formula (I) can be manufactured by the methods given below, by the methods given in the Examples or by analogous methods. Optimum reaction conditions may vary with the particular reactants or solvents used, but such conditions can be determined by a person skilled in the art by routine optimization procedures. If not indicated otherwise, the groups U, V, L, X, Y, $R^1$, $(R^2)_n$ and $(R^3)_m$ and ring A are as defined for formula (I).

The compounds of formula (I) may in general be prepared by reacting a compound of structure 1 with a compound of structure 2. A compound of structure 2 can be coupled with the corresponding carboxylic acid derivative of structure 1 using standard amide coupling conditions such as EDC/HOBt, HOAt/DCC, TBTU, HATU or PyBOP in the presence of a base such as DIPEA or $Et_3N$ at rt in a suitable solvent such as DCM, DMF, MeCN or mixtures thereof (Step a, Scheme 1).

Alternatively, compounds of formula (I) may in general be prepared by alkylating a compound of structure 3 with a compound of structure 4 wherein Z represents for example Cl—, Br— or $MeSO_3$—, usually in presence of base such as $K_2CO_3$ or $Cs_2CO_3$, at about 65 to 110° C. in solvents such as DCM, DMF, MeCN, xylene, dioxane or mixtures thereof, optionally in a sealed tube in presence or absence of microwave irradiation (Step b, Scheme 1).

Carboxylic acids of structure 1 are commercially available or well known in the art, and may for example be prepared according to methods published in WO 2009/077954, WO2009/016560, WO2009/014674, WO2010/044054, WO2010/038200, and WO2010/004507.

Scheme 1: Synthesis of final compounds of structure of formula (I).

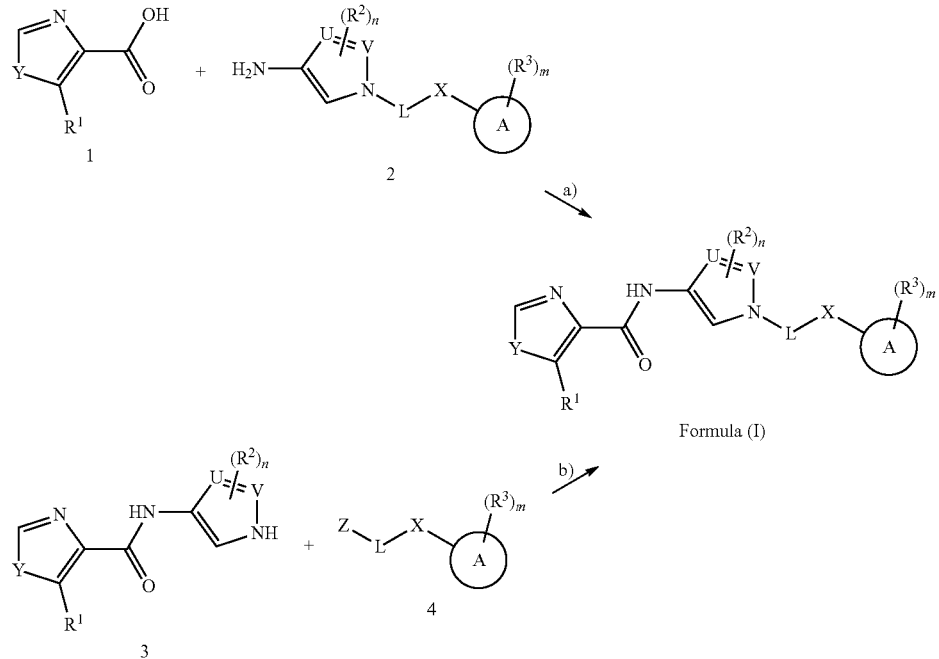

Compounds of structure 2 can be prepared in various ways, e.g. pathways A to D as outlined in Scheme 2 to 4. Starting materials are well known in the art and/or commercially available; or they may be synthesized according to methods described in the literature or herein below. In case $R^1$ or ring A, or a substituent thereof, is a heteroaryl moiety, such heteroaryl may be introduced using well known and generally commerially available building blocks (literature for precursors of heteroaryl-containing groups: see e.g. T. Eicher, S. Hauptmann "The chemistry of Heterocycles: Structure, Reactions, Syntheses, and Applications", 2nd Edition 2003, Wiley, ISBN 978-3-527-30720-3; A. R. Katrizky, C. W. Rees, E. F. V. Scriven (Eds.) "Comprehensive Heterocyclic Chemistry II" 1996, Elsevier, ISBN 0-08-042072-9). In some instances, such heteroaryl groups are obtained with certain functional groups (e.g. esters or carboxylic acids) that need to be interconverted using routine procedures to appropriate functional groups (e.g. aldehydes or alcohols) as used in the procedures below.

Reactions of alcohols with methanesulfonyl chloride may result in the formation of the respective chloride or the respective methanesulfonate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

Pathway A:

Compounds of structure 2 may be prepared by reacting commercially available nitro-analog 5 with a compound of structure 4 to yield compounds of structure 6 in the presence of base such as NaH, $Cs_2CO_3$ or $Na_2CO_3$ at about 80° C. to 100° C. in a suitable solvent such as DCM, DMF, MeCN, in a sealed tube in presence or absence of microwave irradiation. Reduction of the nitro group can be achieved either by hydrogenation in presence of metal catalyst such as Pd/C, Pt/C or $PtO_2$ in a suitable solvent such as MeOH, EtOH or EtOAc at rt, or by reduction with a metal such as iron in a solvent mixture such as $H_2O$/EtOH in the presence of $NH_4Cl$ at about rt to 100° C.

Pathway B:

In case A represents a pyridine and X represents NH, compounds of structure 2 may be prepared by reacting a pyridine analog 7, which is commercially available or well known in the art, with 2-chloroacetyl chloride. Thus obtained compounds of structure 8 can be further reacted with commercially available compounds of structure 5 to yield compounds of structure 9, in the presence of a base such as $K_2CO_3$ or $Cs_2CO_3$ in solvents such as MeCN at about 80° C. Reduction of the amide of structure 9, in the presence of an reducing agent such as $BH_3$-THF complex in THF leads to compounds of structure 10. Subsequent reduction of the nitro group using methods as described before leads to compounds of structure 2.

Pathway A

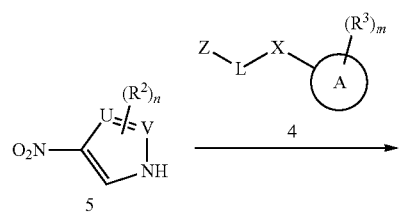

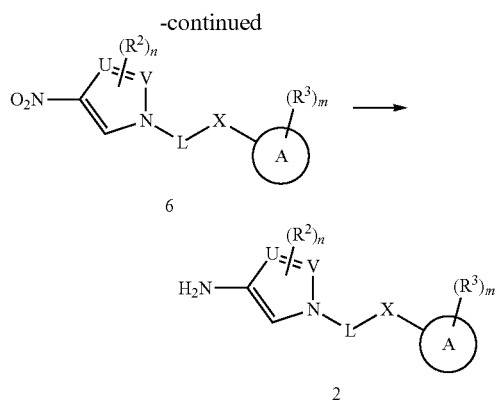

Pathway B

Scheme 2: Synthesis of compounds of structure 2.

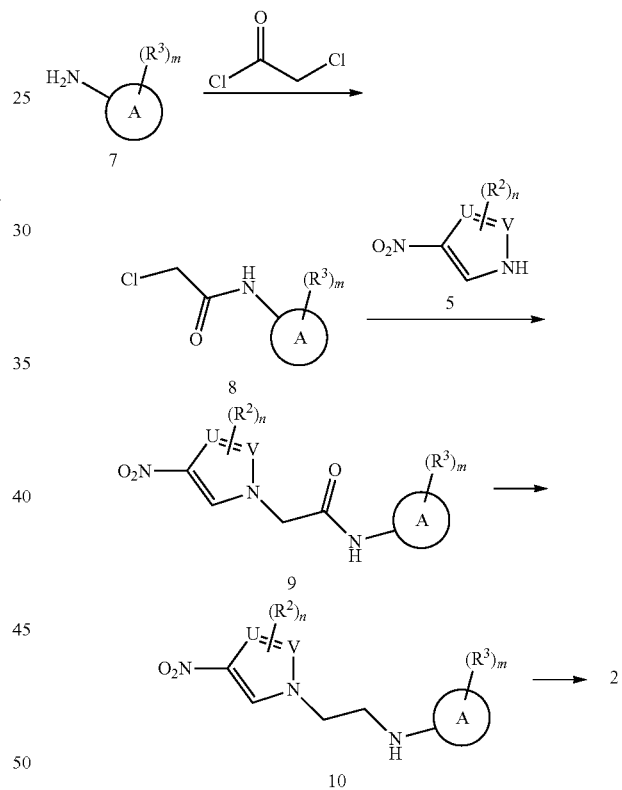

Pathway C:

In case A represents a N-linked indole, L represents $CH_2$—$CH_2$ and X represents a bond, compounds of structure 2 may be prepared by reacting commercially available compounds of structure 5 with commercially available 2-bromo-1,1-dimethoxyethane in the presence of a base such as $Cs_2CO_3$ or $Na_2CO_3$ in a suitable solvent such as MeCN or DCM at about 85° C. Acetal deprotection to aldehyde of structure 12 can be performed under aq. acidic conditions such as hydrochloric acid in solvents such as THF or dioxane. Further conversion can be performed by reductive amination in the presence of an indoline and in presence of a reducing agent such as $NaBH_4$ or STAB at rt, to yield compounds of structure 13. Reduction of the nitro group using the methods described above leads to indoline compounds of structure 14. In an optional further step, compounds of structure 2 wherein A represents an indole are obtained using standard oxidation conditions such as MnO₂ or TPAP/NMO in suitable solvents such as acetone, DCM or MeCN at rt.

Pathway C

Scheme 3: Synthesis of compounds of structure 2.

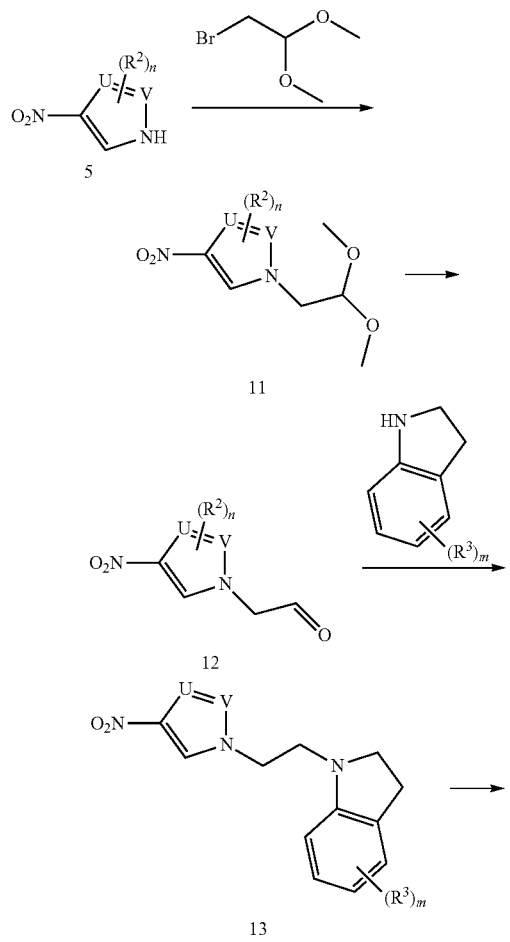

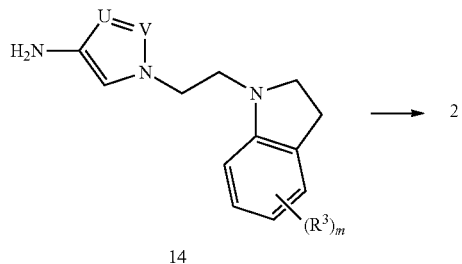

Pathway D:

In case A represents a heteroaryl group which is attached to the rest of the molecule at a carbon atom which is in alpha position to at least one heteroatom such as 4-pyrimidine or 2-pyrimidine (as shown in scheme 4), compounds of structure 2 may be prepared by reacting commercially available compounds of structure 5, in case X represents O, with bromo-alkyl-alcohol to yield compounds of structure 15, in the presence of base such as NaH, Cs₂CO₃, K₂CO₃ at temperature about rt to 100° C., in suitable solvents such as DCM, DMF, MeCN or mixtures thereof. Compounds of structure 15 can be coupled with the appropriate commercially available halo-heteroaryl, eg. 2-chloro-pyrimidines or 4-chloro-pyrimidines. Subsequent reduction of the nitro group using the methods described above yields compounds of structure 2.

In case X represents NH, compounds of structure 5 are alkylated with Boc-protected amine-alkyl-bromide to compounds of structure 17. Compounds of structure 17 can to be deprotected either with TFA in DCM at about 0° C. to rt, or with 4 N HCl in dioxane at rt. Coupling with the appropriate commercially available halo-heteroaryl, eg. 2-chloro-pyrimidines or 4-chloro-pyrimidines at about 80° to 140° C. in suitable solvents such as MeCN, THF, dioxane, xylene, DMF in a sealed tube either in presence or absence of microwave irradiation and subsequent reduction of the nitro group yields compounds of structure 2.

Pathway D

Scheme 4: Synthesis of compounds of structure 2

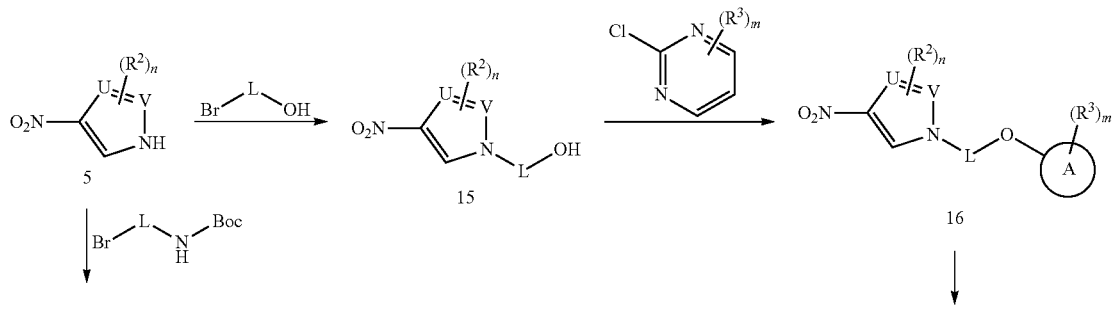

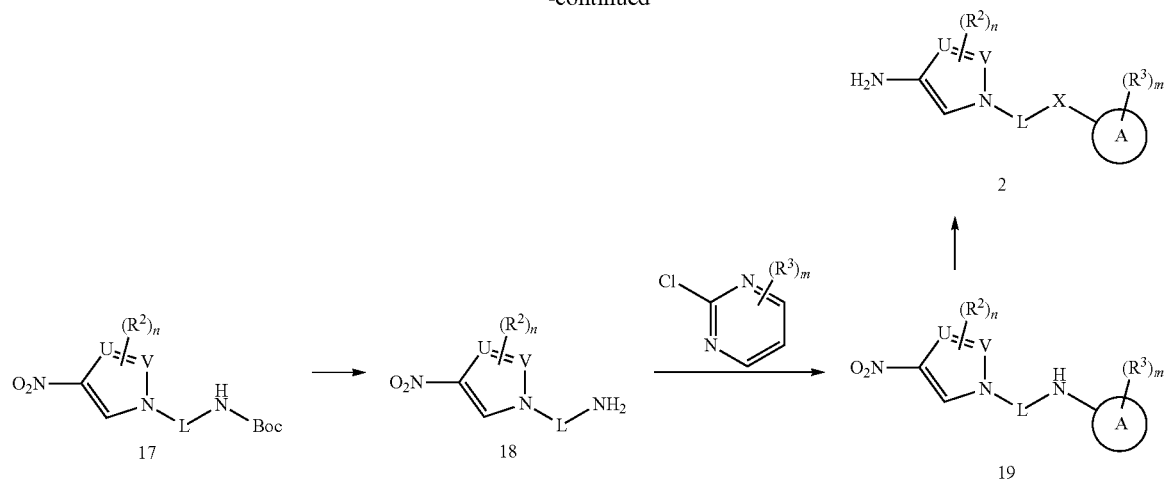

Compounds of structure 3 may be prepared from amines of structure 20 (which are either commercially available or synthesized from the commercially available nitro-analog 5), and corresponding carboxylic acid derivatives of structure 1 using standard amide coupling conditions (Scheme 5).

Scheme 5: Amide-coupling to yield intermediate 3

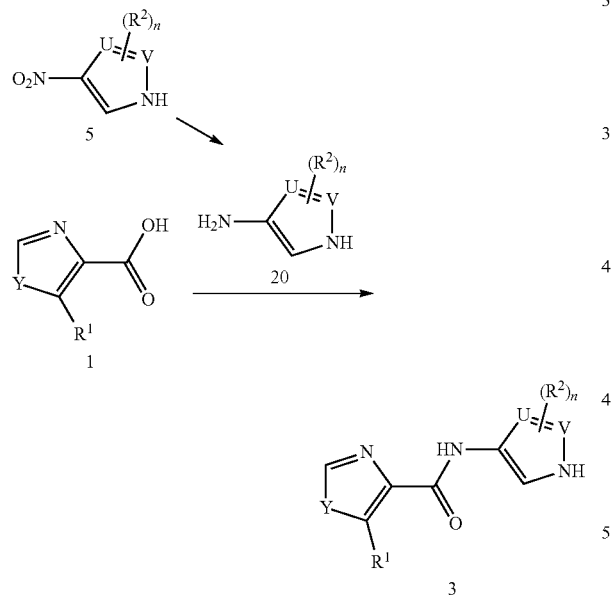

The synthesis of compounds of structure 4, wherein Z represents for example Cl—, Br— or MeSO₃— is outlined in Scheme 6 and 7.

In case A represents a 3-N-2-methyl-benzimidazole and X represents a bond, compounds of structure 4 may be prepared by reacting commercially available 2-methyl-benzimidazoles of structure 21 with 2-bromo-ethanol, in presence of base such as $Cs_2CO_3$, $K_2CO_3$ or NaH, in solvents such as DMF, MeCN, toluene at about rt to 150° C. The obtained alcohol of structure 22 may be converted to the chloro-analog of structure 4 in the presence of $SOCl_2$, in solvents such as DCM at 0° C. to rt (Scheme 6).

In case A represents an asymmetric 3-N-benzimidazole and X represents a bond, compounds of structure 4 can be prepared by reacting commercially available 1-bromo-2-nitrophenyl-analogs of structure 23 with 2-amino-ethanol, in presence of base such as DIPEA, $Et_3N$ or excess 2-amino-ethanol. Catalytic hydrogenation of the nitro-compounds of structure 24 yields the amines of structure 25. Compounds of structure 26 may be prepared by a condensation reaction in the presence of formic acid in a solvent such as THF at about 80° C. Compounds of structure 26 can be chlorinated or brominated in the presence of thionyl chloride or $CBr_4/PPh_3$ respectively, in solvents such as DCM to obtain compounds of structure 4 (Scheme 6).

Scheme 6: Synthesis of compounds of structure 4.

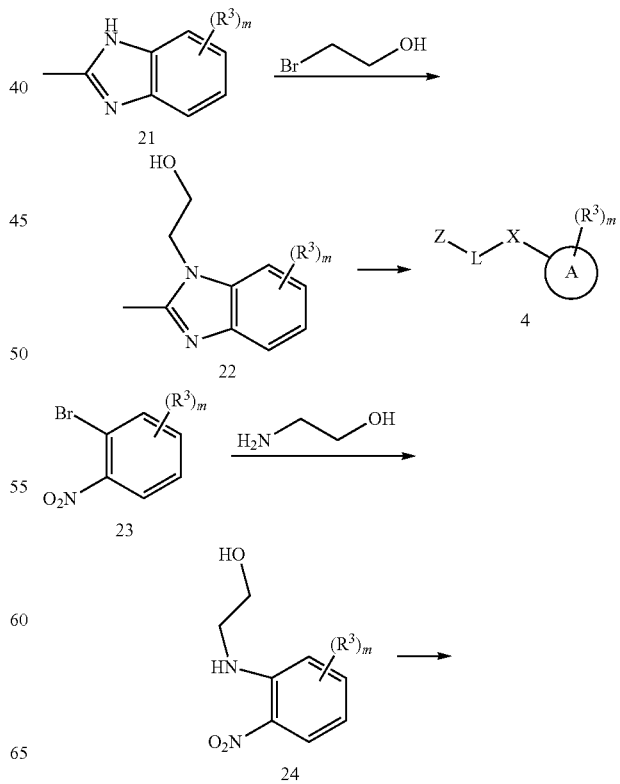

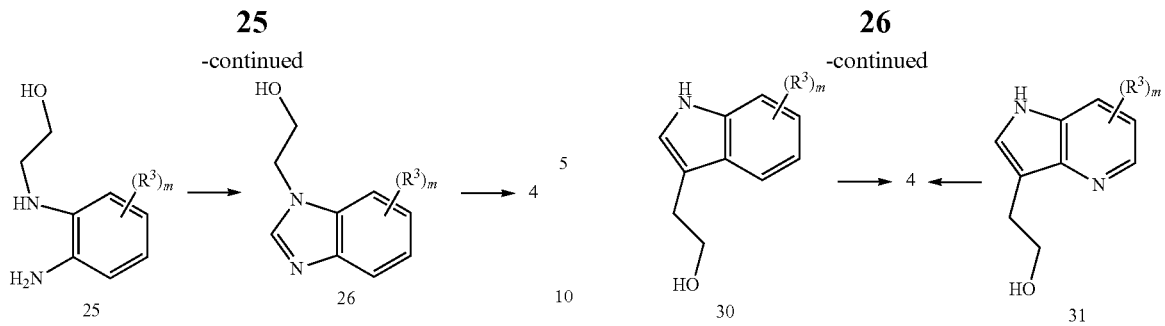

In case A represents a 3-indole, X represents a bond and Z represents Cl— or Br—, compounds of structure 4 may be prepared by reacting commercially available indoles of structure 27 with oxayl chloride in a solvent such as ether at about 0° C. to rt. Compounds of structure 28 are immediately converted to the α-keto-ester 29 in the presence of a base such as Et$_3$N or DIPEA in EtOH, at about 0° C. to rt. The α-keto-ester 29 can be reduced to alcohols of structure 30 in the presence of LiAlH$_4$ in a suitable solvent such as THF or dioxane at about 0° C. followed by bromination or chlorination as described before, or by sulfonylation with methanesulfonyl chloride in the presence of base such as DIPEA, Et$_3$N or DMAP at about 0° C. to 80° C. to yield compounds of structure 4 (Schema 7).

In case A represents an aza-indole, X represents a bond and Z represents Cl—, Br— or MeSO$_3$—, compounds of structure 4 may be prepared from aza-indoles of structure 31 (which may be synthesized according to literature procedures: e.g. Organic Letters, 2009, 11, 5142-5145) which can be brominated, chlorinated or mesylated using the methods described above (Scheme 7).

Scheme 7: Synthesis of compounds of structure 4

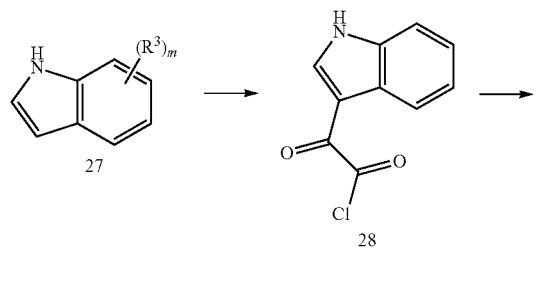

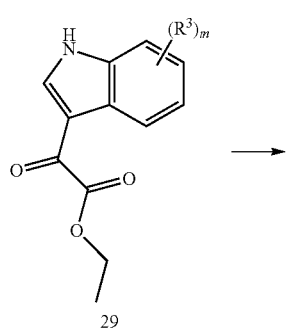

In case L is CH$_2$CH$_2$CH$_2$ and X represents a bond, compounds of structure 4 may be prepared from well known and widely commercially available aldehydes of structure 32 using a Wittig-olefination with methyl(triphenylphosphoranylidene)-acetate to yield compounds of structure 33. Hydrogentation of the C—C-double bond in the presence of cat. amounts of Pd/C under H$_2$ atmosphere in solvents such as MeOH or DCM at around rt yield compounds of structure 34. Reduction to alcohols of structure 35 may be achieved in presence of reducing agents such as LiAlH$_4$ in solvents such as THF or dioxane, at about 0° C. to rt. Bromination, chlorination or sulfonylation is be achieved using the methods described above (Scheme 8).

Scheme 8: Synthesis of compounds of structure 4

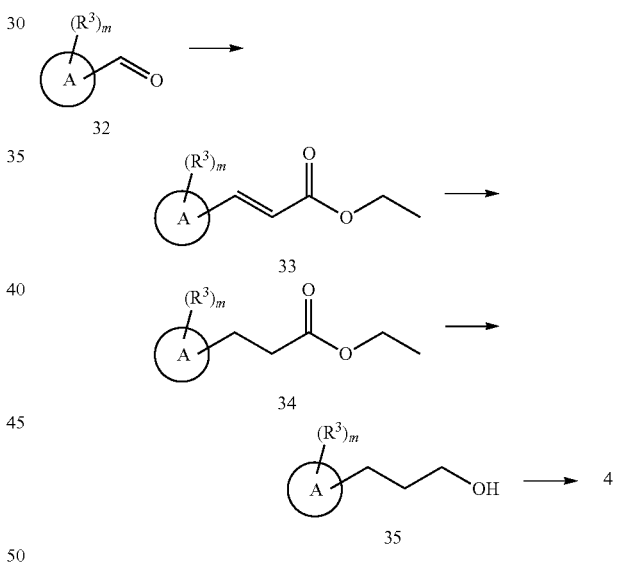

In case A represents a heteroaryl group which is linked to L through a nucleophilic nitrogen atom (X is a bond), such as for example N-linked-indoles, N-linked aza-indoles or N-linked benzimidazoles, compounds of formula (I) may be prepared by alkylating such heteroaryl compounds of structure 37 (wherein $Z^2$ is H) for example with sulfonesters of structure 36 (wherein $Z^1$ is for example Me- or pMePh-). Deprotonation of compound of structure 37 with a base such as NaH at rt in suitable solvents such as DMF or THF is followed by the addition of compounds of structure 36 (Scheme 9, Step a).

In case A represents aryl or heteroaryl and X equals 0, compounds of formula (I) may be prepared from sulfonesters of structure 36 by nucleophilic substitution with compounds of structure 37 (wherein $Z^2$ is OH). Compounds of structure 37 are deprotonated in the presence of base such as NaH, in suitable solvents such as THF, DMF or NMP, followed by the addition of compounds of structure 36 (Scheme 9, Step a).

In case A represents aryl or heteroaryl and X equals S, compounds of formula (I) can be prepared from sulfonesters of structure 36 by nucleophilic substitution with compounds of structure 37 (wherein $Z^2$ equals S), usually in presence of base such as NaH, Et₃N or DIPEA in suitable a solvent such as THF, DMF or DCM (Scheme 9, Step a).

Alternatively, in case A represents a 2-pyrimidine, a 2-quinazoline, a 2-quinoxaline, a 2-benzoxazole or a 4-pyrimidine, compounds of structure of formula (I) can be prepared, in case X is O, from alcohols of structure 38 by nucleophilic substitution with 2-chloro-pyrimidines, or 2-chloro-quinazolines, 2-chloro-quinoxalines, 2-chloro-benzoxazoles or 4-chloro-pyrimidines of structure 40a, or 2-methylsulfonyl-pyrimidines of structure 40b; usually in presence of base such as NaH in a solvent such as xylene, dioxane, THF, DMF, MeCN, at about rt to 100° C. in presence or absence of microwave irradiation (Scheme 9, Step b). Similarly, in case X is N, compounds of structure of formula (I) can be prepared by reaction of amines of structure 39 with 2-chloro-pyrimidines, 2-chloro-quinazolines, 2-chloro-quinoxalines, 2-chloro-benzoxazoles or 4-chloro-pyrimidines of structure 40a or 2-methylsulfonyl-pyrimidines of structure 40b (Scheme 9, Step b).

In case X is NH, L equals $CH_2$—$CH_2$, compounds of formula (I) can be prepared by reductive amination of aldehydes of structure 41 with amines of structure 42 in the presence of an reducing agent such as $NaBH_4$ or STAB in solvents such as DCM at rt to 60° C. (Scheme 9, Step c). In case X is N-alkyl, such reaction may be performed with alkylated derivates of 42. Alternatively, compounds of structure 43 can be alkylated in presence of base such as NaH solvents such as DMF or THF at about rt, using standard alkylating agents such as 1-bromoethane (Scheme 9, Step d).

Scheme 9

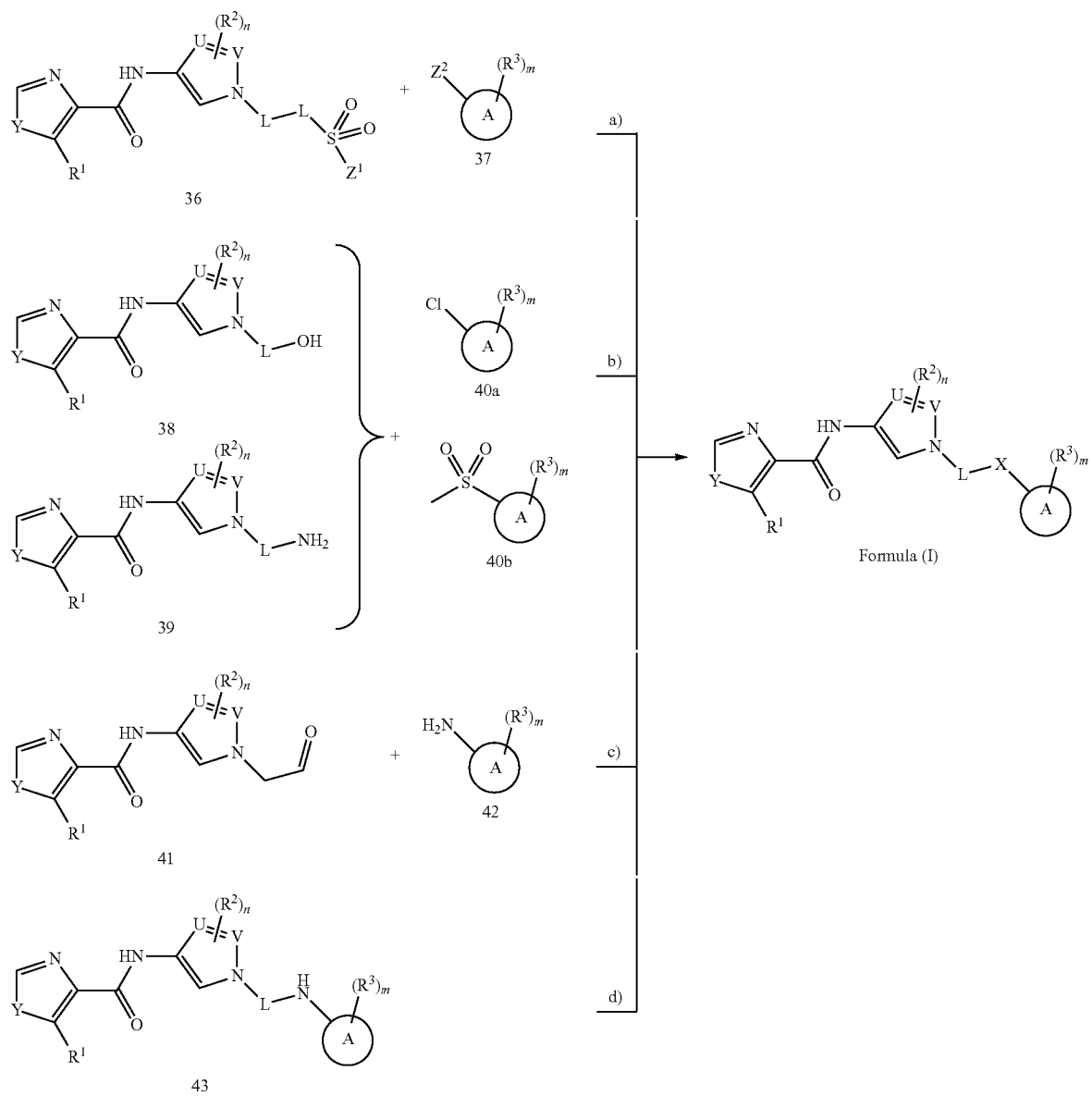

Compounds of structure 36 and 38 may be synthesized as described in Scheme 10. Reduction of the nitro group of compound 15 (Scheme 4) using the methods described above leads to amines 44 which can be coupled with the corresponding carboxylic acids of structure 1 using standard amide coupling conditions. Compounds of structure 38 can be converted to intermediates of structure 36 in presence of sulfonyl-chloride and a base such as Et$_3$N, DIPEA or DMAP, in suitable solvents such as DCM at about 0° C. to 80° C.

Scheme 10: Synthesis of compounds of structure 38 and 36

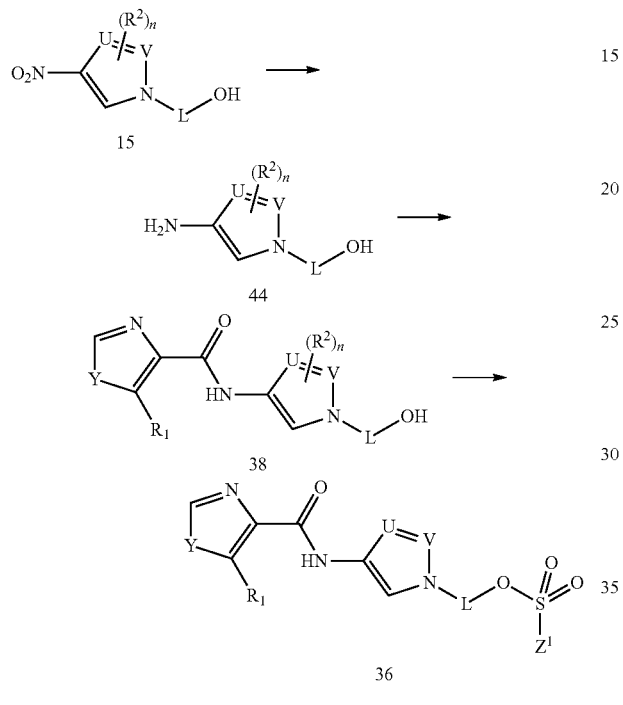

Compounds of structure 37, 40a, 40b or 42 are either commercially available or synthesized according to well known literature procedures (see for example experimental section).

Compounds of structure 39 may be synthesized according to scheme 11. Reduction of the nitro group of compounds of structure 17 (scheme 4) using the methods described above leads to amines of structure 45 which can be coupled with the corresponding carboxylic acids of structure 1 using standard amide coupling conditions. Compounds of structure 46 can be converted to compounds of structure 39 by Boc-removal under standard acidic conditions.

Scheme 11: Synthesis of compounds of structure 39

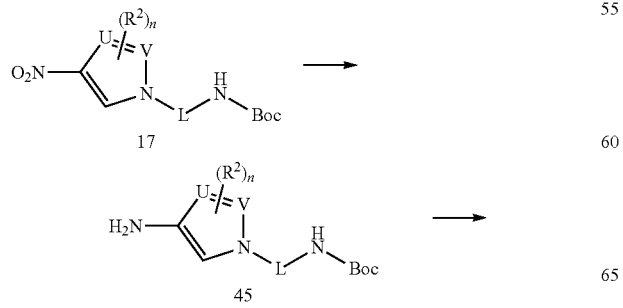

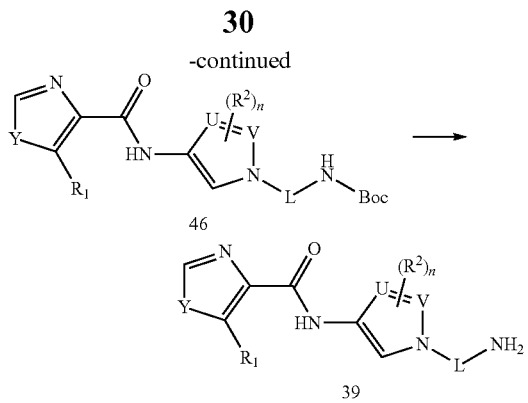

Compounds of structure 41 can be prepared according to Scheme 12, by reduction of the nitro-group using the methods described above to obtain amines of structure 47 which can be coupled with the corresponding carboxylic acids of structure 1 using standard amide coupling conditions. Compounds of structure 48 can be converted to compounds of structure 41 by acetal deprotection under standard conditions, such as hydrochloric acid in solvents such as THF, dioxane at about 80° C.

Scheme 12: Synthesis of compounds of structure 41

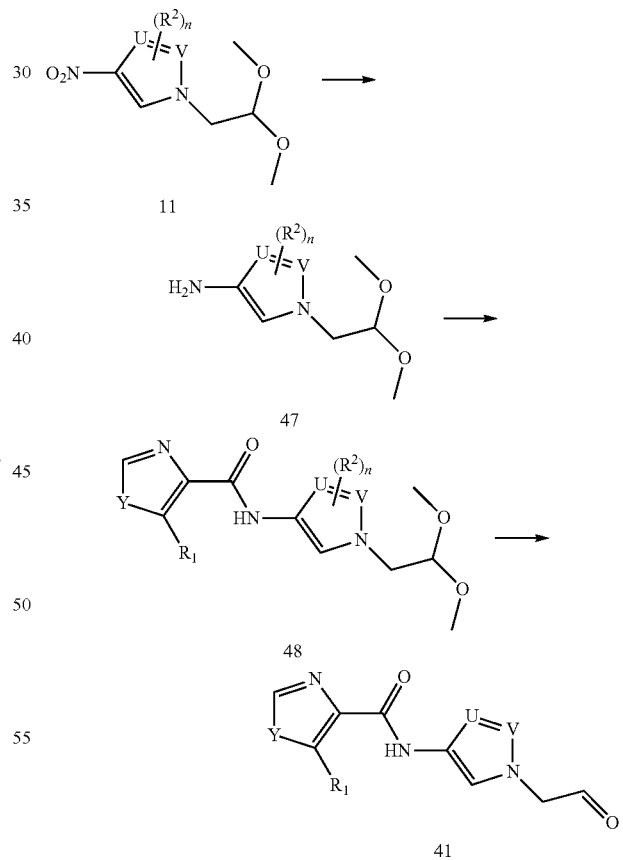

EXPERIMENTAL PART

Abbreviations (as used herein and in the description above)
Ac acetyl
AcOH acetic acid aq. aqueous
atm atmosphere
BSA bovine serum albumin
ca. about
cat. catalytic
DIPEA diisopropylethylamine
DiBAL di-iso-butylaluminum hydride
DMAP 4-N,N-dimethylaminopyridine
DMF dimethylformamide
DMSO dimethylsulfoxide
DPPA diphenylphosphoryl azide
EtOAc ethyl acetate
EIA enzyme immunoassay
EDC N-(3-dimethylaminopropyl)-W-ethyl-carbodiimide hydrochloride
ELSD evaporative light-scattering detection
eq. equivalent(s)
ES+ electro-spray, positive ionization
Et ethyl
ether diethylether
Et$_3$N triethylamine
EtOH ethanol
FC flash column chromatography on silica gel
h hour(s)
HATU 2-(7-aza-1H-benzotriazol-1-yl)-1,1,3,3-tetramethyluronium hexafluorophosphate
HBTU 0-(benzotriazol-1-yl)-N,N,N',N'-tetramethyluronium hexafluorophosphate
hept heptane
hex hexane
HOAt 1-hydroxy-7-azabenzotriazole
HOBt hydroxybenzotriazole
HPLC high performance liquid chromatography
inorg. inorganic
LC-MS liquid chromatography mass spectrometry
m meta
m-CPBA meta-chloroperbenzoic acid
Me methyl
MeCN acetonitrile
MeI methyliodine
MeOH methanol
min minute(s)
MS mass spectrometry
Ms methanesulfonyl
NaOMe sodiummethoxide
NMO N-Methyl-morpholine-N-oxide
NMP N-Methyl-2-pyrrolidinone
NMR nuclear magnetic resonance
OAc acetate
org. organic
p para
prep. preparative
p-TsOH para-toluene sulfonic acid
PL-DETA diethylenetriamine resin
PL-HCO$_3$ resin bound hydrogen carbonate
PPh$_3$ triphenylphosphine
PyBOP benzotriazol-1-yl-oxy-tris-pyrrolidino-phosphonium-hexafluoro-phosphate
Rf retention factor
rt room temperature
sat. saturated
Si-DCC silicabond carbodiimide
sol. solution
STAB sodium triacetoxyborohydride
TBTU O-(benzotriazol-1-yl)-N,N,N',N'-tetramethyluronium tetrafluoroborate
TFA trifluoroacetic acid
THF tetrahydrofuran
TLC thin layer chromatography
TPAP tetrapropylammonium perruthenate
$t_R$ retention time
TsOH p-toluene sulfonic acid monohydrate
UV ultra violet
V is visible I Chemistry The following examples illustrate the preparation of biologically active compounds of the invention but do not at all limit the scope thereof.

All temperatures are stated in degrees Celsius (° C.). Unless otherwise indicated, the reactions take place at rt. Reactions were carried out under Ar or $N_2$ using anhydrous solvents of commercial grade.

Automated Microwave Syntheziser:
Emrys™ Optimizer from Personal Chemistry AB (now Biotage AB)

Chromatography:
Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm): elution with EtOAc, hept, hex, DCM, MeOH or mixtures thereof.

Intermediates are Characterized by:
LC-MS with Acidic Conditions
Method A:
Agilent 1100 series with mass spectrometry detection (MS: Finnigan single quadrupole). Column: Zorbax SB-AQ (3.5 μm, 4.6×50 mm). Conditions: MeCN [eluent A]; water+0.04% TFA [eluent B]. Gradient: 95% B→5% B over 1.5 min. (flow: 4.5 mL/min.). Detection: UV/Vis+MS. $t_R$ is given in min.

Method B:
Agilent 1100 series with mass spectrometry detection (MS: Finnigan single quadrupole). Column: Waters XBridge C18 (5 μm, 4.6×50 mm). Conditions: MeCN [eluent A]; water+0.04% TFA [eluent B]. Gradient: 95% B→5% B over 1.5 min. (flow: 4.5 mL/min.). Detection: UV/Vis+MS. $t_R$ is given in min.

LC-MS with Basic Conditions
Method C:
Agilent 1100 series with mass spectrometry detection (MS: Finnigan single quadrupole). Column: Waters XBridge C18 (5 μm, 4.6×50 mm). Conditions: MeCN [eluent A]; 13 mmol/L $NH_3$ in water [eluent B]. Gradient: 95% B→5% B over 1.5 min. (flow: 4.5 mL/min.). Detection: UV/Vis+MS. $t_R$ is given in min.

Final Compounds are Characterized by:
Method D:
LC-MS-conditions: Analytical. Pump: Waters Acquity Binary, Solvent Manager, MS: Waters SQ Detector, DAD: Acquity UPLC PDA Detector, ELSD: Acquity UPLC ELSD. Column: Acquity UPLC BEH C18 1.7 mm 2.1×50 mm from Waters, thermostated in the Acquity UPLC Column Manager at 50° C. Eluents: A1: $H_2O$+0.05% FA; B1: MeCN+0.05% FA; A2: $H_2O$+0.05% TFA; B2: MeCN+0.05% TFA. Method: Gradient: 2% B→98% B over 1.5 min. Flow: 1.2 mL/min. Detection: UV 214 nm and ELSD, and MS, $t_R$ is given in min.

HPLC Preparative (Basic):

X-Bridge C18 5 μm, 50×19 mm ID from Waters. Eluents: A: H₂O+0.5% NH₄OH; B: MeCN; Gradient: 10% B→90% B over 5 min. Flow: 40.0 mL/min. Detection: UV/Vis and/or ELSD.

NMR Spectroscopy:

Bruker Avance 400 (400 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the preparation of biologically active compounds of the invention but do not at all limit the scope thereof.

General Procedures:

General Procedure a: Amide Coupling (1):

In a glass vial, to an acid (1.5 eq.) in DCM (0.18 M) was added TBTU (2.0 eq.) and DIPEA (3.0 eq.) and the reaction mixture was stirred for 30 min at rt before the amine (1.0 eq.) was added (either as a solid or dissolved in minimal amount of DCM). The reaction mixture was stirred for 3-24 h at rt. The reaction mixture was diluted with DCM and washed with H₂O (2×). The combined aq. layers were reextracted with DCM or EtOAc and the combined org. layers were dried (MgSO₄), filtered and the solvent removed under reduced pressure. The residue was purified by FC or prep. HPLC to yield the desired compound.

General Procedure B: Amide Coupling (2)

In a glass vial, to an acid (1.5 eq., 0.15 mmol) in DCM/DMF (1:1, 0.38 M) was added HOAt (0.5 eq, 1 M solution in DMF) and Si-DCC (2.0 eq.). After shacking for 5 minutes, amine (1.0 eq.) in DMF/DCM (1:1, 0.25 M solution) was added and the reaction mixture was shaken for 18 h at rt. To the reaction mixture was added 1 mL DCM/DMF (1:1) followed by the addition of PL-DETA and PL-HCO₃-resin and the mixture was stirred for 3 days. The reaction mixture was diluted with MeOH, the resins (Si-DCC, PL-DETA and PL-HCO₃) filtered off, washed with 2 mL DCM/MeOH (1:1) and the solvents were removed by reduced pressure. Purification of the residue was performed by prep. HPLC to yield the desired compound.

General Procedure C: Alkylation (1)

In a microwave vial, to an amine (1.0 eq.) in acetonitrile (0.3 M) was added Cs₂CO₃ (2.0 eq.) and the bromo-analog (1.1 eq.) as a solution in minimal amount of DMF. The reaction mixture was irradiated in the microwave for 40 min to 110° C. (cooling function on). The reaction mixture was diluted with 1N aq. HCl-solution and DCM. The org. layer was separated and the aq. layer extracted with DCM (2×). The combined org. layers were washed with brine, dried (MgSO₄) filtered and the solvent was removed under reduced pressure. The residue was purified by FC or prep. HPLC to yield the desired compound.

General Procedure D: Alkylation (2)

A flask was charged with amine (1.0 eq.), methyl-sulfonyl-analog (1.0 eq.), Cs₂CO₃ (2.0 eq.) and DMF (0.8 M). The resulting reaction mixture was stirred at 65° C. for 18 h. The reaction mixture was filtered and directly purified by FC or prep. HPLC to yield the desired compound.

General Procedure E: Nucleophilic Substitution

To a solution of nucleophile (1.0 eq.) in DMF (0.2 M) was added NaH (1.0 eq.) and stirred for 30 min at rt. To the suspension was added sulfonyl-derivative (1.0 eq.) in DMF (2.5 M) and the resulting mixture was stirred at rt for 1-3 h. After addition of H₂O, the reaction mixture was acidified with 1N aq. HCl-solution and extracted with DCM or EtOAc (3×). The combined org. layers were washed with brine, dried (MgSO₄) filtered and the solvent removed under reduced pressure. The residue was purified by FC or prep. HPLC to yield the desired compound.

General Procedure F: N-Arylation (1)

To a flask was added amine (1.0 eq.), o-xylene (0.25 M), the appropriate 2-chloro-heteroaryl-derivative (1.0 eq.), K₂CO₃ (3.0 eq.) and DIPEA (3.0 eq.). This suspension was stirred in a sealed flask at 145° C. for 1-3 days. The reaction mixture was diluted with EtOAc and water, then the org. layer was separated and the aq. layer was extracted with EtOAc (2×). The combined org. layers were dried (MgSO₄), filtered and the solvent was removed under reduced pressure. The residue was purified by FC or prep. HPLC to yield the desired compound.

General Procedure G: N-Arylation (2)

In a microwave vial, to an amine (1.0 eq.) in MeCN (0.15 M) was added the appropriate 2-chloro-heteroaryl-derivative (1.0 eq.) and DIPEA (2.5 eq.) The resulting mixture was heated in the microwave at 180° C. for 1 h. The mixture was purified by FC or prep. HPLC to yield the desired compound.

General Procedure H: N-Arylation (3)

In a microwave vial, to an amine (1.0 eq.) in MeCN (0.15 M) was added the appropriate 2-chloro-heteroaryl-derivative (1.0 eq.) and DIPEA (2.5 eq.) followed by NMP (0.03 M). The resulting mixture was heated in the microwave at 150-180° C. for 10 min to 1 h. The mixture was directly purified by FC or prep. HPLC to yield the desired compound.

General Procedure I: N-Arylation (4)

To a flask was added amine (1.0 eq.), o-xylene (0.25 M), 2-methyl-sulfonyl-pyrimidine derivative (1.0 eq.), K₂CO₃ (3.0 eq.) and DIPEA (3.0 eq.). This suspension was stirred in a sealed flask at 145° C. for 1 to 3 days. The reaction mixture was diluted with EtOAc and water, then the org. layer was separated and the aq. layer was extracted with EtOAc (2×). The combined org. layers were dried (MgSO₄), filtered and the solvent was removed under reduced pressure. The residue was purified by FC or prep. HPLC to yield the desired compound.

General Procedure J: O-Arylation

To a solution of alcohol (1.0 eq.) in THF (0.16 M) was added NaH (1.1 eq.) and stirred at rt for 30 min. To the suspension was added the appropriate 2-chloro-heteroaryl derivative (1.1 eq.) and the resulting mixture was stirred at rt overnight. The mixture was quenched with water and the solvent was removed in vacuo. The aq. layer was extracted with DCM (2×) and the combined org. layers were washed with brine, dried (MgSO₄), filtered and the solvent was removed under reduced pressure. The residue was purified by FC or prep. HPLC to yield the desired compound.

Synthesis of Intermediates 5-(3-(pyrrolidin-1-yl)phenyl)oxazole-4-carboxylic acid Step 1:

To a suspension of 3-(pyrrolidin-1-yl)benzoic acid (1.0 g, 5.23 mmol) and K₂CO₃ 1.75 g (12.55 mmol) in DMF (10.8 ml) was added methyl isocyanoacetate (551 mg, 5.23 mmol) in DMF (6.8 mL). The resulting mixture was stirred at rt for 5 min and then cooled to 0° C. A solution of DPPA (1.13 mL, 5.23 mmol) in DMF (6.8 mL) was added dropwise. The resulting mixture was stirred at 0° C. for 2 h and then at rt overnight. It was then diluted with toluene-EtOAc 1:1 (110 mL) and the organic layer was washed with water (55 mL) and aq. sat. NaHCO₃-solution (45 mL), dried (MgSO₄), filtered and concentrated to dryness. The residue was purified by FC (DCM/MeOH 9:1; Rf=0.41) to afford methyl 5-(3-(pyrrolidin-1-yl)phenyl)oxazole-4-carboxylate as a orange oil. LC-MS conditions A: $t_R$=0.93 min, [M+H]+=273.04.

Step 2:
To a stirred solution of methyl 5-(3-(pyrrolidin-1-yl)phenyl)oxazole-4-carboxylate (625 mg, 2.3 mmol) in THF (223 mL) was added 1N aq. NaOH-solution (11 mL) and the resulting mixture was stirred at rt overnight. The reaction mixture was poured in 1N aq. HCl-solution and extracted with EtOAc (75 mL). The organic layer was dried (MgSO$_4$), filtered and concentrated to dryness to afford the title compound as a white solid. LC-MS conditions A: $t_R$=0.78 min, [M+H]+=259.00

5-(3-morpholinophenyl)oxazole-4-carboxylic acid

Step 1:
To a suspension of 3-morpholin-4-ylbenzoic acid (1.0 g, 4.83 mmol) in toluene (8.5 mL), DMF (3 drops) and oxayl chloride (0.66 mL, 7.24 mmol) was added. To the resulting mixture was added toluene (1 mL) and Et$_3$N (1.5 mL). The reaction mixture was stirred for 30 min and the solvent was removed under reduced pressure.

Step 2:
To a solution of methyl isocyanoacetate (0.53 mL, 4.83 mmol) in THF (4.5 mL), DMAP (59.9 mg, 0.483 mmol) and Et$_3$N (1.48 mL, 10.63 mmol) was added. The reaction mixture was heated to 60° C. and the above obtained residue, dissolved in THF (10 mL), was added. After 1.5 h at 75° C., the reaction mixture was allowed to reach rt and water was added. The inorg. layer was extracted with tert. Butylmethylether (3×). The combined org. phases were washed with H$_2$O and sat. aq. NaHCO$_3$-solution, dried (MgSO$_4$), filtered and the solvent was removed under reduced pressure. FC purification (EtOAc/hept 1:1; Rf=0.21) yielded methyl 5-(3-morpholinophenyl)oxazole-4-carboxylate as an orange solid which was used without further purification. LC-MS conditions A: $t_R$=0.90 min, [M+H]+=303.82.

Step 3:
To a stirred solution of 5-(3-morpholinophenyl)oxazole-4-carboxylate (900 mg, 2.98 mmol) in THF (29 mL) was added 1N aq. NaOH-solution (14 mL) and the resulting mixture was stirred at rt overnight. The reaction mixture was poured into 1N aq. HCl-solution and extracted with EtOAc (85 mL). The org. layer was dried (MgSO$_4$), filtered and concentrated to dryness to afford the title compound as a yellow solid which was used without further purification. LC-MS conditions A: $t_R$=0.70 min, [M+H]+=274.99.

5-(pyrimidin-4-yl)oxazole-4-carboxylic acid

Step 1:
To a solution of pyrimidine-4-carboxylic acid (261 mg, 2.00 mmol) and DIPEA (0.52 mL, 2.96 mmol) in DMF (8 mL) was added methyl isocyanoacetate (0.28 mL, 2.93 mmol) at rt. The resulting yellow solution was stirred at rt for 5 min and cooled to 0° C. DPPA (0.54 mL, 2.43 mmol) was then added and the resulting solution was stirred at 0° C. for 1 h and at rt for 30 min. Aq. sat. NaHCO$_3$-solution was added and the mixture extracted with EtOAc (4×). The combined organic extracts were dried (Na$_2$SO$_4$), filtered and concentrated in vacuo. Purification by FC (hept/EtOAc 9:1 to 100% EtOAc) yielded methyl 5-(pyrimidin-4-yl)oxazole-4-carboxylate. LC-MS conditions A: $t_R$=0.68 min, [M+H]+=206.43.

Step 2:
A solution of methyl 5-(pyrimidin-4-yl)oxazole-4-carboxylate (179 mg, 0.80 mmol) in THF/H$_2$O (1:1, 6 mL) was treated with LiOH (60 mg, 1.43 mmol) at 0° C. The reaction mixture was stirred at 0° C. for 15 min, then diluted with EtOAc and 1N aq. HCl-solution was added (to reach pH=1). The layers were separated and the aq. layer extracted with EtOAc (2×), EtOAc/MeOH 4:1 then DCM/MeOH 4:1. The combined organic extracts were dried (Na$_2$SO$_4$), filtered and concentrated in vacuo to obtain the title compound as a solid which was used without further purification. LC-MS conditions A: $t_R$=0.56 min, [M+H]+=192.47.

1-[2-(2-Methyl-benzoimidazol-1-yl)-ethyl]-1H-pyrazol-4-ylamine

Step 1:
To a solution of 2-methyl-1H-benzimidazole (3.50 g, 25.95 mmol) in DMF (70.0 mL), Cs$_2$CO$_3$ (12.08 g, 36.33 mmol) and 2-bromoethanol (2.5 mL, 34.15 mmol) was added. After stirring at 150° C. for 1 h, the reaction mixture was allowed to reach rt and was diluted with EtOAc. The org. layer was separated and the aq. layer was extracted with EtOAc (5×). The combined org. layers were washed with brine, dried (MgSO$_4$), filtered and the solvent was removed under reduced pressure to yield 2-(2-methyl-1H-benzoimidazol-1-yl)ethanol which was used in the next step without further purification. LC-MS conditions B: $t_R$=0.25 min, [M+H]+=177.17.

Step 2:
To a solution of 2-(2-methyl-1H-benzoimidazol-1-yl)ethanol (4.00 g, 22.70 mmol) in DCM (80 mL) at 0° C., thionylchloride (3.5 mL, 48.25 mmol) was added. The reaction mixture was allowed to warm to rt and stirred for 5 h at this temperature, then the reaction mixture was quenched with aq. sat. NaHCO$_3$-solution (gas evolution) and extracted with DCM (3×). The org. layers was dried (MgSO$_4$), filtered and the solvent was removed under reduced pressure to yield 1-(2-chloroethyl)-2-methyl-1H-benzoimidazole which was used without further prufication in the next step. LC-MS conditions B: $t_R$=0.37 min, [M+H]+=195.09.

Step 3:
To 1-(2-chloroethyl)-2-methyl-1H-benzoimidazole) (4.42 g, 22.71 mmol), in MeCN (50 mL), 4-nitro-1H-pyrazole (2.57 g, 22.71 mmol) and Cs$_2$CO$_3$ (8.14 g, 24.98 mmol) was added. After stirring at 80° C. for 18 h the reaction mixture was allowed to reach rt and filtered. The filter cake was washed with DCM and the filtrate was concentrated in vacuo, then the residue was dissolved in DCM and washed with H$_2$O. The combined aq. layers were reextracted with DCM, the combined org. layers were dried (MgSO$_4$), filtered and the solvent removed under reduced pressure to yield 2-methyl-1-(2-(4-nitro-1H-pyrazol-1-yl)-ethyl)-1H-benzoimidazole, which is used in the next step without further purification. LC-MS conditions B: $t_R$=0.42 min, [M+H]+=272.07.

Step 4:
To a round bottom flask was added 2-methyl-1-(2-(4-nitro-1H-pyrazol-1-yl)-ethyl)-1H-benzoimidazole (5.23 g, 19.28 mmol), Pd/C (523 mg) and MeOH (100 mL, degassed). The flask was evacuated and backfilled with H$_2$ and the reaction mixture was stirred under H$_2$-atmosphere at rt for 5 h. The reaction mixture was filtered over celite, washed with MeOH and the solvent was removed under reduced pressure. Purification was performed by dissolving the desired compound at 40° C. in DCM (60 mL) and filtering off the insoluble impurities. By adding heptane (150 mL) to the remaining solution, the title compound precipitated out as a pink solid. LC-MS conditions B: $t_R$=0.17 min, [M+H]+=242.00.

1-(2-Phenoxy-ethyl)-H-pyrazol-4-ylamine

Step 1:
To 4-nitro-1H-pyrazole (220 mg, 1.95 mmol) in acetonitrile (10 mL), $Cs_2CO_3$ (697 mg, 2.14 mmol) and (2-bromoethoxy)benzene (439 mg, 2.14 mmol) was added. The resulting mixture was refluxed (80° C.) for 40 min and then let stir at rt overnight. The reaction mixture was filtered, the filter cake washed with DCM and the filtrate concentrated in vacuo to obtain 4-nitro-1-(2-phenoxyethyl)-1H-pyrazole as a crude solid which was used without further purification. LC-MS conditions A: $t_R$=0.85 min, [M+H]+=no ionization.
Step 2:
To a solution of 4-nitro-1-(2-phenoxyethyl)-1H-pyrazole (444 mg, 1.9 mmol), in EtOAc (1.8 mL, degassed) and EtOH (5.4 mL, degassed), $PtO_2$ (39.0 mg, 0.17 mmol) was added and the reaction mixture was stirred at rt under a $H_2$-atmosphere for 18 h. The mixture was diluted with EtOH, filtered over celite and the filter cake was rinsed with EtOH. The filtrate was concentrated to obtain the desired compound as a pale purple oil. LC-MS conditions A: $t_R$=0.53 min, [M+H]+= 234.41.

1-[2-(3-Fluoro-phenyl)-ethyl]-1H-pyrazol-4-ylamine

Step 1:
To a solution of 4-nitro-1H-pyrazole (450 mg, 3.86 mmol) in acetone (15 mL), 3-fluorophenethyl bromide (784 mg, 3.86 mmol), $K_2CO_3$ (2.68 g, 19.301 mmol) and tetrabutylammonium bromide (120 mg, 0.38 mmol) was added. The white suspension was stirred at rt for 2 h, then the reaction mixture was diluted with $H_2O$ and EtOAc. The org. layer was separated and the aq. layer was extracted with EtOAc (1×). The combined org. layers were dried ($MgSO_4$), filtered and the solvent was removed under reduced pressure. Purification of by FC (EtOAc/hept 3:7) gave 1-(3-fluorophenethyl)-4-nitro-1H-pyrazole as a off-white solid. LC-MS conditions B: $t_R$=0.75 min, [M+H]+=no ionization.
Step 2:
To a round bottom flask 1-(3-fluorophenethyl)-4-nitro-1H-pyrazole (785 mg, 3.34 mmol), Pd/C (79 mg) and MeOH (10.0 mL, degassed) was added. The flask was evacuated and backfilled with $H_2$ and the reaction mixture was stirred under $H_2$-atmosphere at rt for 18 h. The reaction mixture was filtered over celite, washed with MeOH and the solvent was removed under reduced pressure to yield 1-[2-(3-Fluoro-phenyl)-ethyl]-1H-pyrazol-4-ylamine as a red oil which was used without further purification. LC-MS conditions B: $t_R$=0.41 min; [M+MeCN+H]$^+$=247.32.

1-Phenethyl-1H-pyrazol-4-ylamine

Step 1:
To a solution of 4-nitro-1H-pyrazole (1.50 g, 12.87 mmol) in MeCN (30 mL), (2-bromoethyl)benzene (1.97 mL, 14.15 mmol) and $Cs_2CO_3$ (4.61 g, 14.15 mmol) was added. The resulting mixture was refluxed (80° C.) for 1.5 h, then the reaction mixture was allowed to reach rt. The mixture was diluted with DCM, filtered, the filter cake was washed with DCM and the filtrate was concentrated in vacuo to obtain 4-nitro-1-phenethyl-1H-pyrazole as a beige solid which was used in the next step without further purification. LC-MS conditions A: $t_R$=0.92 min; [M+H]$^+$=217.97.

Step 2:
To a solution of 4-nitro-1-phenethyl-1H-pyrazole (2.78 g, 12.87 mmol), in EtOAc (6 mL, degassed) and EtOH (18 mL, degassed), $PtO_2$ (235 mg, 1.2 mmol) was added and the reaction mixture was stirred at rt under a $H_2$-atmosphere for 18 h. The mixture was diluted with EtOH, filtered over celite and the filter cake was rinsed with EtOH. The filtrate was concentrated to obtain the title compound I-phenethyl-1H-pyrazol-4-ylamine as red solid. LC-MS conditions A: $t_R$=0.54 min, [M+MeCN+H]$^+$=229.04.

1-[2-(3-Methoxy-phenyl)-ethyl]-1H-pyrazol-4-ylamine

Step 1:
To a solution of 4-nitro-1H-pyrazole (230 mg, 2.03 mmol) in MeCN (9.5 mL), 1-(2-bromo-ethyl)-3-methoxy-benzene (481 mg, 2.24 mmol) dissolved in MeCN (1.5 mL) and $Cs_2CO_3$ (729 mg, 2.24 mmol) was added. The resulting mixture was refluxed (80° C.) for 1.5 h, then the reaction mixture was allowed to reach rt. The mixture was diluted with DCM, filtered, the filter cake was washed with DCM and the filtrate was concentrated in vacuo to obtain 1-(3-methoxyphenethyl)-4-nitro-1H-pyrazole as a beige solid which was used in the next step without further purification. LC-MS conditions A: $t_R$=0.86 min, [M+H]$^+$=no ionization.
Step 2:
To a solution of 1-(3-methoxyphenethyl)-4-nitro-1H-pyrazole (2.03 mmol) in EtOAc (2 mL, degassed) and EtOH (6 mL, degassed), $PtO_2$ (45 mg, 0.20 mmol) was added and the reaction mixture was stirred at rt under a $H_2$-atmosphere for 3 h. The mixture was diluted with EtOH, filtered over celite and the filter cake was rinsed with EtOH. The filtrate was concentrated to obtain the title compound as red oil. LC-MS conditions A: $t_R$=0.52 min, [M+H]$^+$=218.42.

1-[2-(3-Methoxy-phenoxy)-ethyl]-1H-pyrazol-4-ylamine

Step 1:
To a solution of 4-nitro-1H-pyrazole (220 mg, 1.90 mmol) in MeCN (9.5 mL), 1-(2-bromoethoxy)-3-methoxybenzene (495 mg, 2.14 mmol) dissolved in MeCN (1.5 mL) and $Cs_2CO_3$ (697 mg, 2.14 mmol) was added. The resulting mixture was refluxed (80° C.) for 1.5 h, then the reaction mixture was allowed to reach rt. The mixture was diluted with DCM, filtered, the filter cake was washed with DCM and the filtrate was concentrated in vacuo to obtain 1-(2-(3-methoxyphenoxy)ethyl)-4-nitro-1H-pyrazole which was used in the next step without further purification. LC-MS conditions A: $t_R$=0.85 min, [M+H]$^+$=no ionization.
Step 2:
To a solution of 1-(2-(3-methoxyphenoxy)ethyl)-4-nitro-1H-pyrazole (533 mg, 1.90 mmol), in EtOAc (2 mL, degassed) and EtOH (6 mL, degassed), $PtO_2$ (42 mg, 0.19 mmol) was added and the reaction mixture was stirred at rt under a $H_2$-atmosphere for 3 h. The mixture was diluted with EtOH, filtered over celite and the filter cake was rinsed with EtOH. The filtrate was concentrated to obtain the title compound as a pale brown oil. LC-MS conditions A: $t_R$=0.53 min, [M+H]$^+$=234.41.

1-[2-(4,6-Dimethoxy-pyrimidin-2-yloxy)-ethyl]-1H-pyrazol-4-ylamine

Step 1:
To a solution of 4-nitro-1H-pyrazole (6.09 g, 52.20 mmol) in MeCN (80 mL), $Cs_2CO_3$ (18.71 g, 57.42 mmol) and 2-bromoethanol (4.59 mL, 62.64 mmol) was added. The resulting mixture was refluxed (80° C.) for 3.5 h, then the reaction mixture was allowed to reach rt. The mixture was diluted with DCM, filtered, the filter cake was washed with DCM and the filtrate was concentrated in vacuo. The residue was partitionned between water and EtOAc, the org. layer was separated and the aq. layer was extracted with EtOAc (1×). The combined org. layers were washed with brine, dried (MgSO$_4$), filtered and concentrated in vacuo. Purification was performed by FC (EtOAc/hept 7:3 to EtOAc/MeOH 9:1) to obtain 2-(4-nitro-1H-pyrazol-1-yl)ethanol as a white solid. LC-MS conditions A: $t_R$=0.44 min, [M+H]$^+$=no ionization.

Step 2:

To an ice-cooled solution of 2-(4-nitro-1H-pyrazol-1-yl)ethanol (1.90 g, 12.02 mmol) in THF (60 mL), NaH (673 mg, 16.82 mmol, 60%) was added and the solution was stirred for 5 min at 0° C., then the ice bath was removed and the reaction mixture was stirred at rt for 30 min, before 2-chloro-4,6-dimethoxypyrimidine (2.31 g, 13.22 mmol) was added. After 40 min at rt, the reaction mixture was quenched with water and the org. solvent was removed in vacuo. The aq. layer was extracted with DCM (1×), then acidified with 1 N HCl-solution to pH 2, and extracted with DCM (2×). The combined org. layers were washed with brine, dried (MgSO$_4$), filtered and the solvent removed under reduced pressure. Purification by crystallization (DCM-hept-mixture) yielded 4,6-dimethoxy-2-(2-(4-nitro-1H-pyrazol-1-yl)ethoxy)pyrimidine as a beige solid. LC-MS conditions A: $t_R$=0.88 min, [M+H]$^+$=295.98.

Step 3:

To a solution of 4,6-dimethoxy-2-(2-(4-nitro-1H-pyrazol-1-yl)ethoxy)pyrimidine (2.05 g, 6.93 mmol), in EtOAc (3.0 mL, degassed) and EtOH (9 mL, degassed), PtO$_2$ (135 mg, 0.70 mmol) was added and the reaction mixture was stirred at rt under a H$_2$-atmosphere for 3 h. The mixture was diluted with EtOH, filtered over celite and the filter cake was rinsed with EtOH. The filtrate was concentrated to obtain the title compound as a red oil. LC-MS conditions A: $t_R$=0.58 min, [M+H]$^+$=266.02.

1-[2-(5,6-Dimethoxy-indol-1-yl)-ethyl]-1H-pyrazol-4-ylamine

Step 1:

To a solution of 5,6-dimethoxyindole (2.00 g, 11.29 mmol) in acetic acid (120 mL), sodium cyanoborohydride (2.13 g, 33.86 mmol) was added in portions (slightly exothermic). After stirring at rt for 1 h, DCM was added and the org. layer was washed with sat. NaHCO$_3$-solution and brine. The org. layer was dried (MgSO$_4$), filtered and the solvent was removed under reduced pressure to yield 5,6-dimethoxyindoline as a brown solid, which was stored in the freezer until it was used in step 4. LC-MS conditions B: $t_R$=0.28 min, [M+H]$^+$=180.23.

Step 2:

To a solution of 4-nitro-1H-pyrazole (1.50 g, 13.27 mmol) in MeCN (30 mL), 2-bromo-1,1-dimethoxyethane (2.34 mL, 19.90 mmol) and Cs$_2$CO$_3$ (6.48 g, 19.90 mmol) was added. The resulting mixture was refluxed (85° C.) for 20 h, then the reaction mixture was allowed to reach rt. The mixture was diluted with DCM, filtered, the filter cake was washed with DCM and the filtrate was concentrated in vacuo. The residue was partitioned between water and DCM, then the aq. layer was extracted with DCM (2×) and the comb. org. layers were dried (MgSO$_4$), filtered and the solvent was removed under reduced pressure to yield 1-(2,2-dimethoxyethyl)-4-nitro-1H-pyrazole as a yellow oil which was used in the next step without further purification. LC-MS conditions B: $t_R$=0.50 min, [M+H]$^+$=no ionization.

Step 3:

To a solution of 1-(2,2-dimethoxyethyl)-4-nitro-1H-pyrazole (2.65 g, 13.2 mmol) in THF (34 mL), a 2N aq. HCl-solution (60 mL, 120 mmol) was added dropwise. After stirring at 80° C. for 2 h, the reaction mixture was allowed to reach rt and freeze-dried overnight to yield 2-(4-nitro-1H-pyrazol-1-yl)acetaldehyde which was used as an yellow oil in the next step without further purification. LC-MS conditions B: $t_R$=0.24 min, [M+H]$^+$=no ionization.

Step 4:

To a solution of 2-(4-nitro-1H-pyrazol-1-yl)acetaldehyde (942 mg, 6.08 mmol) in DCM (60.0 mL), 5,6-dimethoxyindoline (from step 1) (1.09 g, 6.08 mmol) and STAB (1.55 g, 7.29 mmol) was added. After stirring at rt for 1 h, the reaction mixture was quenched with water and extracted with DCM (2×). The combined org. layers were concentrated and purification was performed by FC (EtOAc/hex 1:4 to 1:1) to yield 5,6-dimethoxy-1-(2-(4-nitro-1H-pyrazol-1-yl)ethyl)indoline as a brown solid. LC-MS conditions B: $t_R$=0.65 min, [M+H]$^+$=319.19.

Step 5:

To a solution of 5,6-dimethoxy-1-(2-(4-nitro-1H-pyrazol-1-yl)ethyl)indoline (1.53 g, 4.81 mmol) in MeOH (50 mL), PtO$_2$ (200 mg, 0.88 mmol) was added and the reaction mixture was stirred at rt under a H$_2$-atmosphere for 1 h. The mixture was diluted with EtOH, filtered over celite and the filter cake was rinsed with MeOH. The filtrate was concentrated under reduced pressure to obtain 1-(2-(5,6-dimethoxyindolin-1-yl)ethyl)-1H-pyrazol-4-amine as a brown oil, which was used in the next step without further purification. LC-MS conditions B: $t_R$=0.38 min, [M+H]$^+$=289.18.

Step 6:

A solution of 1-(2-(5,6-dimethoxyindolin-1-yl)ethyl)-1H-pyrazol-4-amine (1.36 g, 4.70 mmol) in acetone (10 mL) was added dropwise to a suspension of MnO$_2$ (817 mg, 9.41 mmol) in aceton (10 mL). The resulting dark reaction mixture was stirred at rt overnight, then filtered over celite, washed with acetone and the filtrate was concentrated under reduced pressure. Purification was performed by FC (DCM/MeOH 98:2→95:5) to yield the title compound as a brown oil. LC-MS conditions B: $t_R$=0.41 min, [M+H]$^+$=287.18.

1-[3-(2,3-Dihydro-indol-1-yl)-propyl]-1H-pyrazol-4-ylamine

Step 1:

To a solution of 4-nitro-1H-pyrazole (4.50 g, 39.80 mmol) in MeCN (135 mL), 3-bromo-1,1-dimethoxypropane (7.25 mL, 47.76 mmol) and Cs$_2$CO$_3$ (16.30 g, 50.0 mmol) was added. The resulting mixture was refluxed (80° C.) for 1.5 h and allowed to reach rt overnight. The mixture was diluted with DCM, filtered, the filter cake was washed with DCM and the filtrate was concentrated in vacuo. The residue was partitioned between brine and EtOAc, then the org. layer was separated and the aq. layer was extracted with EtOAc (2×). The comb. org. layers were dried (MgSO$_4$), filtered and the solvent was removed under reduced pressure to yield 1-(3,3-dimethoxypropyl)-4-nitro-1H-pyrazole as a yellow oil which was used in the next step without further purification. LC-MS conditions B: $t_R$=0.54 min, [M+H]$^+$=no ionization.

Step 2:

To a solution of 1-(3,3-dimethoxypropyl)-4-nitro-1H-pyrazole (1.00 g, 4.65 mmol) in THF (20 mL), a 2N aq. HCl-solution (22 mL, 44 mmol) was added dropwise. After stirring at 80° C. for 10 min, the reaction mixture was allowed to reach rt, then sat. aq. NaHCO$_3$-solution was added to the reaction mixture and the solvent was removed under reduced pressure. The remaining aq. layer was extracted with EtOAc (2×). The combined org. layers were dried (MgSO$_4$), filtered and the solvent was removed under reduced pressure to yield 3-(4-nitro-1H-pyrazol-1-yl)propanal as yellow oil which was used in the next step without further purification. LC-MS conditions B: t$_R$=0.33 min, [M+H]$^+$=no ionization.

Step 3:

To a solution of 3-(4-nitro-1H-pyrazol-1-yl)propanal (722 mg, 4.27 mmol) in MeCN (7.0 mL) and DCM (5.0 mL), indoline (0.48 mL, 4.27 mmol) was added, followed by STAB (1.36 g, 6.40 mmol) and one drop of AcOH. The resulting yellow suspension was stirred at rt for 1 h 15 min, then water and DCM was added and the org. layer was separated. The aq. layer was extracted with DCM and the combined org. layers were washed with brine, dried (MgSO$_4$), filtered and the solvent was removed under reduced pressure to yield 1-(3-(4-nitro-1H-pyrazol-1-yl)propyl)indoline as a yellow oil which was used without further purification in the next step. LC-MS conditions B: t$_R$=0.76 min, [M+H]$^+$=273.06.

Step 4:

To a round bottom flask was added 1-(3-(4-nitro-1H-pyrazol-1-yl)propyl)indoline (2.10 g, 7.70 mmol), Pd/C (210 mg) and MeOH (48 mL, degassed). The flask was evacuated and backfilled with H$_2$ and the reaction mixture was stirred under H$_2$-atmosphere at rt for 18 h. The reaction mixture was filtered over celite, washed with MeOH and the solvent was removed under reduced pressure to yield the title compound as a red oil. LC-MS conditions B: t$_R$=0.39 min; [M+H]$^+$=243.12.

1-(3-Indol-1-yl-propyl)-1H-pyrazol-4-ylamine

A solution of 1-[3-(2,3-dihydro-indol-1-yl)-propyl]-1H-pyrazol-4-ylamine (200 mg, 0.83 mmol) in acetone (1.0 mL) was added dropwise to a suspension of MnO$_2$ (275 mg, 3.17 mmol) in acetone (2.0 mL). The resulting dark reaction mixture was stirred at rt overnight, then filtered over celite, washed with acetone and the solvent was removed under reduced pressure to yield the title compound which was used without further purification in the next step. LC-MS conditions B: t$_R$=0.51 min, [M+H]$^+$=241.20.

N-(2-(4-Amino-1H-pyrazol-1-yl)ethyl)-4,6-dimethoxypyrimidin-2-amine

Step 1: To a solution of 4-nitro-1H-pyrazole (2.50 g, 21.45 mmol) in MeCN (30 mL), Cs$_2$CO$_3$ (8.39 g, 25.74 mmol) and 2-(boc-amino)ethyl bromide (5.45 g, 23.59 mmol) was added. The resulting mixture was refluxed (80° C.) for 1.5 h, then the reaction mixture was allowed to reach rt. The mixture was diluted with DCM, filtered, the filter cake was washed with DCM and the filtrate was concentrated in vacuo. The residue was partitionned between water and EtOAc, the org. layer was separated and the aq. layer was extracted with EtOAc (1×). The combined org. layers were washed with brine, dried (MgSO$_4$) and concentrated in vacuo. Purification was performed by FC (EtOAc/hept 7:3 to EtOAc/MeOH 9:1) to obtain tert-butyl(2-(4-nitro-1H-pyrazol-1-yl)ethyl)carbamate as a slightly yellow solid which was used without further purification in the next step. LC-MS conditions A: t$_R$=0.72 min, [M+H]$^+$=257.08.

Step 2: To an ice-cooled solution of tert-butyl(2-(4-nitro-1H-pyrazol-1-yl)ethyl)carbamate (5.50 g, 21.49 mmol) in DCM (55 mL), TFA (20 mL, 261.16 mmol) was added dropwise. The resulting solution was stirred at 0° C. for 3 h, then the reaction mixture was concentrated in vacuo to obtain 2-(4-nitro-1H-pyrazol-1-yl)ethanamine-TFA salt as an off-white paste, which was used in the next step without further purification. LC-MS conditions A: t$_R$=0.21 min, no ionization.

Step 3: A microwave tube was charged with 2-(4-nitro-1H-pyrazol-1-yl)ethanamine (1.92 g, 5.52 mmol), NMP. (15 mL), 2-chloro-4,6-dimethoxypyrimidine (1.16 g, 6.62 mmol) and K$_2$CO$_3$ (4.19 g, 30.34 mmol). The resulting mixture was heated to 150° C. for 20 min in the microwave (no cooling). The reaction mixture was diluted with DCM and washed with water. The org. layer was separated and the aq. layer was extracted with DCM (2×) The combined organic layers were washed with brine, dried (MgSO$_4$), filtered and the solvent was removed under reduced pressure. Purification was performed by FC (EtOAc/hept 6:4) to obtain 4,6-dimethoxy-N-(2-(4-nitro-1H-pyrazol-1-yl)ethyl)pyrimidin-2-amine.

LC-MS conditions A: t$_R$=0.33 min, [M+H]$^+$=no ionization.

Step 4:

To 4,6-dimethoxy-N-(2-(4-nitro-1H-pyrazol-1-yl)ethyl)pyrimidin-2-amine (3.39 g, 11.54 mmol) in EtOAc (8.0 mL, degassed) and EtOH (32 mL, degassed), PtO$_2$ (1.23 g, 1.15 mmol) was added and the reaction mixture was stirred at rt under a H$_2$-atmosphere for 3 h. The mixture was diluted with EtOH, filtered over celite and the filter cake was rinsed with EtOH. The filtrate was concentrated to obtain the title compound of a pale pink solid. LC-MS conditions A: t$_R$=0.42 min, [M+H]$^+$=265.13.

[2-(4-Amino-pyrazol-1-yl)-ethyl]-(4,5-dimethoxy-pyrimidin-2-yl)-amine

Step 1:

To a solution of 4,5-dimethoxypyrimidin-2-amine (350 mg, 2.26 mmol) in DCM (3.5 mL), DIPEA (1.2 mL, 7.0 mmol) was added, followed by chloracetylchloride (0.30 mL, 3.72 mmol). The resulting dark brown reaction mixture was stirred at rt for 1 h, then quenched with water and diluted with DCM. The org. layer was separated and the aq. layer extracted with DCM (1×). The combined org. layers were washed with brine, dried (MgSO$_4$), filtered and the solvent removed under reduced pressure to obtain 2-chloro-N-(4,5-dimethoxypyrimidin-2-yl)acetamide as a brown oil which was used in the next step without further purification. LC-MS conditions B: t$_R$=0.38 min, [M+H]$^+$=232.07.

Step 2:

A flask was charged with 4-nitro-1H-pyrazole (A) (317 mg, 2.8 mmol), 2-chloro-N-(4,5-dimethoxypyrimidin-2-yl) acetamide (2.26 mmol), Cs$_2$CO$_3$ (1.0 g, 3.09 mmol) and MeCN (9.0 mL). The resulting reaction mixture was stirred at reflux (80° C.) for 1 h, then allowed to reach rt. The mixture was diluted with DCM, filtered, the filter cake was washed with DCM. The filtercake was redisolved in DCM and water, the org. layer was separated and the aq. layer was extracted with DCM (2×). The combined org. layers were washed with brine, dried (MgSO$_4$), filtered and concentrated to yield N-(4, 5-dimethoxypyrimidin-2-yl)-2-(4-nitro-1H-pyrazol-1-yl)acetamide as a crude which was used in the next step without further purification. LC-MS conditions B: t$_R$=0.46 min, [M+H]$^+$=309.10.

Step 3:

To N-(4,5-dimethoxypyrimidin-2-yl)-2-(4-nitro-1H-pyrazol-1-yl)acetamide (318 mg, 1.03 mmol) in THF (2.0 mL), BH$_3$ THF-complex solution (1 M in THF, 4.13 mL, 4.13 mmol) was added. After stirring at rt for 1.5 h, the reaction mixture was quenched with 1 N aq. HCl-solution (4 mL, 4 mmol) followed by concentrated HCl-solution (32%, 0.5 mL). After stirring for 10 min at rt, the reaction mixture was diluted with EtOAc, washed with sat. Na$_2$CO$_3$-solution. The aq. layer was reextracted with EtOAc and the comb. org. layers were evaporated, dissolved in DCM and washed with brine. The org. layer was dried (MgSO$_4$), filtered and the solvent was removed by reduced pressure. Purification was performed by FC (EtOAc/hex 1:1 to 100% EtOAc) to yield 4,5-dimethoxy-N-(2-(4-nitro-1H-pyrazol-1-yl)ethyl)pyrimidin-2-amine as a yellow solid. LC-MS conditions B: t$_R$=0.43 min, [M+H]$^+$=295.14.

Step 4:
To a solution of 5-dimethoxy-N-(2-(4-nitro-1H-pyrazol-1-yl)ethyl)pyrimidin-2-amine (100 mg, 0.34 mmol) in EtOAc (0.3 mL, degassed) and EtOH (0.9 mL, degassed), PtO$_2$ (12 mg, 0.05 mmol) was added and the reaction mixture was stirred at rt under a H$_2$-atmosphere for 18 h. The mixture was diluted with MeOH, filtered over celite and the filter cake was rinsed with MeOH. The filtrate was concentrated to obtain the title compound as a brown oil, which was used in the next step without further purification. LC-MS conditions B: t$_R$=0.23 min, [M+H]$^+$=265.17.

N-(2-(4-Amino-1H-pyrazol-1-yl)ethyl)-5-fluoropyridin-2-amine

Step 1:
To a solution of 2-amino-5-fluoropyridine (300 mg, 2.60 mmol) in DCM (4.0 mL), DIPEA (1.36 mL, 7.79 mmol) was added, followed by chloracetylchloride (0.23 mL, 2.86 mmol). The resulting dark brown reaction mixture was stirred at rt for 2 h, then quenched with water and diluted with DCM. The org. layer was separated and the aq. layer extracted with DCM (1×). The combined org. layers were washed with brine, dried (MgSO$_4$), filtered and the solvent removed under reduced pressure to obtain 2-chloro-N-(5-fluoropyridin-2-yl)acetamide as a brown oil which was used in the next step without further purification. LC-MS conditions A: t$_R$=0.60 min, [M+H]$^+$=189.31.

Step 2:
A flask was charged with 4-nitro-1H-pyrazole (230 mg, 2.03 mmol), 2-chloro-N-(5-fluoropyridin-2-yl)acetamide (2.24 mmol), Cs$_2$CO$_3$ (729 g, 2.24 mmol) and MeCN (11.5 mL). The resulting reaction mixture was stirred at reflux (80° C.) for 2 h, then allowed to reach rt. The mixture was diluted with DCM, filtered, the filter cake was washed with DCM. The filtercake was redisolved in DCM and water, the org. layer was separated and the aq. layer was extracted with DCM (2×). The combined org. layers were washed with brine, dried (MgSO$_4$), filtered and concentrated to yield N-(5-fluoropyridin-2-yl)-2-(4-nitro-1H-pyrazol-1-yl)acetamide as a crude which was used in the next step without further purification. LC-MS conditions A: t$_R$=0.67 min, [M+H]$^+$=266.32.

Step 3:
To N-(5-fluoropyridin-2-yl)-2-(4-nitro-1H-pyrazol-1-yl)acetamide (493 mg) in THF (2.0 mL), BH$_3$ THF-complex solution (1 M in THF, 7.3 mL, 7.3 mmol) was added dropwise. After stirring at rt for 3 h, the reaction mixture was quenched with 1 N aq. HCl-solution (3 mL, 3 mmol). The mixture was stirred for 15 min at rt, and heated to 60° C. for 1.5 h. The reaction mixture was diluted with EtOAc, washed with sat. aq. Na$_2$CO$_3$-solution. The aq. layer was reextracted with EtOAc and the comb. org. layers were evaporated, dissolved in DCM and washed with brine. The org. layer was dried (MgSO$_4$), filtered and the solvent was removed by reduced pressure to yield 5-fluoro-N-(2-(4-nitro-1H-pyrazol-1-yl)ethyl)pyridin-2-amine as a yellow solid. LC-MS conditions A: t$_R$=0.53 min, [M+H]$^+$=252.36.

Step 4:
To a solution of 5-fluoro-N-(2-(4-nitro-1H-pyrazol-1-yl)ethyl)pyridin-2-amine (100 mg, 0.34 mmol) in EtOAc (0.4 mL, degassed) and EtOH (1.2 mL, degassed), PtO$_2$ (12 mg, 0.05 mmol) was added and the reaction mixture was stirred at rt under a H$_2$-atmosphere for 6 h. The mixture was diluted with EtOH, filtered over celite and the filter cake was rinsed with EtOH. The filtrate was concentrated to obtain the title compound as a red oil, which was used in the next step without further purification. LC-MS conditions A: t$_R$=0.18 min, [M+H]$^+$=222.34.

N-(2-(4-Amino-1H-pyrazol-1-yl)ethyl)-5-methylpyridin-2-amine

The title compound has been synthesized according to the above described procedure for N-(2-(4-amino-1H-pyrazol-1-yl)ethyl)-5-fluoropyridin-2-amine, starting from commercially available 2-amino-5-methylpyridine. LC-MS conditions A: t$_R$=0.25 min, [M+H]$^+$=218.39.

N-(2-(4-Amino-1H-pyrazol-1-yl)ethyl)-4-fluoropyridin-2-amine

The title compound has been synthesized according to the above described procedure for N-(2-(4-amino-1H-pyrazol-1-yl)ethyl)-5-fluoropyridin-2-amine, starting from commercially available 2-amino-4-fluoropyridine. LC-MS conditions A: t$_R$=0.18 min, [M+H]$^+$=222.12.

N-(2-(4-Amino-1H-pyrazol-1-yl)ethyl)-4-methoxypyridin-2-amine

The title compound has been synthesized according to the above described procedure for N-(2-(4-amino-1H-pyrazol-1-yl)ethyl)-5-fluoropyridin-2-amine, starting from commercially available 2-amino-4-methoxypyridine. LC-MS conditions A: t$_R$=0.25 min, [M+H]$^+$=234.09.

1-(2-(Indolin-1-yl)ethyl)-1H-pyrazol-4-amine

Step 1:
To a solution of 2-(4-nitro-1H-pyrazol-1-yl)acetaldehyde (1.02 g, 4.97 mmol) in MeCN (18.0 mL), indoline (0.56 mL, 4.95 mmol) dissolved in MeCN (6 mL) was added. The resulting orange solution was stirred at rt for 5 min, then STAB (2.10 g, 9.90 mmol) was added in portions. After stirring at rt for 1 h, the reaction mixture was quenched with water and extracted with DCM (2×). The combined org. layers were concentrated and purification was performed by FC (EtOAc/toluene 2:8) to yield 1-(2-(4-nitro-1H-pyrazol-1-yl)ethyl)indoline as a brown solid. LC-MS conditions A: t$_R$=0.85 min, [M+H]$^+$=259.14.

Step 2:
To a solution of 1-(2-(4-nitro-1H-pyrazol-1-yl)ethyl)indoline (183 mg, 0.71 mmol) in EtOAc (0.7 mL, degassed) and EtOH (2 mL, degassed), PtO$_2$ (14 mg, 0.07 mmol) was added and the reaction mixture was stirred at rt under a H$_2$-atmosphere for 18 h. The mixture was diluted with EtOH, filtered over celite and the filter cake was rinsed with EtOH. The filtrate was concentrated to obtain the title compound as an oil, which was used in the next step without further purification. LC-MS conditions A: t$_R$=0.51 min, [M+H]$^+$=229.26.

1-[3-(5-Methoxy-2,3-dihydro-indol-1-yl)-propyl]-1H-pyrazol-4-ylamine

Step 1:
To a solution of 5-methoxyindole (500 mg, 3.39 mmol) in acetic acid (34 mL), sodium cyanoborohydride (641 mg, 10.20 mmol) was added in portions. After stirring for 30 min at rt, the mixture was quenched with water (2.0 mL) and concentrated. The yellow residue was dissolved in DCM, washed with aq. sat. NaHCO$_3$-solution and brine. The org. layers was dried (MgSO$_4$), filtered and the solvent removed under reduced pressure to yield 5-methoxyindoline which was stored in the freezer. LC-MS conditions B: $t_R$=0.24 min, [M+H]$^+$=150.09.

Step 2:

To a solution of 3-(4-nitro-1H-pyrazol-1-yl)propanal (200 mg, 1.18 mmol) in MeOH (12.0 mL), 5-methoxyindoline (176 mg, 1.18 mmol) was added. This reaction mixture was stirred at rt for 1 h, then NaBH$_4$ (121 mg, 3.20 mmol) was added and stirred for another 30 min at rt. The reaction mixture was quenched with water and extracted with EtOAc (2×). The combined org. layers were dried (MgSO$_4$), filtered and the solvent was removed under reduced pressure to yield 5-methoxy-1-(3-(4-nitro-1H-pyrazol-1-yl)propyl)indoline, which was used in the next step without further purification. LC-MS conditions B: $t_R$=0.56 min, [M+H]$^+$=303.15.

Step 3:

To a solution of 5-methoxy-1-(3-(4-nitro-1H-pyrazol-1-yl) propyl)indoline (1.18 mmol), in MeOH (6.0 mL, degassed), PtO$_2$ (12 mg, 0.05 mmol) was added and the reaction mixture was stirred at rt under a H$_2$-atmosphere for 18 h. The mixture was diluted with MeOH, filtered over celite and the filter cake was rinsed with MeOH. The filtrate was concentrated to obtain the title compound as a brown oil, which was used in the next step without further purification. LC-MS conditions B: $t_R$=0.32 min, [M+H]$^+$=273.1.

1-[3-(6-Methoxy-2,3-dihydro-indol-1-yl)-propyl]-1H-pyrazol-4-ylamine

The title compound was synthesized according to above mentioned procedure for 1-[3-(5-methoxy-2,3-dihydro-indol-1-yl)-propyl]-1H-pyrazol-4-ylamine, starting form 6-methoxyindole. LC-MS conditions B: $t_R$=0.46 min, [M+H]$^+$=273.23.

3-(2-Bromoethyl)-5-methoxy-1H-indole

Step 1:

To a solution of 5-methoxyindole (10.00 g, 67.95 mmol) in diethylether (200 mL), oxalyl chloride (7.79 mL, 88.33 mmol) was added at 0° C. After stirring at rt for 3 h, the solid was filtered off and washed with cold diethylether to yield 2-(5-methoxy-1H-indol-3-yl)-2-oxoacetyl chloride as a orange solid which was used as such in the next step. LC-MS conditions B: $t_R$=0.46 min, no ionization.

Step 2:

To a solution 2-(5-methoxy-1H-indol-3-yl)-2-oxoacetyl chloride (14.78 g, 62.20 mmol) in ethanol (144 mL), Et$_3$N (10.40 mL, 74.63 mmol) was added at 0° C. and the resulting yellow suspension was stirred at rt for 1 h. The percipitate was filtered off, washed with cold ethanol and diethylether to yield ethyl 2-(5-methoxy-1H-indol-3-yl)-2-oxoacetate as an orange oil. LC-MS conditions B: $t_R$=0.63 min, [M+H]$^+$=248.13.

Step 3:

To a solution yield ethyl 2-(5-methoxy-1H-indol-3-yl)-2-oxoacetate (14.64 g, 59.21 mmol) in THF (200 mL), LiAlH$_4$ in THF (2.4 M, 90 mL) was added at 0° C. The reaction mixture was allowed to reach rt, then it was refluxed (65° C.) for 20 min. The reaction mixture was quenched with EtOAc (10.0 mL) followed by H$_2$O (10.0 mL), then the solids were filtered off and washed with MeOH. The filtrate was concentrated and redissolved in EtOAc. The org. layer was washed with 0.1 M aq. HCl-solution (2×) and brine, dried (MgSO$_4$) and the solvent was removed under reduced pressure to yield 2-(5-methoxy-1H-indol-3-yl)ethanol, which was used in the next step without further purification. LC-MS conditions B: $t_R$=0.49 min, [M+H]$^+$=192.22.

Step 4:

To a solution of 2-(5-methoxy-1H-indol-3-yl)ethanol (4.0 g, 20.92 mmol) in DCM (30 mL), CBr$_4$ (7.98 g, 24.06 mmol) was added, then the reaction mixture was cooled to 0° C. and PPh$_3$ (6.3 g, 24.0 mmol) was added. After stirring at rt for 2 h, the solvent was removed under reduced pressure. Purification was performed by FC (EtOAc/hex 3:1, R$_f$=0.31) to yield the title compound as a brown oil which turned into a solid during storage in the freezer. LC-MS conditions B: $t_R$=0.78 min, [M+H]$^+$=254.06.

1-[2-(5-Methoxy-1H-indol-3-yl)-ethyl]-1H-pyrazol-4-ylamine

Step 1:

A microwave vial was charged with 4-nitro-1H-pyrazole (1.0 g, 8.84 mmol), 3-(2-bromoethyl)-5-methoxy-1H-indole (2.25 g, 8.84 mmol), Cs$_2$CO$_3$ (5.76 g, 17.69 mmol), MeCN (75.0 mL) and DMF (5.0 mL). The tube was sealed and the reaction mixture was irradiated in the microwave to 100° C. for 10 min with cooling. The reaction mixture was diluted with water and DCM, then the org. layer was separated and the aq. layer was extracted with DCM. The combined org. layers were dried (MgSO$_4$), filtered and the solvent was removed under reduced pressure. Purification was performed by FC (EtOAc/hex 1:4) to yield 5-methoxy-3-(2-(4-nitro-1H-pyrazol-1-yl)ethyl)-1H-indole as a yellow solid, which was used in the next step without further purification. LC-MS conditions B: $t_R$=0.70 min, [M+H]$^+$=287.13.

Step 2:

To a round bottom flask 5-methoxy-3-(2-(4-nitro-1H-pyrazol-1-yl)ethyl)-1H-indole (2.11 g, 7.37 mmol), Pd/C (200 mg) and EtOH (35 mL, degassed) was added. The flask was evacuated and backfilled with H$_2$ and the reaction mixture was stirred under H$_2$-atmosphere at rt for 18 h. The reaction mixture was filtered over celite, washed with EtOH and the solvent was removed under reduced pressure to yield the title compound as a red oil, which was used in the next step without further purification. LC-MS conditions B: $t_R$=0.42 min, [M+H]+=257.16.

1-(2-(5-Methoxy-1H-indol-3-yl)ethyl)-1H-imidazol-4-amine

Step 1:

To a solution of 4-nitroimidazole (120 mg, 1.06 mmol) in MeCN (3 mL), Cs$_2$CO$_3$ (380 mg, 1.167 mmol) and 3-(2-bromoethyl)-5-methoxy-1H-indol (270 mg, 1.06 mmol) was added. After stirring at 80° C. for 18 h, the mixture was filtered, the filter cake rinsed with DCM and the solvent was removed under reduced pressure. The residue was dissolved in EtOAc and the organic layer was washed with brine (1×), dried (MgSO$_4$) and the solvent was removed under reduced pressure. Purification by FC (EtOAc/hept 7:3) to yield a mixture of 5-methoxy-3-(2-(4-nitro-1H-imidazol-1-yl)ethyl)-1H-indole and 5-methoxy-3-(2-(5-nitro-1H-imidazol-1-yl) ethyl)-1H-indole as a yellow solid. The mixture was used as such in the next step. LC-MS conditions A $t_R$=0.73 min, [M+H]+=287.19.

Step 2:

To a solution of 5-methoxy-3-(2-(4-nitro-1H-imidazol-1-yl)ethyl)-1H-indole in EtOH/H$_2$O (1.8 mL/0.9 mL), NH$_4$Cl (158 mg, 2.95 mmol) and Fe (99 mg, 1.77 mmol) was added. The resulting black mixture was heated to 85° C. for 30 min, then it was filtered while hot and the filter cake was rinsed with EtOH. The filtrate was concentrated in vacuo and the residue partitioned between DCM and aq. 1 N NaOH-solution. The org. layer was separated and the aq. layer wa extracted with DCM. The combined organic extracts were washed with brine, dried (MgSO$_4$), filtered and the solvents were removed under reduced pressure to yield the title compound in mixture with 1-(2-(5-methoxy-1H-indol-3-yl)ethyl)-1H-imidazol-5-amine as a dark brown solid, which was used in the next step without further purification. LC-MS conditions A: t$_R$=0.52 min, [M+H]+=257.22.

N-(1H-Pyrazol-4-yl)-5-(m-tolyl)oxazole-4-carboxamide

Step 1:

To a round bottom flask, 4-nitro-1H-pyrazole (2.0 g, 17.68 mmol), Pd/C (200 mg, 1.89 mmol) and EtOH (15.0 mL, degassed) was added. The flask was evacuated and backfilled with H$_2$ and the reaction mixture was stirred under H$_2$-atmosphere at rt for 18 h. The reaction mixture was filtered over celite, washed with MeOH and the solvent was removed under reduced pressure to yield 1H-pyrazol-4-amine as a red oil which was used without further purification. $^1$H-NMR (400 MHz, DMSO) δ 3.72 (brs, 2H), 6.99 (s, 2H), 11.9 (brs, 1H).

Step 2:

To a solution of 5-(m-tolyl)oxazole-4-carboxylic acid (11.18 g) in DCM (65 mL), HOBT (11.15 g, 0.083 mol) and EDC (15.8 g, 0.083 mol) was added at 0° C. This suspension was stirred at this temperature for 10 min, then it was added to a suspension was of 1H-pyrazol-4-amine (5.48 g) and DIPEA (17.65 mL) in DCM (50 mL). The resulting mixture was allowed to warm to rt and was stirred at rt for 18 h. Percipitation of the desired compound was obtained by the addition of water. The solid was filtered and dried to yield the title compound. LC-MS conditions B: t$_R$=0.63 min, [M+H]+=269.13.

3-(2-Bromoethyl)-5-methoxy-1-methyl-1H-indole

A flask was charged with NaH (145 mg, 3.62 mmol), MeI (0.45 mL, 7.24 mmol) and THF (1.7 mL). The resulting grey suspension was stirred at rt for 5 min, then a solution of 3-(2-bromo-ethyl)-5-methoxy-1H-indole (230 mg, 0.90 mmol) in THF (4.1 mL) was added dropwise. After stirring for 18 h at rt, the reaction mixture was concentrated and purification by FC (hex/EtOAc 2:1, Rf=0.5) yielded the title compound as an yellow solid. LC-MS conditions 08Z acidic t$_R$=0.93 min, [M+H]+=no ionization.

3-(2-Bromoethyl)-5-methoxy-1H-pyrrolo[3,2-b]pyridine

Step 1:

2-(5-methoxy-1H-pyrrolo[3,2-b]pyridin-3-yl)ethanol was synthesized according to literature procedure (Organic Letters, 2009, p. 5142-5145) starting from 5-amino-2-methoxypyridine.

Step 2:

To a solution of 2-(5-methoxy-1H-pyrrolo[3,2-b]pyridin-3-yl)ethanol (353 mg, 1.84 mmol) in DCM (5.0 mL), CBr$_4$ (700 mg, 2.11 mmol) was added, then the reaction mixture was cooled to 0° C. and PPh$_3$ (554 mg, 2.11 mmol) was added. After stirring at rt for 2 h the solvent was removed under reduced pressure. Purification was performed by FC (EtOAc/hex 1:9 to 3:7) to yield the title compound as a brown oil, which was stored in the freezer. LC-MS conditions B: t$_R$=0.45 min, [M+H]+=255.03.

3-(2-Bromo-ethyl)-1-methyl-1H-indole

A flask was charged with NaH (900 mg, 37.52 mmol), MeI (3.14 mL, 50.00 mmol) and THF (7.5 mL). The resulting grey suspension was stirred at rt for 5 min, then a solution of 3-(2-bromethyl)-indol (1.12 g, 5.00 mmol) in THF (25 mL) was added dropwise. After stirring for 18 h at rt, the reaction mixture was concentrated, redissolved in DCM and washed with H$_2$O (3×). The org. layer was dried (MgSO$_4$), filtered and the solvent was removed under reduced pressure to yield the title compound as an yellow oil which was used as such in the next step. LC-MS conditions A: t$_R$=0.95 min, [M+H]+=no ionization.

3-(2-Bromo-ethyl)-6-methoxy-1H-indole

The title compound was synthesized according to above mentioned procedure for 3-(2-bromoethyl)-5-methoxy-1H-indole, starting with 6-methoxyindole yielding a brown oil which was stored in the freezer. LC-MS conditions B: t$_R$=0.81 min, [M+H]+=254.13.

3-(2-Bromoethyl)-6-methoxy-1-methyl-1H-indole

A flask was charged with NaH (110 mg, 4.60 mmol), MeI (0.39 mL, 6.13 mmol) and THF (1.5 mL). The resulting grey suspension was stirred at rt for 5 min, then a solution of 3-(2-Bromo-ethyl)-6-methoxy-1H-indole (156 mg, 0.61 mmol) in THF (2.5 mL) was added dropwise. After stirring for 18 h at rt, the reaction mixture was concentrated, redissolved in DCM and washed with H$_2$O (3×). The org. layer was dried (MgSO$_4$), filtered and the solvent was removed under reduced pressure to yield the title compound as an yellow oil which was used as such in the next step. LC-MS conditions B: t$_R$=0.94 min, [M+H]+=no ionization.

3-(2-Bromo-ethyl)-5-fluoro-1H-indole

The title compound was synthesized according to above mentioned procedure for 3-(2-bromoethyl)-5-methoxy-1H-indole, starting with 5-fluoroindole yielding a brown oil which was stored in the freezer. LC-MS conditions B: t$_R$=0.82 min, [M($^{81}$Br)+MeCN+H]+=244.07.

1-(2-Bromoethyl)-6-methoxy-1H-benzo[d]imidazole

Step 1:

A round bottom flask was charged with 2-bromo-4-methoxy-1-nitrobenzene (2.0 g, 8.6 mmol) and ethanolamine (8.1 mL, 135 mmol). The resulting reaction mixture was stirred at 50° C. for 4 h and at rt for 48 h, then water (32.0 mL) was added and the resulting precipitate was filtered off and rinsed with water to yield 2-((5-methoxy-2-nitrophenyl)amino)ethanol as a yellow solid LC-MS conditions B: t$_R$=0.56 min, [M+H]+=213.13.

Step 2:

To a round bottom flask, 2-((5-methoxy-2-nitrophenyl)amino)ethanol (1.43 g, 6.74 mmol), Pd/C (150 mg) and EtOH (30 mL, degassed) was added. The flask was evacuated and backfilled with H$_2$ and the reaction mixture was stirred under H$_2$-atmosphere at rt for 18 h. The reaction mixture was filtered over celite, washed with MeOH and the solvent was removed under reduced pressure to yield 2-((2-amino-5-methoxyphenyl)amino)ethanol as a red solid which was used as such without further purification. LC-MS conditions B: $t_R$=0.30 min, [M+H]$^+$=183.25.

Step 3:

To a solution of 2-((2-amino-5-methoxyphenyl)amino) ethanol (914 mg, 5.01 mmol) in THF (30 mL), formic acid (0.19 mL, 5.01 mmol) was added. After stirring at 80° C. for 30 min the reaction was allowed to reach rt and basified with conc. aq.NaHCO$_3$-solution. The aq. layer was extracted with DCM (5×). The combined org. layers were dried (MgSO$_4$), filtered and the solvent was removed under reduced pressure to yield 2-(6-methoxy-1H-benzo[d]imidazol-1-yl)ethanol as a brown oil which was used as such in the next step. LC-MS conditions B: $t_R$=0.30 min, [M+H]$^+$=193.13.

Step 4:

To a solution of 2-(6-methoxy-1H-benzo[d]imidazol-1-yl) ethanol (200 mg, 1.04 mmol) in DCM (6.0 mL), CBr$_4$ (397 mg, 1.20 mmol) was added, then the reaction mixture was cooled to 0° C. and PPh$_3$ (314 mg, 1.20 mmol) was added. After stirring at rt for 2 h the solvent was removed under reduced pressure to yield the title compound as a brown oil, which was used us such in the next step. LC-MS conditions B: $t_R$=0.42 min, [M($^{79}$Br)+H]$^+$=255.08.

3-(4,6-Dimethoxypyrimidin-2-yl)propyl methanesulfonate

Step 1:

To a round bottom flask 4,6-dimethoxypyrimidine-2yl-carbaldehyde 74% (1.50 g, 8.92 mmol) and methyl(triphenylphosphoranylidene)-acetate (3.04 g, 8.92 mmol) in THF (90 mL) was added. After stirring at rt for 18 h, the solvent was evaporated and the residue was purified by FC (EtOAc/hept 1:1 R$_f$=0.77) to yield a mixture of methyl 3-(4,6-dimethoxypyrimidin-2-yl)acrylate and methyl 3-(4-ethoxy-6-methoxypyrimidin-2-yl)acrylate as a yellow oil, due to the fact that the SM was only 74% pure. LC-MS conditions B: $t_R$=0.75 min, [M+H]$^+$=225.05 and $t_R$=0.83 min, [M+H]$^+$=239.07.

Step 2:

To a round bottom flask a mixture of methyl 3-(4,6-dimethoxypyrimidin-2-yl) and methyl 3-(4-ethoxy-6-methoxypyrimidin-2-yl)acrylate (1.80 g, 8.03 mmol), Pd/C (10 wt. %, 180 mg) and MeOH (60 mL, degassed) was added. The flask was evacuated and backfilled with H$_2$ and the reaction mixture was stirred under H$_2$-atmosphere at rt for 2 h. The reaction mixture was filtered over celite, washed with MeOH and the solvent was removed under reduced pressure to yield a mixture of methyl 3-(4,6-dimethoxypyrimidin-2-yl)propanoate and methyl 3-(4-ethoxy-6-methoxypyrimidin-2-yl) propanoate as as a yellow oil which was used as such in the next step. LC-MS conditions B: $t_R$=0.61 min, [M+H]$^+$=227.04 and $t_R$=0.70 min, [M+H]$^+$=241.11.

Step 3:

To a solution of a mixture of methyl 3-(4,6-dimethoxypyrimidin-2-yl)propanoate and methyl 3-(4-ethoxy-6-methoxypyrimidin-2-yl)propanoate (1.71 g, 7.56 mmol) in THF (25 mL), DiBAL-H (1 M in THF, 23.0 mL, 23.0 mmol) was added at 0° C. After stirring for 40 min at 0° C., the reaction mixture was allowed to warm to rt, then diluted with DCM and acidified to pH 1 with 2 N aq. HCl-solution (50 mL). The org. layer was separated and the aq. layer was extracted with DCM (2×), then the aq. layer was bascified with aq. NaHCO$_3$-solution and extracted with DCM (2×). The combined org. layers were dried (MgSO$_4$), filtered and the solvent was removed under reduced pressure. Purification by prep. HPLC (basic) yielded 3-(4,6-dimethoxypyrimidin-2-yl)propan-1-ol and 3-(4-ethoxy-6-methoxypyrimidin-2-yl)propan-1-ol as yellow oils. 3-(4,6-dimethoxypyrimidin-2-yl)propan-1-ol: LC-MS conditions B: $t_R$=0.43 min, [M+H]$^+$=199.10. 3-(4-ethoxy-6-methoxypyrimidin-2-yl)propan-1-ol: LC-MS conditions B: $t_R$=0.50 min, [M+H]$^+$=213.13.

Step 4:

To a solution of 3-(4,6-dimethoxypyrimidin-2-yl)propan-1-ol (100 mg, 0.50 mmol) in DCM (2.0 mL), Et$_3$N (0.21 mL, 1.51 mmol) was added. After stirring for 5 min at rt, the reaction mixture was cooled to 0° C. and methansulfonylchloride (0.05 mL, 0.61 mmol) was added. The reaction mixture was stirred for 10 min at 0° C. and for 20 min at rt, then poured onto ice water. The aq. layer was extracted with DCM, the org. layer was washed with 1 N aq. HCl-solution followed by sat. NaHCO$_3$-solution, then dried (MgSO$_4$), filtered and the solvent was removed under reduced pressure to yield the tiltle compound as a yellow oil which was used immediately in the next step. The LC-MS conditions B: $t_R$=0.60 min, [M+H]$^+$=277.09.

3-(4-Ethoxy-6-methoxypyrimidin-2-yl)propyl methanesulfonate

The title compound was synthesized according to the procedure described for 3-(4,6-dimethoxypyrimidin-2-yl)propyl methanesulfonate (step 4), starting from 3-(4-ethoxy-6-methoxypyrimidin-2-yl)propan-1-ol. LC-MS conditions B: $t_R$=0.68 min, [M+H]$^+$=291.08.

N-(1-(2-Hydroxyethyl)-1H-pyrazol-4-yl)-5-(m-tolyl) oxazole-4-carboxamide

Step 1:

To a solution of 2-(4-nitro-1H-pyrazol-1-yl)ethanol (9.12 g, 58.07 mmol) in EtOAc (20 mL, degassed) and EtOH (60 mL, degassed), PtO$_2$ (1.13 g, 5.81 mmol) was added and the reaction mixture was stirred at rt under a H$_2$-atmosphere for 18 h. The mixture was diluted with EtOH, filtered over celite and the filter cake was rinsed with EtOH. The filtrate was concentrated to obtain 2-(4-amino-1H-pyrazol-1-yl)ethanol as a red oil, which was used in the next step without further purification. LC-MS conditions A: $t_R$=0.14 min, [M+H]$^+$=128.24.

Step 2:

To a solution of 5-(m-tolyl)oxazole-4-carboxylic acid (5.50 g, 27.07 mmol) in DCM (80 mL), TBTU (13.04 g, 40.60 mmol) and DIPEA (13.90 mL, 81.20 mmol) was added. After stirring for 40 min at rt, 2-(4-amino-1H-pyrazol-1-yl)ethanol (3.47 g, 27.07 mmol) dissolved in DCM (10 mL) and DMF (4 mL) was added to the reaction mixture and stirred at rt for 1 h, then the reaction mixture was diluted with DCM and water, the org. layer was separated and the aq. layer extracted with DCM (1×). The combined org. layers were washed with brine, dried (MgSO$_4$), filtered and the solvent was removed under reduced pressure. Purification by FC (DCM/MeOH, 95:5 to DCM/MeOH 9:1) yielded the tiltle compound as a white solid. LC-MS conditions A: $t_R$=0.71 min, [M+H]$^+$=313.44.

2-(4-(5-(m-Tolyl)oxazole-4-carboxamido)-1H-pyrazol-1-yl)ethyl methanesulfonate

To an ice-cooled solution of N-(1-(2-hydroxyethyl)-1H-pyrazol-4-yl)-5-(m-tolyl)oxazole-4-carboxamide (178 mg, 0.57 mmol) in DCM (8 mL), Et$_3$N (0.24 mL, 1.71 mmol) was added. After stirring for 5 min at 0° C., methanesulfonyl chloride (0.11 mL, 1.43 mmol) was added dropwise, and the resulting suspension was stirred at 0° C. for 1 h 15, then quenched with water and extracted with DCM (2×). The combined org. layers were washed with brine, dried (MgSO$_4$) and concentrated in vacuo to obtain the title compound as an oil. LC-MS conditions A: t$_R$=0.90 min, [M+H]$^+$=391.03.

2-(4-(5-(m-Tolyl)oxazole-4-carboxamido)-1H-pyrazol-1-yl)ethyl 4-methyl-benzenesulfonate To an ice-cooled solution of N-(1-(2-hydroxyethyl)-1H-pyrazol-4-yl)-5-(m-tolyl)oxazole-4-carboxamide (2.57 g, 8.23 mmol) in DCM (70 mL), Et$_3$N (3.44 mL, 24.69 mmol) was added. After stirring for 20 min at 0° C., p-toluenesulfonyl chloride (1.73 g, 9.05 mmol), was added dropwise, and the resulting suspension was stirred at 0° C. for 3 h, then quenched with water and extracted with DCM (2×). The combined org. layers were washed with 1 N aq. HCl-solution and brine, dried (MgSO$_4$), filtered and concentrated in vacuo to obtain the title compound as an oil. LC-MS conditions A: t$_R$=0.93 min, [M+H]$^+$=467.46.

N-(1-(2-Hydroxyethyl)-3,5-dimethyl-1H-pyrazol-4-yl)-5-(m-tolyl)oxazole-4-carboxamide Step 1:
To a solution of 3,5-dimethyl-4-nitro-1H-pyrazole (500 mg, 3.52 mmol) in MeCN (5 mL), Cs$_2$CO$_3$ (1.26 g, 3.87 mmol) and 2-bromoethanol (0.3 mL, 4.21 mmol) was added. The resulting mixture was refluxed (90° C.) for 3 h, then the reaction mixture was allowed to reach rt. The mixture was diluted with DCM, filtered, the filter cake rinsed with DCM and the filtrate concentrated in vacuo. The residue was partitionned between water and EtOAc, the org. layer was separated and the aq. layer was extracted with EtOAc (1×). The combined org. layers were washed with brine, dried (MgSO$_4$), filtered and concentrated in vacuo to yield 2-(3,5-dimethyl-4-nitro-1H-pyrazol-1-yl)ethanol as a white solid. LC-MS conditions A: t$_R$=0.53 min, [M+H]$^+$=186.39.

Step 2:
To a solution of 2-(3,5-dimethyl-4-nitro-1H-pyrazol-1-yl)ethanol (624 mg, 3.37 mmol) in EtOAc (1.2 mL, degassed) and EtOH (3.6 mL, degassed), PtO$_2$ (66 mg, 0.34 mmol) was added and the reaction mixture was stirred at rt under a H$_2$-atmosphere for 30 h. The mixture was diluted with EtOH, filtered over celite and the filter cake was rinsed with EtOH. The filtrate was concentrated to obtain 2-(4-amino-3,5-dimethyl-1H-pyrazol-1-yl)ethanol as a pale brown solid, which was used in the next step without further purification. LC-MS conditions A: t$_R$=0.16 min, [M+H]$^+$=156.29.

Step 3:
To a solution of 5-(m-tolyl)oxazole-4-carboxylic acid (550 mg, 2.71 mmol) in DCM (15 mL), TBTU (1.303 g, 4.06 mmol) and DIPEA (1.39 mL, 8.12 mmol) was added. After stirring for 40 min at rt, 2-(4-amino-3,5-dimethyl-1H-pyrazol-1-yl)ethanol (420 mg, 2.71 mmol) dissolved in DCM (5 mL) was added to the solution and the resulting mixture was stirred at rt for 1 h. The reaction mixture was diluted with DCM and water, the organic layer was separated and the aq. layer was extracted with DCM (2×). The combined org. layers were washed with brine, dried (MgSO$_4$), filtered and the solvent was removed under reduced pressure. Purification by FC (DCM/MeOH 92:8) yielded the title compound as a white solid. LC-MS conditions A: t$_R$=0.70 min, [M+H]$^+$=341.46.

2-(3,5-Dimethyl-4-(5-(m-tolyl)oxazole-4-carboxamido)-1H-pyrazol-1-yl)ethyl 4-methyl-benzenesulfonate The title compound was synthesized according to above mentioned procedure for 2-(4-(5-(m-tolyl)oxazole-4-carboxamido)-1H-pyrazol-1-yl)ethyl-4-methylbenzenesulfonate, starting from N-(1-(2-hydroxyethyl)-3,5-dimethyl-1H-pyrazol-4-yl)-5-(m-tolyl)oxazole-4-carboxamide. LC-MS conditions A: t$_R$=0.93 min, [M+H]$^+$=467.46.

N-(1-(2-Aminoethyl)-1H-pyrazol-4-yl)-5-(m-tolyl)oxazole-4-carboxamide

Step 1:
A flask was charged with 4-nitro-1H-pyrazole (3.5 g, 30.02 mmol), 2-(boc-amino)ethylbromide (6.9 g, 30.02 mmol), Cs$_2$CO$_3$ (1.07 g, 33.02 mmol) and MeCN (60 mL). The resulting reaction mixture was stirred at reflux (80° C.) for 1.5 h, then allowed to reach rt. The mixture was diluted with DCM, filtered, the filter cake was washed with DCM. The filtrate was concentrated to yield tert-butyl(2-(4-nitro-1H-pyrazol-1-yl)ethyl)carbamate as a light orange oil, which was used in the next step without further purification. LC-MS conditions B: t$_R$=0.63 min, [M+H]$^+$=257.35.

Step 2:
To a round-bottom flask tert. butyl(2-(4-nitro-1H-pyrazol-1-yl)ethyl)carbamate (7.88 g, 30.75 mmol), Pd/C (10%, 788 mg) and MeOH (130 mL, degassed) was added. The flask was evacuated and backfilled with H$_2$ and the reaction mixture was stirred under H$_2$-atmosphere at rt for 18 h. The reaction mixture was filtered over celite, washed with MeOH and the solvent was removed under reduced pressure to yield tert-butyl(2-(4-amino-1H-pyrazol-1-yl)ethyl)carbamate as a purple oil which was used in the next step without further purification. LC-MS conditions B: t$_R$=0.35 min, [M+H]$^+$=227.49.

Step 3:
To a solution of 5-(m-tolyl)oxazole-4-carboxylic acid (1.60 g, 7.87 mmol) in DCM (15 mL), tert-butyl(2-(4-amino-1H-pyrazol-1-yl)ethyl)carbamate (1.80 g, 7.96 mmol), DIPEA (6.8 mL, 39.86 mmol) and HATU (7.485 g, 19.69 mmol) was added. After stirring the reaction mixture at rt for 18 h, the reaction mixture was diluted with DCM and H$_2$O. The org. layer was separated and the aq. layer was extracted with DCM (3×). The combined org. layers wered dried (MgSO$_4$), filtered and the solvent was removed under reduced pressure. Purification by FC (EtOA/hex 3:7 to 1:1) yielded tert-butyl(2-(4-(5-(m-tolyl)oxazole-4-carboxamido)-1H-pyrazol-1-yl)ethyl)carbamate as a white solid. LC-MS conditions B: t$_R$=0.8 min, [M+H]$^+$=412.46.

Step 4:
To a suspension of tert-butyl(2-(4-(5-(m-tolyl)oxazole-4-carboxamido)-1H-pyrazol-1-yl)ethyl)carbamate (4.29 g, 10.426 mmol) in DCM (60 mL), TFA (12 mL, 156.39 mmol) was added at 0° C. After strring for 1 h at rt, the reaction mixture was concentrated. The residue was dissolved in DCM and 2 N aq. NaOH-solution was added. The org. layer was separated and the aq. layer was extracted with DCM (2×). The combined org. layers were dried (MgSO$_4$), filtered and the solvent removed to yield the title compound as a white solid, which was used in the next step without further purification. LC-MS conditions B: t$_R$=0.54 min, [M+H]$^+$=312.31.

N-(1-(2-Aminoethyl)-1H-pyrazol-4-yl)-5-(m-tolyl)thiazole-4-carboxamide

The title compound was synthesized according to above mentioned procedure for N-(1-(2-aminoethyl)-1H-pyrazol- 4-yl)-5-(m-tolyl)oxazole-4-carboxamide, starting from 5-(m-tolyl)thiazole-4-carboxylic acid. LC-MS conditions B: $t_R$=0.54 min, [M+H]$^+$=328.10.

N-(1-(2-Aminoethyl)-1H-imidazol-4-yl)-5-(m-tolyl)oxazole-4-carboxamide

The title compound was synthesized according to above mentioned procedure for N-(1-(2-aminoethyl)-1H-pyrazol-4-yl)-5-(m-tolyl)oxazole-4-carboxamide, starting from 1H-imidazol-4-amine. LC-MS conditions B: $t_R$=0.47 min, [M+H]$^+$=312.29.

(R)—N-(1-(2-Aminopropyl)-1H-pyrazol-4-yl)-5-(m-tolyl)oxazole-4-carboxamide

The title compound was synthesized according to procedure described for N-(1-(2-aminoethyl)-1H-pyrazol-4-yl)-5-(m-tolyl)oxazole-4-carboxamide starting with (R)-2-((tert-butoxycarbonyl)amino)propyl 4-methylbenzenesulfonate. Synthesis of (R)-2-((tert-butoxycarbonyl)amino)propyl 4-methylbenzenesulfonate was performed according to Bioorg. Med. Chem. 16 (2008) 1966-1982. LC-MS conditions B: $t_R$=0.55 min, [M+H]$^+$=326.11.

(S)—N-(1-(2-Aminopropyl)-1H-pyrazol-4-yl)-5-(m-tolyl)oxazole-4-carboxamide

The title compound was synthesized according to procedure described for N-(1-(2-aminoethyl)-1H-pyrazol-4-yl)-5-(m-tolyl)oxazole-4-carboxamide starting with (S)-2-((tert-butoxycarbonyl)amino)propyl 4-methylbenzenesulfonate. Synthesis of (S)-2-((tert-butoxycarbonyl)amino)propyl 4-methylbenzenesulfonate was performed according to Bioorg. Med. Chem. 16 (2008) 1966-1982. LC-MS conditions B: $t_R$=0.55 min, [M+H]$^+$=326.11.

N-(1-(3-Aminopropyl)-1H-pyrazol-4-yl)-5-(m-tolyl)oxazole-4-carboxamide

The title compound was synthesized according to above mentioned procedure for N-(1-(2-aminoethyl)-1H-pyrazol-4-yl)-5-(m-tolyl)oxazole-4-carboxamide, using 3-(Boc-amino)propyl bromide. LC-MS conditions B: $t_R$=0.56 min, [M+H]$^+$=326.19.

rac-N-(1-(Pyrrolidin-2-ylmethyl)-1H-pyrazol-4-yl)-5-(m-tolyl)oxazole-4-carboxamide Step 1:
To N-(1H-pyrazol-4-yl)-5-(m-tolyl)oxazole-4-carboxamide (150 mg, 0.56 mmol) in DMF (1.5 mL), tert-butyl 2-(bromomethyl)pyrrolidine-1-carboxylate (148 mg, 0.56 mmol) was added and K$_2$CO$_3$ (309 mg, 2.24 mmol) followed by tetrabutylammoniumbromide (18 mg, 0.056 mmol). The reaction mixture was heated to 80° C. for 2 h, then tert-butyl 2-(bromomethyl)pyrrolidine-1-carboxylate (1 eq.) followed by heating to 90° C. for 6 h. The reaction mixture was diluted with EtOAc, washed with sat. aq. NaHCO$_3$-solution (1×) and brine (1×). The aq. layers were reextracted with EtOAc (1×). The combined organic layers were dried (MgSO$_4$), filtered and the solvent was removed under reduced pressure. Purification by FC (EtOAc/hex 9:1, Rf=0.45) yielded rac-tert-butyl 2-((4-(5-(m-tolyl)oxazole-4-carboxamido)-1H-pyrazol-1-yl)methyl)pyrrolidine-1-carboxylate as a yellow foam. LC-MS conditions A: $t_R$=0.94 min, [M+H]$^+$=452.23.

Step 2:
To a solution of rac-tert-butyl 2-((4-(5-(m-tolyl)oxazole-4-carboxamido)-1H-pyrazol-1-yl)methyl)pyrrolidine-1-carboxylate (100 mg, 0.22 mmol) in DCM (2.3 mL), TFA (0.170 mL, 2.215 mmol) was added at 0° C. After stirring for 5 h at rt, the solvent and the remaining TFA was removed under reduced pressure. The residue was dissolved in DCM and 1 N aq. NaOH-solution was added until basic. The layers were separated and the aq. layer was extracted with DCM (1×). The combined organic layers were washed with brine, dired (MgSO$_4$), filterd and the solvent was removed under reduced pressure to yield rac-N-(1-(pyrrolidin-2-ylmethyl)-1H-pyrazol-4-yl)-5-(m-tolyl)oxazole-4-carboxamide a yellow oil which was used in the next step without further purification. LC-MS conditions A: $t_R$=0.62 min, [M+H]$^+$=352.07.

4,6-Dimethoxy-5-methyl-2-(methylsulfonyl)pyrimidine

Step 1:
To an ice-cooled solution of thiourea (1 g, 13.14 mmol) and diethyl methylmalonate (3.4 mL, 19.71 mmol) in EtOH (15 mL), NaOMe (2.68 g, 39.41 mmol) was added portionwise. After stirring at 0° C. for 30 min, the reaction was allowed to reach rt and was stirred for another 3 h at rt. The mixture was quenched with diluted acetic acid and the solid was filtered off to yield 2-mercapto-5-methylpyrimidine-4,6-diol as a white solid which was used in the next step without further purification. LC-MS conditions A: $t_R$=0.21 min, [M+H]$^+$=159.11.

Step 2:
A solution of 2-mercapto-5-methylpyrimidine-4,6-diol (2.08 g, 13.14 mmol) in 2 N aq. NaOH-solution (19.7 mL, 39.41 mmol) was cooled to 0° C., then MeI (2.07 mL, 32.84 mmol) was added dropwise and the resulting mixture was stirred at 0° C. for 1 h 40 and at rt for 2 h. The reaction mixture was concentrated to yield 5-methyl-2-(methylthio)pyrimidine-4,6-diol as a white solid which was used in the next step without further purification. LC-MS conditions A: $t_R$=0.45 min, [M+H]$^+$=172.96.

Step 3:
A round bottom flask containing 5-methyl-2-(methylthio)pyrimidine-4,6-diol (1.63 g, 2.90 mmol) was cooled to 0° C. before POCl$_3$ (5.41 mL, 58.07 mmol) followed by N,N-dimethylaniline (1.10 mL, 8.71 mmol) was added dropwise. The resulting heterogeneous mixture was stirred at 0° C. for 10 min, then at rt for another 10 min, before the reaction mixture was refluxed (130° C.) for 2.5 h. The reaction mixture was concentrated to dryness and the obtained dark paste was taken up into EtOAc (110 mL) and brine (8 mL). The org. layer was separated, dried (MgSO$_4$), filtered and the solvent was removed under reduced pressure to yield 4,6-dichloro-5-methyl-2-(methylthio)pyrimidine which was directly used in the next step. LC-MS conditions A: $t_R$=0.90 min, [M+H]$^+$=no ionization.

Step 4:
To an ice-cooled solution of 4,6-dichloro-5-methyl-2-(methylthio)pyrimidine (607 mg, 2.903 mmol) in MeOH (7 mL), NaOMe (1.25 g, 23.23 mmol) was added portionwise. The brown suspension was slowly allowed to reach rt, stirred at rt for 18 h and refluxed (85° C.) for 3 h. Due to the fact that the reaction was not completed, 0.4 eq. of NaOMe was added and the dark yellow suspension was refluxed (85° C.) for another 18 h. The reaction mixture was allowed to reach rt, then the solvent was removed and the residue was redissolved in EtOAc. The org. layer was washed with water, the aq. layer was reextracted with EtOAc (100 mL) and the combined org.

layers were washed with brine, dried (MgSO$_4$), filtered and the solvent was removed under reduced pressure. Purification by FC (EtOAc/hept 3:97) yielded 4,6-dimethoxy-5-methyl-2-(methylthio)pyrimidine as a solid. LC-MS conditions A: $t_R$=0.93 min, [M+H]$^+$=201.12.

Step 5:

To an ice-cooled solution of 4,6-dimethoxy-5-methyl-2-(methylthio)pyrimidine, m-CPBA (108 mg, 0.62 mmol) was added and the resulting mixture was stirred at 0° C. for 1 h then at rt for 18 h. The mixture was quenched with a sat. aq. NaHCO$_3$-solution, extracted with DCM (2×) and the combined org. layers were dried (MgSO$_4$), filtered and the solvent was removed under reduced pressure to yield the title compound as a solid which was used in the next step without further purification. LC-MS conditions A: $t_R$=0.73 min, [M+H]$^+$=233.11.

N-(1-(2-oxoethyl)-1H-pyrazol-4-yl)-5-(m-tolyl)oxazole-4-carboxamide

Step 1:

To a solution of 1-(2,2-dimethoxyethyl)-4-nitro-1H-pyrazole (6.51 g, 26.53 mmol) in EtOAc (12 mL, degassed) and EtOH (36 mL, degassed), PtO$_2$ (602 mg, 2.65 mmol) was added and the reaction mixture was stirred at rt under a H$_2$-atmosphere for 3 h. The mixture was diluted with EtOH, filtered over celite and the filter cake was rinsed with EtOH. The filtrate was concentrated to obtain 1-(3,3-dimethoxypropyl)-1H-pyrazol-4-amine as a purple oil, which was used in the next step without further purification. LC-MS conditions A: $t_R$=0.16-0.21 min, [M+H]$^+$=172.03.

Step 2:

To a solution of 5-(m-tolyl)oxazole-4-carboxylic acid (5.34 g, 26.28 mmol) in DCM (135 mL), TBTU (12.66 g, 39.42 mmol) and DIPEA (13.50 mL, 78.84 mmol) was added. After stirring for 30 min at rt, 1-(3,3-dimethoxypropyl)-1H-pyrazol-4-amine (4.50 g, 26.29 mmol) dissolved in DCM (15 mL) and DMF (2 mL) was added to the reaction mixture and stirred at rt for 1 h, then the reaction mixture was diluted with DCM and water, the org. layer was separated and the aq. layer extracted with DCM (1×). The combined org. layers were washed with brine, dried (MgSO$_4$), filtered and the solvent was removed under reduced pressure. Purification by FC (EtOAc/hept 7:3) yielded N-(1-(2,2-dimethoxyethyl)-1H-pyrazol-4-yl)-5-(m-tolyl)oxazole-4-carboxamide as a pale yellow solid. LC-MS conditions A: $t_R$=0.82 min, [M+H]$^+$=357.06.

Step 3:

To N-(1-(2,2-dimethoxyethyl)-1H-pyrazol-4-yl)-5-(m-tolyl)oxazole-4-carboxamide (800 mg, 2.25 mmol) in THF (11.5 mL), 2 N aq. HCl-solution (10.3 mL, 20.60 mmol) was added dropwise and the resulting solution was refluxed (80° C.) for 1.5 h. The reaction mixture was allowed to reach rt, then neutralized with sat. aq. NaHCO$_3$-solution and the org. solvent was removed under reduced pressure. The remaining aq. layer was extracted with EtOAc (2×) and the combined org. layer were washed with brine, dried (MgSO$_4$), filtered and concentrated to obtain the title compound as a yellow solid which was used immediately in the next step. LC-MS conditions C: $t_R$=0.72 min, [M+H$_2$O+H]$^+$=329.09.

Preparation of Examples

Listed in Table 1 below are example compounds, prepared according to the above-mentioned general procedure A, from the corresponding carboxylic acid (see starting materials A), either readily available or prepared as described above and the corresponding amine (see starting materials B), either readily available or prepared as described above.

TABLE 1

| Example No. | Compound of Formula (I) | Starting Material A | Starting Material B | MS-data m/z [M + H]$^+$ $t_R$ [min] Method D |
|---|---|---|---|---|
| 1 | 5-m-Tolyl-oxazole-4-carboxylic acid [1-(2-phenoxy-ethyl)-1H-pyrazol-4-yl]-amide | 5-(m-Tolyl)oxazole-4-carboxylic acid | 1-(2-Phenoxy-ethyl)-1H-pyrazol-4-ylamine | 389.2 1.07 |
| 2 | 5-m-Tolyl-oxazole-4-carboxylic acid {1-[2-(3-fluoro-phenyl)-ethyl]-1H-pyrazol-4-yl}-amide | 5-(m-Tolyl)oxazole-4-carboxylic acid | 1-[2-(3-Fluoro-phenyl)-ethyl]-1H-pyrazol-4-ylamine | 391.2 1.09 |
| 3 | 5-m-Tolyl-oxazole-4-carboxylic acid (1-phenethyl-1H-pyrazol-4-yl)-amide | 5-(m-Tolyl)oxazole-4-carboxylic acid | 1-Phenethyl-1H-pyrazol-4-ylamine | 373.2 1.09 |
| 4 | 5-m-Tolyl-oxazole-4-carboxylic acid {1-[2-(2-methyl-benzoimidazol-1-yl)-ethyl]-1H-pyrazol-4-yl}-amide | 5-(m-Tolyl)oxazole-4-carboxylic acid | 1-[2-(2-Methyl-benzoimidazol-1-yl)-ethyl]-1H-pyrazol-4-ylamine | 427.3 0.74 |
| 5 | 5-m-Tolyl-oxazole-4-carboxylic acid {1-[2-(5-fluoro-pyridin-2-ylamino)-ethyl]-1H-pyrazol-4-yl}-amide | 5-(m-Tolyl)oxazole-4-carboxylic acid | N-(2-(4-Amino-1H-pyrazol-1-yl)ethyl)-5-fluoropyridin-2-amine | 407.3 0.78 |
| 6 | 5-m-Tolyl-oxazole-4-carboxylic acid {1-[2-(5-methyl-pyridin-2-ylamino)-ethyl]-1H-pyrazol-4-yl}-amide | 5-(m-Tolyl)oxazole-4-carboxylic acid | N-(2-(4-Amino-1H-pyrazol-1-yl)ethyl)-5-methyl pyrid in-2-amine | 403.3 0.73 |
| 7 | 5-m-Tolyl-oxazole-4-carboxylic acid {1-[2-(3-methoxy-phenyl)-ethyl]-1H-pyrazol-4-yl}-amide | 5-(m-Tolyl)oxazole-4-carboxylic acid | 1-[2-(3-Methoxy-phenyl)-ethyl]-1H-pyrazol-4-ylamine | 403.3 1.08 |
| 8 | 5-m-Tolyl-oxazole-4-carboxylic acid {1-[2-(3-methoxy-phenoxy)-ethyl]-1H-pyrazol-4-yl}-amide | 5-(m-Tolyl)oxazole-4-carboxylic acid | 1-[2-(3-Methoxy-phenoxy)-ethyl]-1H-pyrazol-4-ylamine | 419.2 1.07 |
| 9 | 5-Phenyl-oxazole-4-carboxylic acid {1-[2-(4,6-di methoxy-pyrimid in-2-yloxy)-ethyl]-1H-pyrazol-4-yl}-amide | 5-Phenyloxazole-4-carboxylic acid | 1-[2-(4,6-Dimethoxy-pyrimidin-2-yloxy)-ethyl]-1H-pyrazol-4-ylamine | 437.2 0.96 |
| 10 | 5-(3-Fluoro-phenyl)-oxazole-4-carboxylic acid {1-[2-(4,6-dimethoxy- | 5-(3-Fluorophenyl) | 1-[2-(4,6-Dimethoxy-pyrimidin-2-yloxy)- | 455.2 0.99 |

TABLE 1-continued

| Example No. | Compound of Formula (I) | Starting Material A | Starting Material B | MS-data m/z [M + H]+ t_R [min] Method D |
|---|---|---|---|---|
| | pyrimidin-2-yloxy)-ethyl]-1H-pyrazol-4-yl}-amide | oxazole-4-carboxylic acid | ethyl]-1H-pyrazol-4-ylamine | |
| 11 | 5-(3-Dimethylamino-phenyl)-oxazole-4-carboxylic acid {1-[2-(4,6-dimethoxy-pyrimidin-2-yloxy)-ethyl]-1H-pyrazol-4-yl}-amide | 5-(3-(Dimethylamino)phenyl)oxazole-4-carboxylic acid | 1-[2-(4,6-Dimethoxy-pyrimidin-2-yloxy)-ethyl]-1H-pyrazol-4-ylamine | 480.3 0.84 |
| 12 | 5-m-Tolyl-oxazole-4-carboxylic acid {1-[2-(5,6-dimethoxy-indol-1-yl)-ethyl]-1H-pyrazol-4-yl}-amide | 5-(m-Tolyl)oxazole-4-carboxylic acid | 1-[2-(5,6-Dimethoxy-indol-1-yl)-ethyl]-1H-pyrazol-4-ylamine | 472.3 1.01 |
| 13 | 5-m-Tolyl-oxazole-4-carboxylic acid {1-[3-(2,3-dihydro-indol-1-yl)-propyl]-1H-pyrazol-4-yl}-amide | 5-(m-Tolyl)oxazole-4-carboxylic acid | 1-[3-(2,3-Dihydro-indol-1-yl)-propyl]-1H-pyrazol-4-ylamine | 428.3 1.16 |
| 14 | 5-m-Tolyl-oxazole-4-carboxylic acid {1-[2-(4-fluoro-pyridin-2-ylamino)-ethyl]-1H-pyrazol-4-yl}-amide | 5-(m-Tolyl)oxazole-4-carboxylic acid | N-(2-(4-Amino-1H-pyrazol-1-yl)ethyl)-4-fluoropyridin-2-amine | 407.3 0.78 |
| 15 | 5-m-Tolyl-oxazole-4-carboxylic acid {1-[2-(4-methoxy-pyridin-2-ylamino)-ethyl]-1H-pyrazol-4-yl}-amide | 5-(m-Tolyl)oxazole-4-carboxylic acid | N-(2-(4-Amino-1H-pyrazol-1-yl)ethyl)-4-methoxypyridin-2-amine | 419.2 0.73 |
| 16 | 5-m-Tolyl-oxazole-4-carboxylic acid {1-[2-(2,3-dihydro-indol-1-yl)-ethyl]-1H-pyrazol-4-yl}-amide | 5-(m-Tolyl)oxazole-4-carboxylic acid | 1-(2-(Indolin-1-yl)ethyl)-1H-pyrazol-4-amine | 414.3 1.13 |
| 17 | 5-(3-Pyrrolidin-1-yl-phenyl)-oxazole-4-carboxylic acid {1-[2-(4,6-dimethoxy-pyrimidin-2-ylamino)-ethyl]-1H-pyrazol-4-yl}-amide | 5-(3-(Pyrrolidin-1-yl)phenyl)oxazole-4-carboxylic acid | [2-(4-Amino-pyrazol-1-yl)-ethyl]-(4,6-dimethoxy-pyrimidin-2-yl)-amine | 505.3 1.01 |
| 18 | 5-(3-Morpholin-4-yl-phenyl)-oxazole-4-carboxylic acid {1-[2-(4,6-dimethoxy-pyrimidin-2-ylamino)-ethyl]-1H-pyrazol-4-yl}-amide | 5-(3-Morpholinophenyl)oxazole-4-carboxylic acid | [2-(4-Amino-pyrazol-1-yl)-ethyl]-(4,6-dimethoxy-pyrimidin-2-yl)-amine | 521.3 0.85 |
| 19 | 5-m-Tolyl-oxazole-4-carboxylic acid [1-(3-indol-1-yl-propyl)-1H-pyrazol-4-yl]-amide | 5-(m-Tolyl)oxazole-4-carboxylic acid | 1-(3-Indol-1-yl-propyl)-1H-pyrazol-4-ylamine | 426.3 1.16 |
| 20 | 5-m-Tolyl-oxazole-4-carboxylic acid {1-[2-(4,5-dimethoxy-pyrimidin-2-ylamino)-ethyl]-1H-pyrazol-4-yl}-amide | 5-(m-Tolyl)oxazole-4-carboxylic acid | [2-(4-Amino-pyrazol-1-yl)-ethyl]-(4,5-dimethoxy-pyrimidin-2-yl)-amine | 450.3 0.75 |
| 21 | 5-m-Tolyl-oxazole-4-carboxylic acid {1-[3-(5-methoxy-2,3-dihydro-indol-1-yl)-propyl]-1H-pyrazol-4-yl}-amide | 5-(m-Tolyl)oxazole-4-carboxylic acid | 1-[3-(5-Methoxy-2,3-dihydro-indol-1-yl)-propyl]-1H-pyrazol-4-ylamine | 458.3 0.99 |
| 22 | 5-m-Tolyl-oxazole-4-carboxylic acid {1-[3-(6-methoxy-2,3-dihydro-indol-1-yl)-propyl]-1H-pyrazol-4-yl}-amide | 5-(m-Tolyl)oxazole-4-carboxylic acid | 1-[3-(6-Methoxy-2,3-dihydro-indol-1-yl)-propyl]-1H-pyrazol-4-ylamine | 458.3 1.15 |
| 23 | 5-Pyrimidin-4-yl-oxazole-4-carboxylic acid {1-[2-(4,6-dimethoxy-pyrimidin-2-ylamino)-ethyl]-1H-pyrazol-4-yl}-amide | 5-(Pyrimidin-4-yl)oxazole-4-carboxylic acid | [2-(4-Amino-pyrazol-1-yl)-ethyl]-(4,6-dimethoxy-pyrimidin-2-yl)-amine | 438.3 0.96 |
| 24 | 5-(3,4-Dimethyl-phenyl)-oxazole-4-carboxylic acid {1-[2-(5-methoxy-1H-indol-3-yl)-ethyl]-1H-pyrazol-4-yl}-amide | 5-(3,4-Dimethylphenyl)oxazole-4-carboxylic acid | 1-[2-(5-Methoxy-1H-indol-3-yl)-ethyl]-1H-pyrazol-4-ylamine | 456.3 1.07 |
| 25 | 5-(3-Methoxy-4-methyl-phenyl)-oxazole-4-carboxylic acid {1-[2-(5-methoxy-1H-indol-3-yl)-ethyl]-1H-pyrazol-4-yl}-amide | 5-(3-Methoxy-4-methylphenyl)oxazole-4-carboxylic acid | 1-[2-(5-Methoxy-1H-indol-3-yl)-ethyl]-1H-pyrazol-4-ylamine | 472.3 1.06 |
| 26 | 5-(3-Fluoro-phenyl)-oxazole-4-carboxylic acid {1-[2-(5-methoxy-1H-indol-3-yl)-ethyl]-1H-pyrazol-4-yl}-amide | 5-(3-Fluorophenyl)oxazole-4-carboxylic acid | 1-[2-(5-Methoxy-1H-indol-3-yl)-ethyl]-1H-pyrazol-4-ylamine | 446.2 0.99 |
| 27 | 5-Phenyl-oxazole-4-carboxylic acid {1-[2-(5-methoxy-1H-indol-3-yl)-ethyl]-1H-pyrazol-4-yl}-amide | 5-Phenyloxazole-4-carboxylic acid | 1-[2-(5-Methoxy-1H-indol-3-yl)-ethyl]-1H-pyrazol-4-ylamine | 428.2 0.96 |
| 28 | 5-(4-Methoxy-phenyl)-oxazole-4-carboxylic acid {1-[2-(5-methoxy-1H-indol-3-yl)-ethyl]-1H-pyrazol-4-yl}-amide | 5-(4-Methoxyphenyl)oxazole-4-carboxylic acid | 1-[2-(5-Methoxy-1H-indol-3-yl)-ethyl]-1H-pyrazol-4-ylamine | 458.3 0.96 |
| 29 | 5-(2-Fluoro-phenyl)-oxazole-4-carboxylic acid {1-[2-(5-methoxy-1H-indol-3-yl)-ethyl]-1H-pyrazol-4-yl}-amide | 5-(2-Fluorophenyl)oxazole-4-carboxylic acid | 1-[2-(5-Methoxy-1H-indol-3-yl)-ethyl]-1H-pyrazol-4-ylamine | 446.2 0.91 |

TABLE 1-continued

| Example No. | Compound of Formula (I) | Starting Material A | Starting Material B | MS-data m/z [M + H]+ t<sub>R</sub> [min] Method D |
|---|---|---|---|---|
| 30 | 5-m-Tolyl-thiazole-4-carboxylic acid {1-[2-(5-methoxy-1H-indol-3-yl)-ethyl]-1H-pyrazol-4-yl}-amide | 5-(m-Tolyl)thiazole-4-carboxylic acid | 1-[2-(5-Methoxy-1H-indol-3-yl)-ethyl]-1H-pyrazol-4-ylamine | 458.2 1.01 |
| 31 | 5-(3,4-Dimethyl-phenyl)-oxazole-4-carboxylic acid {1-[2-(5,6-dimethoxy-indol-1-yl)-ethyl]-1H-pyrazol-4-yl}-amide | 5-(3,4-Dimethylphenyl)oxazole-4-carboxylic acid | 1-[2-(5,6-Dimethoxy-indol-1-yl)-ethyl]-1H-pyrazol-4-ylamine | 486.3 1.06 |
| 32 | 5-(3-Methoxy-4-methyl-phenyl)-oxazole-4-carboxylic acid {1-[2-(5,6-dimethoxy-indol-1-yl)-ethyl]-1H-pyrazol-4-yl}-amide | 5-(3-Methoxy-4-methylphenyl)oxazole-4-carboxylic acid | 1-[2-(5,6-Dimethoxy-indol-1-yl)-ethyl]-1H-pyrazol-4-ylamine | 502.3 1.05 |
| 33 | 5-(3-Fluoro-phenyl)-oxazole-4-carboxylic acid {1-[2-(5,6-dimethoxy indol-1-yl)-ethyl]-1H-pyrazol-4-yl}-amide | 5-(3-Fluorophenyl)oxazole-4-carboxylic acid | 1-[2-(5,6-Dimethoxy-indol-1-yl)-ethyl]-1H-pyrazol-4-ylamine | 476.3 0.98 |
| 34 | 5-Phenyl-oxazole-4-carboxylic acid {1-[2-(5,6-dimethoxy-indol-1-yl)-ethyl]-1H-pyrazol-4-yl}-amide | 5-Phenyloxazole-4-carboxylic acid | 1-[2-(5,6-Dimethoxy-indol-1-yl)-ethyl]-1H-pyrazol-4-ylamine | 458.3 0.95 |
| 35 | 5-(4-Methoxy-phenyl)-oxazole-4-carboxylic acid {1-[2-(5,6-dimethoxy-indol-1-yl)-ethyl]-1H-pyrazol-4-yl}-amide | 5-(4-Methoxyphenyl)oxazole-4-carboxylic acid | 1-[2-(5,6-Dimethoxy-indol-1-yl)-ethyl]-1H-pyrazol-4-ylamine | 488.3 0.96 |
| 36 | 5-(2-Fluoro-phenyl)-oxazole-4-carboxylic acid {1-[2-(5,6-dimethoxy-indol-1-yl)-ethyl]-1H-pyrazol-4-yl}-amide | 5-(2-Fluorophenyl)oxazole-4-carboxylic acid | 1-[2-(5,6-Dimethoxy-indol-1-yl)-ethyl]-1H-pyrazol-4-ylamine | 476.2 0.9 |
| 37 | 5-(3-Trifluoromethoxy-phenyl)-oxazole-4-carboxylic acid {1-[2-(5-methoxy-1H-indol-3-yl)-ethyl]-1H-pyrazol-4-yl}-amide | 5-(3-(Trifluoromethoxy)phenyl)oxazole-4-carboxylic acid | 1-[2-(5-Methoxy-1H-indol-3-yl)-ethyl]-1H-pyrazol-4-ylamine | 512.3 1.09 |
| 38 | 5-(3-Trifluoromethyl-phenyl)-oxazole-4-carboxylic acid {1-[2-(5-methoxy-1H-indol-3-yl)-ethyl]-1H-pyrazol-4-yl}-amide | 5-(3-(Trifluoromethyl)phenyl)oxazole-4-carboxylic acid | 1-[2-(5-Methoxy-1H-indol-3-yl)-ethyl]-1H-pyrazol-4-ylamine | 496.2 1.07 |
| 39 | 5-(3-Chloro-phenyl)-oxazole-4-carboxylic acid {1-[2-(5-methoxy-1H-indol-3-yl)-ethyl]-1H-pyrazol-4-yl}-amide | 5-(3-Chlorophenyl)oxazole-4-carboxylic acid | 1-[2-(5-Methoxy-1H-indol-3-yl)-ethyl]-1H-pyrazol-4-ylamine | 462.2 1.05 |
| 40 | 5-Biphenyl-3-yl-oxazole-4-carboxylic acid {1-[2-(5-methoxy-1H-indol-3-yl)-ethyl]-1H-pyrazol-4-yl}-amide | 5-([1,1'-Biphenyl]-3-yl)oxazole-4-carboxylic acid | 1-[2-(5-Methoxy-1H-indol-3-yl)-ethyl]-1H-pyrazol-4-ylamine | 504.3 1.13 |
| 41 | 5-(4-Trifluoromethyl-phenyl)-oxazole-4-carboxylic acid {1-[2-(5-methoxy-1H-indol-3-yl)-ethyl]-1H-pyrazol-4-yl}-amide | 5-(4-(Trifluoromethyl)phenyl)oxazole-4-carboxylic acid | 1-[2-(5-Methoxy-1H-indol-3-yl)-ethyl]-1H-pyrazol-4-ylamine | 496.3 1.08 |
| 42 | 5-Phenyl-thiazole-4-carboxylic acid {1-[2-(5-methoxy-1H-indol-3-yl)-ethyl]-1H-pyrazol-4-yl}-amide | 5-Phenylthiazole-4-carboxylic acid | 1-[2-(5-Methoxy-1H-indol-3-yl)-ethyl]-1H-pyrazol-4-ylamine | 444.2 0.95 |
| 43 | 5-(3-Chloro-phenyl)-thiazole-4-carboxylic acid {1-[2-(5-methoxy-1H-indol-3-yl)-ethyl]-1H-pyrazol-4-yl}-amide | 5-(3-Chlorophenyl)thiazole-4-carboxylic acid | 1-[2-(5-Methoxy-1H-indol-3-yl)-ethyl]-1H-pyrazol-4-ylamine | 478.2 1.03 |
| 44 | 5-(3,4-Dimethyl-phenyl)-thiazole-4-carboxylic acid {1-[2-(5-methoxy-1H-indol-3-yl)-ethyl]-1H-pyrazol-4-yl}-amide | 5-(3,4-Dimethylphenyl)thiazole-4-carboxylic acid | 1-[2-(5-Methoxy-1H-indol-3-yl)-ethyl]-1H-pyrazol-4-ylamine | 472.3 1.07 |
| 45 | 5-(6-Methoxy-pyridin-3-yl)-thiazole-4-carboxylic acid {1-[2-(5-methoxy-1H-indol-3-yl)-ethyl]-1H-pyrazol-4-yl}-amide | 5-(6-Methoxypyridin-3-yl)thiazole-4-carboxylic acid | 1-[2-(5-Methoxy-1H-indol-3-yl)-ethyl]-1H-pyrazol-4-ylamine | 475.2 0.9 |
| 66 | 5-m-Tolyl-oxazole-4-carboxylic acid {1-[2-(5-methoxy-1H-indol-3-yl)-ethyl]-1H-imidazol-4-yl}-amide | 5-(m-Tolyl)oxazole-4-carboxylic acid | 1-(2-(5-Methoxy-1H-indol-3-yl)ethyl)-1H-imidazol-4-amine | 442.3 0.86 |
| 144 | 5-(3-Methyl-isoxazol-5-yl)-oxazole-4-carboxylic acid {1-[2-(5-methoxy-1H-indol-3-yl)-ethyl]-1H-pyrazol-4-yl}-amide | 5-(3-methylisoxazol-5-yl)-4,5-dihydrooxazole-4-carboxylic acid | 1-[2-(5-Methoxy-1H-indol-3-yl)-ethyl]-1H-pyrazol-4-ylamine | 433.2 0.85 |

TABLE 1-continued

| Example No. | Compound of Formula (I) | Starting Material A | Starting Material B | MS-data m/z [M + H]+ $t_R$ [min] Method D |
|---|---|---|---|---|
| 145 | 5-Isoxazol-3-yl-oxazole-4-carboxylic acid {1-[2-(5-methoxy-1H-indol-3-yl)-ethyl]-1H-pyrazol-4-yl}-amide | 5-(isoxazol-3-yl)-4,5-dihydrooxazole-4-carboxylic acid | 1-[2-(5-Methoxy-1H-indol-3-yl)-ethyl]-1H-pyrazol-4-ylamine | 419.2 0.79 |

Listed in Table 2 below are example compounds, prepared according to the above-mentioned general procedure B, from the corresponding carboxylic acid (see starting materials A), either readily available or prepared as described above and the corresponding amine (see starting materials B), either readily available or prepared as described above.

Listed in Table 3 below are example compounds, prepared according to the above-mentioned general procedure C, from the pyrazole-analog (see starting materials A) prepared as described above and the corresponding bromo-analog (see starting materials B), either readily available or prepared as described above.

TABLE 2

| Example No. | Compound of Formula (I) | Starting Material A | Starting Material B | MS-data m/z [M+ H]+ $t_R$ [min] Method D |
|---|---|---|---|---|
| 46 | 5-Phenyl-oxazole-4-carboxylic acid {1-[2-(2-methyl-benzoimidazol-1-yl)-ethyl]-1H-pyrazol-4-yl}-amide | 5-Phenyloxazole-4-carboxylic acid | 1-[2-(2-Methyl-benzoimidazol-1-yl)-ethyl]-1H-pyrazol-4-ylamine | 413.2 0.68 |
| 47 | 5-(3,4-Dimethyl-phenyl)-oxazole-4-carboxylic acid {1-[2-(2-methyl-benzoimidazol-1-yl)-ethyl]-1H-pyrazol-4-yl}-amide | 5-(3,4-Dimethylphenyl)oxazole-4-carboxylic acid | 1-[2-(2-Methyl-benzoimidazol-1-yl)-ethyl]-1H-pyrazol-4-ylamine | 441.3 0.79 |
| 48 | 5-(3-Methoxy-4-methyl-phenyl)-oxazole-4-carboxylic acid {1-[2-(2-methyl-benzoimidazol-1-yl)-ethyl]-1H-pyrazol-4-yl}-amide | 5-(3-Methoxy-4-methylphenyl)oxazole-4-carboxylic acid | 1-[2-(2-Methyl-benzoimidazol-1-yl)-ethyl]-1H-pyrazol-4-ylamine | 457.3 0.78 |
| 49 | 5-(3,4-Dimethyl-phenyl)-oxazole-4-carboxylic acid {1-[2-(4,6-dimethoxy-pyrimidin-2-ylamino)-ethyl]-1H-pyrazol-4-yl}-amide | 5-(3,4-Dimethylphenyl)oxazole-4-carboxylic acid | [2-(4-Amino-pyrazol-1-yl)-ethyl]-(4,6-dimethoxy-pyrimidin-2-yl)-amine | 464.3 0.99 |
| 50 | 5-(3-Methoxy-4-methyl-phenyl)-oxazole-4-carboxylic acid {1-[2-(4,6-dimethoxy-pyrimidin-2-ylamino)-ethyl]-1H-pyrazol-4-yl}-amide | 5-(3-Methoxy-4-methylphenyl)oxazole-4-carboxylic acid | [2-(4-Amino-pyrazol-1-yl)-ethyl]-(4,6-dimethoxy-pyrimidin-2-yl)-amine | 480.3 0.98 |
| 51 | 5-(3-Cyano-phenyl)-oxazole-4-carboxylic acid {1-[2-(4,6-dimethoxy-pyrimidin-2-ylamino)-ethyl]-1H-pyrazol-4-yl}-amide | 5-(3-Cyanophenyl)oxazole-4-carboxylic acid | [2-(4-Amino-pyrazol-1-yl)-ethyl]-(4,6-dimethoxy-pyrimidin-2-yl)-amine | 461.2 0.84 |
| 52 | 5-(3-Fluoro-phenyl)-oxazole-4-carboxylic acid {1-[2-(4,6-dimethoxy-pyrimidin-2-ylamino)-ethyl]-1H-pyrazol-4-yl}-amide | 5-(3-Fluorophenyl)oxazole-4-carboxylic acid | [2-(4-Amino-pyrazol-1-yl)-ethyl]-(4,6-dimethoxy-pyrimidin-2-yl)-amine | 454.3 0.91 |
| 53 | 5-(2-Fluoro-phenyl)-oxazole-4-carboxylic acid {1-[2-(4,6-dimethoxy-pyrimidin-2-ylamino)-ethyl]-1H-pyrazol-4-yl}-amide | 5-(2-Fluorophenyl)oxazole-4-carboxylic acid | [2-(4-Amino-pyrazol-1-yl)-ethyl]-(4,6-dimethoxy-pyrimidin-2-yl)-amine | 454.3 0.83 |
| 54 | 5-Phenyl-oxazole-4-carboxylic acid {1-[2-(4,6-dimethoxy-pyrimidin-2-ylamino)-ethyl]-1H-pyrazol-4-yl)-amide | 5-Phenyloxazole-4-carboxylic acid | [2-(4-Amino-pyrazol-1-yl)-ethyl]-(4,6-dimethoxy-pyrimidin-2-yl)-amine | 436.2 0.87 |
| 55 | 5-(4-Methoxy-phenyl)-oxazole-4-carboxylic acid {1-[2-(4,6-dimethoxy-pyrimidin-2-ylamino)-ethyl]-1H-pyrazol-4-yl}-amide | 5-(4-Methoxyphenyl)oxazole-4-carboxylic acid | [2-(4-Amino-pyrazol-1-yl)-ethyl]-(4,6-dimethoxy-pyrimidin-2-yl)-amine | 466.2 0.88 |

TABLE 3

| Example No. | Compound of Formula (I) | Starting Material A | Starting Material B | MS-data m/z [M+ H]+ $t_R$ [min] Method D |
|---|---|---|---|---|
| 56 | 5-m-Tolyl-oxazole-4-carboxylic acid {1-[2-(5-methoxy-1H-indol-3-yl)-ethyl]-1H-pyrazol-4-yl}-amide | N-(1H-Pyrazol-4-yl)-5-(m-tolyl)oxazole-4-carboxamide | 3-(2-Bromoethyl)-5-methoxy-1H-indole | 442.3 1.02 |
| 57 | 5-m-Tolyl-oxazole-4-carboxylic acid {1-[2-(1-methyl-1H-indol-3-yl)-ethyl]-1H-pyrazol-4-yl}-amide | N-(1H-Pyrazol-4-yl)-5-(m-tolyl)oxazole-4-carboxamide | 3-(2-Bromo-ethyl)-1-methyl-1H-indole | 426.3 1.13 |
| 58 | 5-m-Tolyl-oxazole-4-carboxylic acid {1-[2-(1H-indol-3-yl)-ethyl]-1H-pyrazol-4-yl}-amide | N-(1H-Pyrazol-4-yl)-5-(m-tolyl)oxazole-4-carboxamide | 3-(2-Bromoethyl)-1H-indole | 412.2 1.05 |
| 59 | 5-m-Tolyl-oxazole-4-carboxylic acid {1-[2-(6-methoxy-1H-indol-3-yl)-ethyl]-1H-pyrazol-4-yl}amide | N-(1H-Pyrazol-4-yl)-5-(m-tolyl)oxazole-4-carboxamide | 3-(2-Bromo-ethyl)-6-methoxy-1H-indole | 442.3 1.03 |
| 60 | 5-m-Tolyl-oxazole-4-carboxylic acid {1-[2-(6-methoxy-1-methyl-1H-indol-3-yl)-ethyl]-1H-pyrazol-4-yl}-amide | N-(1H-Pyrazol-4-yl)-5-(m-tolyl)oxazole-4-carboxamide | 3-(2-Bromoethyl)-6-methoxy-1-methyl-1H-indole | 456.3 1.11 |
| 61 | 5-m-Tolyl-oxazole-4-carboxylic acid {1-[2-(5-methoxy-1-methyl-1H-indol-3-yl)-ethyl]-1H-pyrazol-4-yl}-amide | N-(1H-Pyrazol-4-yl)-5-(m-tolyl)oxazole-4-carboxamide | 3-(2-Bromoethyl)-5-methoxy-1-methyl-1H-indole | 456.3 1.11 |
| 62 | 5-m-Tolyl-oxazole-4-carboxylic acid {1-[2-(5-fluoro-1H-indol-3-yl)-ethyl]-1H-pyrazol-4-yl}-amide | N-(1H-Pyrazol-4-yl)-5-(m-tolyl)oxazole-4-carboxamide | 3-(2-Bromo-ethyl)-5-fluoro-1H-indole | 430.3 1.05 |
| 63 | 5-m-Tolyl-oxazole-4-carboxylic acid {1-[2-(5-methoxy-1H-pyrrolo[3,2-b]pyridin-3-yl)-ethyl]-1H-pyrazol-4-yl}-amide | N-(1H-Pyrazol-4-yl)-5-(m-tolyl)oxazole-4-carboxamide | 3-(2-Bromoethyl)-5-methoxy-1H-pyrrolo[3,2-b]pyridine | 443.3 0.86 |
| 64 | 5-m-Tolyl-oxazole-4-carboxylic acid {1-[2-(6-methoxy-benzoimidazol-1-yl)-ethyl]-1H-pyrazol-4-yl}amide | N-(1H-Pyrazol-4-yl)-5-(m-tolyl)oxazole-4-carboxamide | 1-(2-Bromoethyl)-6-methoxy-1H-benzo[d]imidazole | 443.3 0.75 |
| 65 | 5-m-Tolyl-oxazole-4-carboxylic acid {1-[2-(4-methoxy-1H-indol-3-yl)-ethyl]-1H-pyrazol-4-yl}amide | N-(1H-Pyrazol-4-yl)-5-(m-tolyl)oxazole-4-carboxamide | 3-(Bromomethyl)-4-methoxy-1H-indole | 442.3 1.08 |

Listed in Table 4 below are example compounds, prepared according to the above-mentioned general procedure D, from the pyrazole-analog (see starting materials A), prepared as described above and the methylsulfonyl-analog (see starting materials B), prepared as described above.

TABLE 4

| Example No. | Compound of Formula (I) | Starting Material A | Starting Material B | MS-data m/z [M + H]+ $t_R$ [min] Method D |
|---|---|---|---|---|
| 67 | 5-m-Tolyl-oxazole-4-carboxylic acid {1-[3-(4,6-dimethoxy-pyrimidin-2-yl)-propyl]-1H-pyrazol-4-yl}-amide | N-(1H-Pyrazol-4-yl)-5-(m-tolyl)oxazole-4-carboxamide | 3-(4,6-Dimethoxypyrimidin-2-yl)propyl methanesulfonate | 449.3 1.04 |
| 68 | 5-m-Tolyl-oxazole-4-carboxylic acid {1-[3-(4-ethoxy-6-methoxy-pyrimidin-2-yl)-propyl]-1H-pyrazol-4-yl}-amide | N-(1H-Pyrazol-4-yl)-5-(m-tolyl)oxazole-4-carboxamide | 3-(4-Ethoxy-6-methoxypyrimidin-2-yl)propyl methanesulfonate | 463.3 1.1 |

Listed in Table 5 below are example compounds, prepared according to the above-mentioned general procedure E, from the sulfonyl-analog of structure 36 (see starting materials A (in table 5, 36a refers to 2-(4-(5-(m-tolyl)oxazole-4-carboxamido)-1H-pyrazol-1-yl)ethyl methanesulfonate, 36b refers to 2-(4-(5-(m-tolyl)oxazole-4-carboxamido)-1H-pyrazol-1-yl)ethyl 4-methylbenzenesulfonate) and 36c refers to 2-(3,5-dimethyl-4-(5-(m-tolyl)oxazole-4-carboxamido)-1H-pyrazol-1-yl)ethyl 4-methylbenzenesulfonate), prepared as described above and nucleophiles (see starting materials B), either readily available or prepared according to literature.

TABLE 5

| Example No. | Compound of Formula (I) | Starting Material A | Starting Material B | MS-data m/z [M + H]+ t_R [min] Method D |
|---|---|---|---|---|
| 69 | 5-m-Tolyl-oxazole-4-carboxylic acid {1-[2-(benzo[1,3]dioxol-5-yloxy)-ethyl]-1H-pyrazol-4-yl}-amide | 36a | Benzo[d][1,3]dioxol-5-ol | 433.2 1.04 |
| 70 | 5-m-Tolyl-oxazole-4-carboxylic acid {1-[2-(benzooxazol-2-ylsulfanyl)-ethyl]-1H-pyrazol-4-yl}-amide | 36b | Benzo[d]oxazole-2-thiol | 446.2 1.11 |
| 71 | 5-m-Tolyl-oxazole-4-carboxylic acid {1-[2-(2-methyl-benzooxazol-6-yloxy)-ethyl]-1H-pyrazol-4-yl}-amide | 36b | 2-Methylbenzo[d]oxazol-6-ol | 444.3 0.98 |
| 72 | 5-m-Tolyl-oxazole-4-carboxylic acid [1-(2-indol-1-yl-ethyl)-1H-pyrazol-4-yl]-amide | 36b | 1H-Indole | 412.3 1.1 |
| 73 | 5-m-Tolyl-oxazole-4-carboxylic acid {1-[2-(1-methyl-5-trifluoromethyl-1H-pyrazol-3-yloxy)-ethyl]-1H-pyrazol-4-yl)-amide | 36b | 5-(Trifluoromethyl)-1H-pyrazol-3-ol | 461.2 1.08 |
| 74 | 5-m-Tolyl-oxazole-4-carboxylic acid {1-[2-(6-fluoro-indol-1-yl)-ethyl]-1H-pyrazol-4-yl}-amide | 36b | 6-Fluoro-1H-indole | 430.3 1.11 |
| 75 | 5-m-Tolyl-oxazole-4-carboxylic acid {1-[2-(7-fluoro-indol-1-yl)-ethyl]-1H-pyrazol-4-yl}-amide | 36b | 7-Fluoro-1H-indole | 430.2 1.14 |
| 76 | 5-m-Tolyl-oxazole-4-carboxylic acid [1-(2-benzoimidazol-1-yl-ethyl)-1H-pyrazol-4-yl]amide | 36b | 1H-Benzo[d]imidazole | 413.2 0.73 |
| 77 | 5-m-Tolyl-oxazole-4-carboxylic acid {1-[2-(5-methyl-indol-111)-ethyl]-1H-pyrazol-4-yl}-amide | 36b | 5-Methyl-1H-indole | 426.3 1.15 |
| 78 | 5-m-Tolyl-oxazole-4-carboxylic acid {1-[2-(6-methoxy-pyrrolo[2,3-b]pyridin-1-yl)-ethyl]-1H-pyrazol-4-yl}-amide | 36b | 6-Methoxy-1H-pyrrolo[2,3-b]pyridine | 443.2 1.11 |
| 79 | 5-m-Tolyl-oxazole-4-carboxylic acid {1-[2-(4-methoxy-pyrrolo[2,3-b]pyridin-1yl)-ethyl]-1H-pyrazol-4-yl}-amide | 36b | 4-Methoxy-1H-pyrrolo[2,3-b]pyridine | 443.3 0.81 |
| 80 | 5-m-Tolyl-oxazole-4-carboxylic acid {1-[2-(2,4-dimethoxy-pyrrolo[2,3-d]pyrimidin-7-yl)-ethyl]-1H-pyrazol-4-yl}-amide | 36b | 2,4-Dimethoxy-7H-pyrrolo[2,3-d]pyrimidine | 474.1* 1.01* |
| 81 | 5-m-Tolyl-oxazole-4-carboxylic acid {1-[2-(5-methyl-pyridin-2-yloxy)-ethyl]-1H-pyrazol-4-yl)-amide | 36b | 5-Methyl pyridin-2-ol | 404.3 1.03 |
| 82 | 5-m-Tolyl-oxazole-4-carboxylic acid {1-[2-(3-fluoro-phenoxy)-ethyl]-1H-pyrazol-4-yl)-amide | 36b | 3-Fluorophenol | 407.2 1.09 |
| 83 | 5-m-Tolyl-oxazole-4-carboxylic acid {1-[2-(4,6-dimethoxy-indol-1-yl)-ethyl]-1H-pyrazol-4-yl)-amide | 36b | 4,6-Dimethoxy-1H-indole | 472.3 1.07 |
| 84 | 5-m-Tolyl-oxazole-4-carboxylic acid {1-[2-(4-fluoro-phenoxy)-ethyl]-1H-pyrazol-4-yl)-amide | 36b | 4-Fluorophenol | 407.2 1.08 |
| 85 | 5-m-Tolyl-oxazole-4-carboxylic acid {1-[2-(7-methyl-indol-111)-ethyl]-1H-pyrazol-4-yl)-amide | 36b | 7-Methyl-1H-indole | 426.2 1.15 |
| 86 | 5-m-Tolyl-oxazole-4-carboxylic acid {1-[2-(4,6-dimethyl-pyridin-2-yloxy)-ethyl]-1H-pyrazol-4-yl)-amide | 36b | 4,6-Dimethylpyridin-2-ol | 418.3 1.01 |
| 87 | 5-m-Tolyl-oxazole-4-carboxylic acid {1-[2-(6-methyl-pyridin-2-yloxy)-ethyl]-1H-pyrazol-4-yl)-amide | 36b | 6-Methyl pyridin-2-ol | 404.3 1.02 |
| 88 | 5-m-Tolyl-oxazole-4-carboxylic acid [1-(2-pyrrolo[2,3-b]pyridin-1-yl-ethyl)-1H-pyrazol-4-yl]-amide | 36b | 1H-Pyrrolo[2,3-b]pyridine | 413.2 0.92 |
| 89 | 5-m-Tolyl-oxazole-4-carboxylic acid {1-[2-(5-fluoro-pyridin-2-yloxy)-ethyl]-1H-pyrazol-4-yl)-amide | 36b | 5-Fluoropyridin-2-ol | 408.2 1.02 |
| 90 | 5-m-Tolyl-oxazole-4-carboxylic acid {1-[2-(4-methyl-pyridin-2-yloxy)-ethyl]-1H-pyrazol-4-yl)-amide | 36b | 4-Methyl pyridin-2-ol | 404.2 1.01 |
| 91 | 5-m-Tolyl-oxazole-4-carboxylic acid {1-[2-(6-chloro-pyrrolo[2,3-b]pyridin-1-yl)-ethyl]-1H-pyrazol-4-yl}-amide | 36b | 6-Chloro-1H-pyrrolo[2,3-b]pyridine | 447.2 1.1 |
| 92 | 5-m-Tolyl-oxazole-4-carboxylic acid {1-[2-(4,6-dimethoxy-pyrrolo[2,3-b]pyridin-1-yl)-ethyl]-1H-pyrazol-4-yl)-amide | 36b | 4,6-Dimethoxy-1H-pyrrolo[2,3-b]pyridine | 473.3 1.1 |
| 93 | 5-m-Tolyl-oxazole-4-carboxylic acid {1-[2-(5-methoxy-pyrrolo[2,3-c]pyridin-1-yl)-ethyl]-1H-pyrazol-4-yl)-amide | 36b | 5-Methoxy-1H-pyrrolo[2,3-c]pyridine | 443.3 0.71 |
| 94 | 5-m-Tolyl-oxazole-4-carboxylic acid {1-[2-(6-methoxy-purin-9-yl)-ethyl]-1H-pyrazol-4-yl)-amide | 36b | 6-Methoxy-9H-purine | 445.3 0.82 |
| 95 | 5-m-Tolyl-oxazole-4-carboxylic acid {1-[2-(6-methoxy-purin-7-yl)-ethyl]-1H-pyrazol-4-yl)-amide | 36b | 6-Methoxy-7H-purine | 445.3 0.79 |
| 96 | 5-m-Tolyl-oxazole-4-carboxylic acid [1-(2-indol-1-yl-ethyl)-3,5-dimethyl-1H-pyrazol-4-yl]-amide | 36c | 1H-Indole | 440.3 1.11 |

TABLE 5-continued

| Example No. | Compound of Formula (I) | Starting Material A | Starting Material B | MS-data m/z [M + H]+ $t_R$ [min] Method D |
|---|---|---|---|---|
| 97 | 5-m-Tolyl-oxazole-4-carboxylic acid [1-(2-benzoimidazol-1-yl-ethyl)-3,5-dimethyl-1H-pyrazol-4-yl]-amide | 36c | 1H-Benzo[d]imidazole | 441.3 0.75 |
| 98 | 5-m-Tolyl-oxazole-4-carboxylic acid {1-[2-(5-methoxy-pyrrolo[2,3-c]pyridin-1-yl)-ethyl]-3,5-dimethyl-1H-pyrazol-4-yl}-amide | 36c | 5-Methoxy-1H-pyrrolo[2,3-c]pyridine | 471.3 0.72 |
| 99 | 5-m-Tolyl-oxazole-4-carboxylic acid {1-[2-(6-methoxy-pyrrolo[3,2-c]pyridin-1-yl)-ethyl]-3,5-dimethyl-1H-pyrazol-4-yl}-amide | 36c | 6-Methoxy-1H-pyrrolo[3,2-c]pyridine | 471.3 0.67 |
| 100 | 5-m-Tolyl-oxazole-4-carboxylic acid {1-[2-(5,6-dimethoxy-indol-1-yl)-ethyl]-3,5-dimethyl-1H-pyrazol-4-yl}-amide | 36c | 5,6-Dimethoxy-1H-indole | 500.3 1.02 |
| 101 | 5-m-Tolyl-oxazole-4-carboxylic acid {1-[2-(6-methoxy-pyrrolo[3,2-c]pyridin-1-yl)-ethyl]-1H-pyrazol-4-yl}-amide | 36b | 6-Methoxy-1H-pyrrolo[3,2-c]pyridine | 443.3 0.66 |
| 102 | 5-m-Tolyl-oxazole-4-carboxylic acid {1-[2-(5,6-dimethoxy-benzoimidazol-1-yl)-ethyl]-1H-pyrazol-4-yl}-amide | 36b | 5,6-Dimethoxy-1H-benzo[d]imidazole | 473.3 0.73 |
| 103 | 5-m-Tolyl-oxazole-4-carboxylic acid [1-(2-pyrrolo[3,2-b]pyridin-1-yl-ethyl)-1H-pyrazol-4-yl]-amide | 36b | 1H-Pyrrolo[3,2-c]pyridine | 413.3 0.62 |
| 104 | 5-m-Tolyl-oxazole-4-carboxylic acid {1-[2-(5-methoxy-indol-1-yl)-ethyl]-1H-pyrazol-4-yl}-amide | 36b | 5-Methoxy-1H-indole | 442.3 1.07 |
| 105 | 5-m-Tolyl-oxazole-4-carboxylic acid {1-[2-(6-methoxy-indol-1-yl)-ethyl]-1H-pyrazol-4-yl}-amide | 36b | 6-Methoxy-1H-indole | 442.3 1.08 |
| 106 | 5-m-Tolyl-oxazole-4-carboxylic acid {1-[2-(5,6-dichloro-indol-1-yl)-ethyl]-1H-pyrazol-4-yl}-amide | 36b | 5,6-Dichloro-1H-indole | 480.2 1.21 |
| 107 | 5-m-Tolyl-oxazole-4-carboxylic acid {1-[2-(5-chloro-indol-1-yl)-ethyl]-1H-pyrazol-4-yl}-amide | 36b | 5-Chloro-1H-indole | 446.2 1.16 |
| 108 | 5-m-Tolyl-oxazole-4-carboxylic acid {1-[2-(5-chloro-6-methoxy-indol-1-yl)-ethyl]-1H-pyrazol-4-yl}-amide | 36b | 5-Chloro-6-methoxy-1H-indole | 476.2 1.13 |
| 109 | 5-m-Tolyl-oxazole-4-carboxylic acid {1-[2-(3-phenyl-pyrrol-1-yl)-ethyl]-1H-pyrazol-4-yl}-amide | 36b | 3-Phenyl-1H-pyrrole (Organic Letters 2002, Vol. 4, No. 20, p. 3537-3539) | 438.3 1.14 |

*=LC/MS conditions B. 36a=2-(4-(5-(m-tolyl)oxazole-4-carboxamido)-1H-pyrazol-1-yl)ethyl methanesulfonate, 36b=2-(4-(5-(m-tolyl)oxazole-4-carboxamido)-1H-pyrazol-1-yl)ethyl-4-methylbenzenesulfonate) and 36c=2-(3,5-dimethyl-4-(5-(m-tolyl)oxazole-4-carboxamido)-1H-pyrazol-1-yl)ethyl 4-methyl benzenesulfonate Listed in Table 6 below are example compounds, prepared according to the above-mentioned general procedure F, G, H, I and J from Starting Material and Starting Material B, either readily available or prepared as described above.

TABLE 6

| Example No. | Compound of Formula (I) | Starting Material A and Starting Material B | Procedure | MS-data m/z [M + H]+ (R [min] Method D |
|---|---|---|---|---|
| 110 | 5-m-Tolyl-oxazole-4-carboxylic acid {1-[2-(4,6-dimethoxy-pyrimidin-2-ylamino)-ethyl]-1H-pyrazol-4-yl}-amide | N-(1-(2-Aminoethyl)-1H-pyrazol-4-yl)-5-(m-tolyl)oxazole-4-carboxamide and 2-Chloro-4,6-dimethoxypyrimidine | F | 450.3 0.94 |
| 111 | 5-m-Tolyl-oxazole-4-carboxylic acid {1[2-(quinazolin-2-ylamino)-ethyl]-1H-pyrazol-4-yl}-amide | N-(1-(2-Aminoethyl)-1H-pyrazol-4-yl)-5-(m-tolyl)oxazole-4-carboxamide and 2-Chloroquinazoline | F | 440.3 0.79 |
| 112 | 5-m-Tolyl-oxazole-4-carboxylic acid {1-[2-(5-chloro-benzooxazol-2-ylamino)-ethyl]-1H-pyrazol-4-yl}-amide | N-(1-(2-Aminoethyl)-1H-pyrazol-4-yl)-5-(m-tolyl)oxazole-4-carboxamide and 2,5-Dichlorobenzo[d]oxazole | F | 463.2 1.03 |
| 113 | 5-m-Tolyl-oxazole-4-carboxylic acid {1[2-(benzooxazol-2-ylamino)-ethyl]- | N-(1-(2-Aminoethyl)-1H-pyrazol-4-yl)-5-(m-tolyl)oxazole-4- | F | 429.2 0.9 |

TABLE 6-continued

| Example No. | Compound of Formula (I) | Starting Material A and Starting Material B | Procedure | MS-data m/z [M + H]+ (R [min] Method D |
|---|---|---|---|---|
| | 1H-pyrazol-4-yl}-amide | carboxamide and 2-Chlorobenzo[d]oxazole | | |
| 114 | 5-m-Tolyl-oxazole-4-carboxylic acid {1-[2-(5-methyl-pyrimidin-2-ylamino)-ethyl]-1H-pyrazol-4-yl)-amide | N-(1-(2-Aminoethyl)-1H-pyrazol-4-yl)-5-(m-tolyl)oxazole-4-carboxamide and 2-Chloro-5-methyl pyrimidine | F | 404.3 0.79 |
| 115 | 5-m-Tolyl-oxazole-4-carboxylic acid {1[2-(quinoxalin-2-ylamino)-ethyl]-1H-pyrazol-4-yl}-amide | N-(1-(2-Aminoethyl)-1H-pyrazol-4-yl)-5-(m-tolyl)oxazole-4-carboxamide and 2-Chloroquinoxaline | F | 440.3 0.9 |
| 116 | 5-m-Tolyl-thiazole-4-carboxylic acid {1[2-(benzooxazol-2-ylamino)-ethyl]-1H-pyrazol-4-yl}-amide | N-(1-(2-Aminoethyl)-1H-pyrazol-4-yl)-5-(m-tolyl)thiazole-4-carboxamide and 2-Chlorobenzo[d]oxazole | F | 445.2 0.9 |
| 117 | 5-m-Tolyl-thiazole-4-carboxylic acid {1[2-(quinoxalin-2-ylamino)-ethyl]-1H-pyrazol-4-yl}-amide | N-(1-(2-Aminoethyl)-1H-pyrazol-4-yl)-5-(m-tolyl)thiazole-4-carboxamide and 2-Chloroquinoxaline | F | 456.2 0.9 |
| 118 | 5-m-Tolyl-thiazole-4-carboxylic acid {1-[2-(5-methyl-pyrimidin-2-ylamino)-ethyl]-1H-pyrazol-4-yl}-amide | N-(1-(2-Aminoethyl)-1H-pyrazol-4-yl)-5-(m-tolyl)thiazole-4-carboxamide and 2-Chloro-5-methyl pyrimidine | F | 420.2 0.78 |
| 119 | 5-m-Tolyl-oxazole-4-carboxylic acid {1[2-(pyrimidin-2-ylamino)-ethyl]-1H-pyrazol-4-yl}-amide | N-(1-(2-Aminoethyl)-1H-pyrazol-4-yl)-5-(m-tolyl)oxazole-4-carboxamide and 2-Chloropyrimidine | F | 390.2 0.77 |
| 120 | 5-m-Tolyl-oxazole-4-carboxylic acid {1-[2-(4-methoxy-pyrimidin-2-ylamino)-ethyl]-1H-pyrazol-4-yl)-amide | N-(1-(2-Aminoethyl)-1H-pyrazol-4-yl)-5-(m-tolyl)oxazole-4-carboxamide and 2-Chloro-4-methoxypyrimidine | F | 420.2 0.73 |
| 121 | 5-m-Tolyl-oxazole-4-carboxylic acid {1[2-(quinazolin-2-ylamino)-ethyl]-1H-imidazol-4-yl}-amide | N-(1-(2-Aminoethyl)-1H-imidazol-4-yl)-5-(m-tolyl)oxazole-4-carboxamide and 2-Chloroquinazoline | F | 440.3 0.75 |
| 122 | 5-m-Tolyl-oxazole-4-carboxylic acid {1[2-(benzooxazol-2-ylamino)-ethyl]-1H-imidazol-4-yl}-amide | N-(1-(2-Aminoethyl)-1H-imidazol-4-yl)-5-(m-tolyl)oxazole-4-carboxamide and 2-Chlorobenzo[d]oxazole | F | 429.2 0.81 |
| 123 | 5-m-Tolyl-oxazole-4-carboxylic acid {1-[2-(4,6-dimethyl-pyrimidin-2-ylamino)-ethyl]-1H-pyrazol-4-yl)-amide | N-(1-(2-Aminoethyl)-1H-pyrazol-4-yl)-5-(m-tolyl)oxazole-4-carboxamide and 4,6-Dimethyl-2-(methylsulfonyl)pyrimidine | I | 418.3 0.75 |
| 124 | 5-m-Tolyl-oxazole-4-carboxylic acid {1-[2-(4,6-dimethoxy-5-methyl-pyrimidin-2-ylamino)-ethyl]-1H-pyrazol-4-yl}-amide | N-(1-(2-Aminoethyl)-1H-pyrazol-4-yl)-5-(m-tolyl)oxazole-4-carboxamide and 4,6-Dimethoxy-5-methyl-2-(methylsulfonyl)pyrimidine | I | 464.3 1.15 |
| 125 | 5-m-Tolyl-oxazole-4-carboxylic acid {1-[(R)-2-(4,6-dimethoxy-pyrimidin-2-ylamino)-propyl]-1H-pyrazol-4-yl)-amide | (R)-N-(1-(2-Aminopropyl)-1H-pyrazol-4-yl)-5-(m-tolypoxazole-4-carboxamide and 2-Chloro-4,6-dimethoxypyrimidine | G | 464.3 0.98 |
| 126 | 5-m-Tolyl-oxazole-4-carboxylic acid {1-[(S)-2-(4,6-dimethoxy-pyrimidin-2-ylamino)-propyl]-1H-pyrazol-4-yl)-amide | (S)-N-(1-(2-Aminopropyl)-1H-pyrazol-4-yl)-5-(m-tolypoxazole-4-carboxamide and 2-Chloro-4,6-dimethoxypyrimidine | G | 464.3 0.98 |
| 127 | 5-m-Tolyl-oxazole-4-carboxylic acid {1-[2-(4,6-dimethoxy-pyrimidin-2-ylamino)-ethyl]-1H-imidazol-4-yl)-amide | N-(1-(2-Aminoethyl)-1H-imidazol-4-yl)-5-(m-tolyl)oxazole-4-carboxamide and 2-Chloro-4,6-dimethoxypyrimidine | H | 450.3 0.83 |
| 128 | 5-m-Tolyl-oxazole-4-carboxylic acid {1-[2-(5-bromo-pyrimidin-2-ylamino)-ethyl]-1H-pyrazol-4-yl}-amide | N-(1-(2-Aminoethyl)-1H-pyrazol-4-yl)-5-(m-tolyl)oxazole-4-carboxamide and 5-Bromo-2-chloropyrimidine | H | 468 0.99 |
| 129 | 5-m-Tolyl-oxazole-4-carboxylic acid {1-[2-(2,6-dimethoxy-pyrimidin-4-ylamino)-ethyl]-1H-pyrazol-4-yl)-amide | N-(1-(2-Aminoethyl)-1H-pyrazol-4-yl)-5-(m-tolyl)oxazole-4-carboxamide and 4-Chloro-2,6-dimethoxypyrimidine | H | 450.3 0.83 |
| 130 | 5-m-Tolyl-oxazole-4-carboxylic acid {1-[3-(4,6-dimethoxy-pyrimidin-2-ylamino)-propyl]-1H-pyrazol-4-yl)-amide | N-(1-(3-Aminopropyl)-1H-pyrazol-4-yl)-5-(m-tolyl)oxazole-4-carboxamide and 2-Chloro-4,6-dimethoxypyrimidine | H | 464.3 0.93 |
| 131 | 5-m-Tolyl-oxazole-4-carboxylic acid {1-[3-(4-methoxy-pyrimidin-2- | N-(1-(3-Aminopropyl)-1H-pyrazol-4-yl)-5-(m-tolyl)oxazole-4- | H | 434.3 0.76 |

TABLE 6-continued

| Example No. | Compound of Formula (I) | Starting Material A and Starting Material B | Procedure | MS-data m/z [M + H]+ (R [min] Method D |
|---|---|---|---|---|
| | ylamino)-propyl]-1H-pyrazol-4-yl)-amide | carboxamide and 2-Chloro-4-methoxypyrimidine | | |
| 132 | 5-m-Tolyl-oxazole-4-carboxylic acid {1-[2-(4,6-dimethoxy-pyrimidin-2-yloxy)-ethyl]-1H-pyrazol-4-yl}-amide | N-(1-(2-Hydroxyethyl)-1H-pyrazol-4-yl)-5-(m-tolyl)oxazole-4-carboxamide and 2-Chloro-4,6-dimethoxypyrimidine | J | 451.2 1.02 |
| 133 | 5-m-Tolyl-oxazole-4-carboxylic acid {1[2-(benzooxazol-2-yloxy)-ethyl]-1H-pyrazol-4-yl}-amide | N-(1-(2-Hydroxyethyl)-1H-pyrazol-4-yl)-5-(m-tolyl)oxazole-4-carboxamide and 2-Chlorobenzo[d]oxazole | J | 430.2 1.04 |
| 134 | 5-m-Tolyl-oxazole-4-carboxylic acid {1-[2-(5-methyl-pyrimidin-2-yloxy)-ethyl]-1H-pyrazol-4-yl}-amide | N-(1-(2-Hydroxyethyl)-1H-pyrazol-4-yl)-5-(m-tolyl)oxazole-4-carboxamide and 2-Chloro-5-methyl pyrimidine | J | 405.2 0.91 |
| 135 | 5-m-Tolyl-oxazole-4-carboxylic acid {1[2-(quinazolin-2-yloxy)-ethyl]-1H-pyrazol-4-yl}-amide | N-(1-(2-Hydroxyethyl)-1H-pyrazol-4-yl)-5-(m-tolyl)oxazole-4-carboxamide and 2-Chloroquinazoline | J | 441.1 0.99 |
| 136 | 5-m-Tolyl-oxazole-4-carboxylic acid {1[2-(quinoxalin-2-yloxy)-ethyl]-1H-pyrazol-4-yl}-amide | N-(1-(2-Hydroxyethyl)-1H-pyrazol-4-yl)-5-(m-tolyl)oxazole-4-carboxamide and 2-Chloroquinoxaline | J | 441.3 1.05 |
| 137 | 5-m-Tolyl-oxazole-4-carboxylic acid {1-[2-(4,6-dimethoxy-pyrimidin-2-yloxy)-ethyl]-3,5-dimethyl-1H-pyrazol-4-yl}-amide | N-(1-(2-Hydroxyethyl)-3,5-dimethyl-1H-pyrazol-4-yl)-5-(m-tolyl)oxazole-4-carboxamide and 2-Chloro-4,6-dimethoxypyrimidine | J | 479.3 1.02 |
| 138 | 5-m-Tolyl-oxazole-4-carboxylic acid {1[2-(benzooxazol-2-yloxy)-ethyl]-3,5-dimethyl-1H-pyrazol-4-yl}-amide | N-(1-(2-Hydroxyethyl)-3,5-dimethyl-1H-pyrazol-4-yl)-5-(m-tolyl)oxazole-4-carboxamide and 2-Chlorobenzo[d]oxazole | J | 458.3 1.05 |

Example 139

N-(1-(2-((4,6-dimethoxypyrimidin-2-yl)(ethyl)amino)ethyl)-1H-pyrazol-4-yl)-5-(m-tolyl)oxazole-4-carboxamide To an ice-cooled solution of N-(1-(2-((4,6-dimethoxypyrimidin-2-yl)amino)ethyl)-1H-pyrazol-4-yl)-5-(m-tolyl)oxazole-4-carboxamide (80 mg, 0.178 mmol) in DMF (1 mL) was added NaH (12 mg, 0.27 mmol). The icebath was removed and the mixture was stirred for 40 min at rt, then 1-bromo ethane (20 uL, 0.25 mmol) was added and stirred for 18 h at rt. To the reaction mixture was added few drops of water and directly purified by prep. HPLC. LC-MS conditions D: $t_R$=1.19 min, [M+H]+=478.3.

Example 140

N-(1-(2-((1-methyl-1H-benzo[d]imidazol-2-yl)amino)ethyl)-1H-pyrazol-4-yl)-5-(m-tolyl)oxazole-4-carboxamide To a solution of N-(1-(2-oxoethyl)-1H-pyrazol-4-yl)-5-(m-tolyl)oxazole-4-carboxamide (157 mg, 0.45 mmol) in MeCN (1 mL) and DCM (0.8 mL) was added 1-methyl-1H-benzo[d]imidazol-2-amine (66 mg, 0.45 mmol) followed by STAB (190 mg, 0.90 mmol) and 1 drop of AcOH. After stirring at rt for 18 h, the reaction mixture was filtered and directly purified by prep. HPLC. LC-MS conditions D: $t_R$=0.77 min, [M+H]+=442.3.

Example 141 rac-N-(1-((1-(4,6-dimethoxypyrimidin-2-yl)pyrrolidin-2-yl)methyl)-1H-pyrazol-4-yl)-5-(m-tolyl)oxazole-4-carboxamide To a microwave tube was added rac-N-(1-(pyrrolidin-2-ylmethyl)-1H-pyrazol-4-yl)-5-(m-tolyl)oxazole-4-carboxamide (40 mg, 0.11 mmol), 2-chloro-4,6-dimethoxypyrimidine (18 mg, 0.10 mmol) and $Cs_2CO_3$ (175 mg, 0.228 mmol) in MeCN (0.8 mL). The reaction mixture was irradiated at 180° C. for 30 min in the microwave, then the reaction mixture was diluted with DCM (30 mL). The organic layer was separated and washed with $H_2O$ (5 mL) and brine (5 mL). The combined organic layers were dried ($MgSO_4$), filtered and the solvent was removed under reduced pressure. Purification by FC (hex/EtOAc 3:7) Rf=0.4) yielded the title compound (27 mg) as a yellowish solid. LC-MS conditions D: $t_R$=1.16 min, [M+H]+=490.3.

Example 142

N-(1-(3-(6-methoxy-1H-indol-1-yl)propyl)-1H-pyrazol-4-yl)-5-(m-tolyl)oxazole-4-carboxamide A solution of N-(1-(3-(6-methoxyindolin-1-yl)propyl)-1H-pyrazol-4-yl)-5-(m-tolyl)oxazole-4-carboxamide (69 mg, 0.15 mmol) in acetone (1.0 mL) was added dropwise to a suspension of $MnO_2$ (50 mg, 0.575 mmol) in acetone (0.5 mL). After stirring the dark reaction mixture for 18 h, the mixture was filtered over celite, rinsed with acetone and the solvent was removed under reduced pressure. Purification by prep. HPLC yielded the title compound (11 mg) as a redish solid. LC-MS conditions D: $t_R$=1.14 min, [M+H]+=456.3.

Example 143

N-(1-(3-(5-methoxy-1H-indol-1-yl)propyl)-1H-pyrazol-4-yl)-5-(m-tolyl)oxazole-4-carboxamide A solution of N-(1-(3-(5-methoxyindolin-1-yl)propyl)-1H-pyrazol-4-yl)-5-(m-tolyl)oxazole-4-carboxamide (69 mg, 0.15 mmol) in acetone (1.0 mL) was added dropwise to a suspension of $MnO_2$ (50 mg, 0.575 mmol) in acetone (0.5 mL). After stirring the dark reaction mixture for 18 h, the mixture was filtered over celite, rinsed with acetone and the solvent was removed under reduced pressure. Purification by prep. HPLC yielded the title compound (5 mg) as a brown oil. LC-MS conditions D: $t_R$=1.12 min, $[M+H]^+$=456.3.

II. Biological Assays

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/mL G418, 100 U/mL penicillin, 100 µg/mL streptomycin and 10% heat inactivated fetal calf serum (FCS). The cells are seeded at 20'000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH:water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/l and 20 mM HEPES. On the day of the assay, 50 µl of staining buffer (HBSS containing 1% FCS, 20 mM HEPES, $NaHCO_3$: 0.375 g/l, 5 mM probenecid (Sigma) and 3 µM of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at RT for 30 min before measurement.

Within the Fluorescent Imaging Plate Reader (FLIPR Tetra, Molecular Devices), antagonists are added to the plate in a volume of 10 µl/well, incubated for 120 min or (where explicitly indicated) for 10 min and finally 10 µl/well of agonist is added. Fluorescence is measured for each well at 1 second intervals, and the height of each fluorescence peak is compared to the height of the fluorescence peak induced by 3 nM orexin-A with vehicle in place of antagonist. The $IC_{50}$ value (the concentration of compound needed to inhibit 50% of the agonistic response) is determined and may be normalized using the obtained $IC_{50}$ value of a on-plate reference compound. Optimized conditions were achieved by adjustment of pipetting speed and cell splitting regime. The calculated $IC_{50}$ values may fluctuate depending on the daily cellular assay performance. Fluctuations of this kind are known to those skilled in the art.

Antagonistic activities of example compounds with respect to the $OX_2$ receptor are displayed in Table 7.

TABLE 7

| Example | $IC_{50}$ $OX_2$ [nM] |
|---|---|
| 1 | 984[#] |
| 2 | 1780[#] |
| 3 | 1277[#] |
| 4 | 176 |
| 5 | 471[#] |
| 6 | 1040[#] |
| 7 | 399[#] |
| 8 | 514[#] |
| 9 | 29[#] |
| 10 | 53[#] |
| 11 | 154 |
| 12 | 28 |
| 13 | 502 |
| 14 | 379 |
| 15 | 254 |
| 16 | 368 |
| 17 | 201 |
| 18 | 134 |
| 19 | 389 |
| 20 | 870 |
| 21 | 1830 |
| 22 | 247 |
| 23 | 9020 |
| 24 | 51 |
| 25 | 146 |
| 26 | 6 |
| 27 | 2 |
| 28 | 35 |
| 29 | 7 |
| 30 | 30 |
| 31 | 24 |
| 32 | 110 |
| 33 | 146 |
| 34 | 343 |
| 35 | 233 |
| 36 | 287 |
| 37 | 13 |
| 38 | 16 |
| 39 | 2 |
| 40 | 73 |
| 41 | 594 |
| 42 | 65 |
| 43 | 20 |
| 44 | 225 |
| 45 | 235 |
| 46 | 597 |
| 47 | 757 |
| 48 | 3800 |
| 49 | 51 |
| 50 | 238 |
| 51 | 353 |
| 52 | 25 |
| 53 | 41 |
| 54 | 118 |
| 55 | 100 |
| 56 | 2 |
| 57 | 265 |
| 58 | 236 |
| 59 | 1655 |
| 60 | 665 |
| 61 | 22 |
| 62 | 98 |
| 63 | 15 |
| 64 | 6 |
| 65 | 111 |
| 66 | 27 |
| 67 | 28 |
| 68 | 84 |
| 69 | 414[#] |
| 70 | 110[#] |
| 71 | 949[#] |
| 72 | 86 |
| 73 | 1990[#] |
| 74 | 67[#] |
| 75 | 180[#] |
| 76 | 65 |

TABLE 7-continued

| Example | IC$_{50}$ OX$_2$ [nM] |
|---|---|
| 77 | 204# |
| 78 | 4 |
| 79 | 548# |
| 80 | 94 |
| 81 | 1851# |
| 82 | 931# |
| 83 | 9 |
| 84 | 973# |
| 85 | 376# |
| 86 | 474# |
| 87 | 794# |
| 88 | 136# |
| 89 | 2100# |
| 90 | 2020# |
| 91 | 108# |
| 92 | 65# |
| 93 | 230 |
| 94 | 1081# |
| 95 | 492# |
| 96 | 183 |
| 97 | 457 |
| 98 | 765 |
| 99 | 207 |
| 100 | 472 |
| 101 | 29 |
| 102 | 63 |
| 103 | 297 |
| 104 | 784 |
| 105 | 9 |
| 106 | 81 |
| 107 | 507 |
| 108 | 40 |
| 109 | 864 |
| 110 | 19 |
| 111 | 133# |
| 112 | 5074 |
| 113 | 235# |
| 114 | 2610 |
| 115 | 286# |
| 116 | 237 |
| 117 | 129 |
| 118 | 959# |
| 119 | 1160# |
| 120 | 78# |
| 121 | 328# |
| 122 | 2775# |
| 123 | 262# |
| 124 | 180 |
| 125 | 354 |
| 126 | 270 |
| 127 | 75# |
| 128 | 1160 |
| 129 | 30 |
| 130 | 57 |
| 131 | 43 |
| 132 | 25 |
| 133 | 941# |
| 134 | 869# |
| 135 | 226# |
| 136 | 627# |
| 137 | 1021 |
| 138 | 966 |
| 139 | 631# |
| 140 | 909 |
| 141 | 320 |
| 142 | 47 |
| 143 | 891 |
| 144 | 17 |
| 145 | 53 |

IC$_{50}$ values measured using a compound incubation time of 10 min.

The invention claimed is:
1. A compound of formula (I)

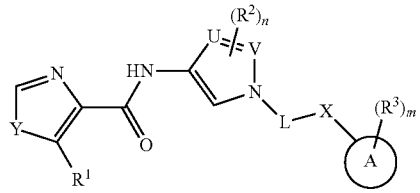

Formula (I)

wherein
R$^1$ represents aryl or 5- to 10-membered heteroaryl, wherein the aryl or 5- to 10-membered heteroaryl independently is unsubstituted, or mono-, di-, or tri-substituted; wherein the substituents are independently selected from the group consisting of:
(C$_{1-4}$)alkyl, (C$_{1-4}$)alkoxy, halogen, cyano, (C$_{1-3}$)fluoroalkyl, (C$_{1-3}$)fluoroalkoxy; and
—NR$^4$R$^5$, wherein R$^4$ and R$^5$ are independently hydrogen or (C$_{1-4}$)alkyl; or R$^4$ and R$^5$ together with the nitrogen atom to which they are attached to form a saturated 5- to 7-membered ring optionally containing an oxygen atom; and
phenyl or 5- or 6-membered heteroaryl, wherein the phenyl or 5- or 6-membered heteroaryl independently is unsubstituted, or mono-, or di-substituted; wherein the substituents are independently selected from the group consisting of (C$_{1-4}$)alkyl, (C$_{1-4}$)alkoxy, halogen, cyano, (C$_{1-3}$)fluoroalkyl, (C$_{1-3}$)fluoroalkoxy;
wherein at maximum one substituent selected from —NR$^4$R$^5$ and phenyl or 5- or 6-membered heteroaryl is present;
U represents CH, and V represents N; or U represents N and V represents CH;
(R$^2$)$_n$ represents one or two optional substituents, wherein each R$^2$ independently is (C$_{1-3}$)alkyl; and
Y represents O or S; and
ring A represents aryl or 5- to 10-membered heteroaryl, wherein said aryl or 5- to 10-membered heteroaryl independently is optionally substituted with (R$^3$)$_m$; wherein
(R$^3$)$_m$ represents one, two or three optional substituents, wherein each R$^3$ independently is selected from the group consisting of:
(C$_{1-4}$)alkyl, (C$_{1-4}$)alkoxy, halogen, cyano, (C$_{1-3}$)fluoroalkyl, (C$_{1-3}$)fluoroalkoxy; and
phenyl or 5- or 6-membered heteroaryl, wherein the phenyl or 5- or 6-membered heteroaryl independently is unsubstituted, or mono-, or di-substituted; wherein the substituents are independently selected from the group consisting of (C$_{1-4}$)alkyl, (C$_{1-4}$)alkoxy, halogen, cyano, (C$_{1-3}$)fluoroalkyl, (C$_{1-3}$)fluoroalkoxy;
wherein at maximum one phenyl or 5- or 6-membered heteroaryl substituent is present;
or (R$^3$)$_m$ represents two substituents which form a non-aromatic 5- or 6-membered ring fused to ring A, wherein said 5- or 6-membered ring optionally contains one or two oxygen atoms;
L represents a group —(CH$_2$)$_m$—, wherein m represents the integer 2 or 3; wherein said group L is optionally substituted with R$^6$; wherein R$^6$, if present, represents (C$_{1-3}$)alkyl; and
X represents a direct bond, O, S or NR$^7$;

wherein, in case X represents NR$^7$,
  R$^7$ represents hydrogen or (C$_{1-3}$)alkyl; or, additionally, R$^7$ and R$^6$ may form a 5- to 7-membered saturated ring including the nitrogen to which R$^7$ is attached to; or
  R$^7$ together with one of the substituents R$^3$ may form a non-aromatic 5- to 7-membered ring including the nitrogen to which R$^7$ is attached to, which ring is fused to ring A; wherein R$^6$ is absent; and the remaining of said substituents R$^3$, if present, independently are selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy;
or a salt thereof.

2. A compound according to claim 1; wherein R$^1$ represents phenyl which is unsubstituted, or mono-, or di-substituted; wherein the substituents are independently selected from the group consisting of (C$_{1-4}$)alkyl, (C$_{1-4}$)alkoxy, halogen, cyano, (C$_{1-3}$)fluoroalkyl, (C$_{1-3}$)fluoroalkoxy;
or a salt thereof.

3. A compound according to claim 1; wherein U represents CH, and V represents N;
or a salt thereof.

4. A compound according to claim 1; wherein Y represents O;
or a salt thereof.

5. A compound according to claim 1; wherein L represents a group —(CH$_2$)$_m$—, wherein m represents the integer 2 or 3; wherein, in case m represents the integer 2, said group L is optionally substituted at the carbon atom which is adjacent to X with R$^6$; wherein R$^6$, if present, represents methyl; or, in case X represents NR$^7$, R$^7$ and R$^6$ additionally may form a piperidine or a pyrrolidine ring including the nitrogen to which R$^7$ is attached to;
or a salt thereof.

6. A compound according to claim 1; wherein ring A represents aryl or 5- to 10-membered heteroaryl, wherein said aryl or 5- to 10-membered heteroaryl independently is optionally substituted with (R$^3$)$_m$; wherein
  (R$^3$)$_m$ represents one, two or three optional substituents, wherein each R$^3$ independently is selected from the group consisting of:
    (C$_{1-4}$)alkyl, (C$_{1-4}$)alkoxy, halogen, cyano, (C$_{1-3}$)fluoroalkyl, and (C$_{1-3}$)fluoroalkoxy; and phenyl
    wherein at maximum one phenyl substituent is present;
  or (R$^3$)$_m$ represents two substituents which form a fragment —O—(CH$_2$)$_q$—O—, wherein q represents the integer 1 or 2;
  or, in case X represents NR$^7$, (R$^3$)$_m$ additionally may represent one substituent, wherein R$^7$ together with said substituent R$^3$ forms a non-aromatic 5- to 7-membered ring including the nitrogen to which R$^7$ is attached to, which ring is fused to ring A;
or a salt thereof.

7. A compound according to claim 1; wherein X represents a direct bond, O or NR$^7$;
or a salt thereof.

8. A compound according to claim 1; wherein, in case X represents NR$^7$,
  R$^7$ represents hydrogen or (C$_{1-3}$)alkyl; or, additionally, R$^7$ and R$^6$ may form a piperidine or a pyrrolidine ring including the nitrogen to which R$^7$ is attached to; or
  X being NR$^7$ together with (R$^3$)$_m$ and ring A represents 2,3-dihydro-indol-1-yl;
or a salt thereof.

9. A compound according to claim 1; wherein
  L represents a group —(CH$_2$)$_m$—, wherein m represents the integer 2 or 3;
  X represents a direct bond; and
  ring A represents a group selected from the group consisting of pyrrol-1-yl, imidazol-1-yl, pyrazol-1-yl, triazol-1-yl, indol-1-yl, isoindol-2-yl, indazol-1-yl, benzimidazol-1-yl, benzotriazol-1-yl, 1H-pyrrolo[3,2-b]pyridin-1-yl, 1H-pyrrolo[2,3-b]pyridin-1-yl, 1H-pyrrolo[3,2-c]pyridin-1-yl, 1H-pyrrolo[2,3-c]pyridin-1-yl, 7H-pyrrolo[2,3-d]pyrimidin-7-yl, 5H-pyrrolo[3,2-d]pyrimidin-5-yl, 4H-furo[3,2-b]pyrrol-4-yl, 7H-purin-7-yl, and 9H-purin-9-yl; wherein each of said groups independently is optionally substituted with (R$^3$)$_m$; wherein (R$^3$)$_m$ represents one, or two optional substituents, wherein each R$^3$ independently is selected from the group consisting of (C$_{1-4}$)alkyl, (C$_{1-4}$)alkoxy, and halogen; or
  L represents a group —(CH$_2$)$_m$—, wherein m represents the integer 2 or 3;
  X represents a direct bond; and
  ring A represents a group selected from the group consisting of pyrimidin-2-yl, indol-3-yl, and 1H-pyrrolo[3,2-b]pyridin-3-yl; wherein each of said groups independently is optionally substituted with (R$^3$)$_m$; wherein (R$^3$)$_m$ represents one, or two optional substituents, wherein each R$^3$ independently is selected from the group consisting of (C$_{1-4}$)alkyl, (C$_{1-4}$)alkoxy, and halogen; or
  L represents a group —(CH$_2$)$_m$—, wherein m represents the integer 2 or 3;
  X represents a O or NR$^7$;
  R$^7$ represents hydrogen or (C$_{1-3}$)alkyl; and
  ring A represents a group selected from the group consisting of oxazol-2-yl, thiazol-2-yl, imidazol-2-yl, pyrazol-3-yl, pyridin-2-yl, pyrimid-2-yl, pyrimid-4-yl, pyridazin-3-yl, pyrazin-2-yl, benzimidazol-2-yl, benzoxazol-2-yl, benzothiazol-2-yl, quinolin-2-yl, quinazolin-2-yl, and quinoxalin-2-yl; wherein each of said groups independently is optionally substituted with (R$^3$)$_m$; wherein (R$^3$)$_m$ represents one, or two optional substituents, wherein each R$^3$ independently is selected from the group consisting of (C$_{1-4}$)alkyl, (C$_{1-4}$)alkoxy, and halogen.
or a salt thereof.

10. A compound according to claim 1 selected from the group consisting of:
  5-m-Tolyl-oxazole-4-carboxylic acid {1-[2-(5-methoxy-1H-indol-3-yl)-ethyl]-1H-pyrazol-4-yl}-amide;
  5-m-Tolyl-oxazole-4-carboxylic acid {1-[2-(6-methoxy-indol-1-yl)-ethyl]-1H-pyrazol-4-yl}-amide;
  5-m-Tolyl-oxazole-4-carboxylic acid {1-[2-(6-methoxy-benzoimidazol-1-yl)-ethyl]-1H-pyrazol-4-yl}-amide;
  5-m-Tolyl-oxazole-4-carboxylic acid {1-[2-(6-methoxy-pyrrolo[2,3-b]pyridin-1-yl)-ethyl]-1H-pyrazol-4-yl}-amide;
  5-(3-Dimethylamino-phenyl)-oxazole-4-carboxylic acid {1-[2-(4,6-dimethoxy-pyrimidin-2-yloxy)-ethyl]-1H-pyrazol-4-yl}-amide;
  5-m-Tolyl-oxazole-4-carboxylic acid {1-[2-(4,6-dimethoxy-indol-1-yl)-ethyl]-1H-pyrazol-4-yl}-amide;
  5-m-Tolyl-oxazole-4-carboxylic acid {1-[2-(4,6-dimethoxy-pyrimidin-2-yloxy)-ethyl]-1H-pyrazol-4-yl}-amide;
  5-Phenyl-oxazole-4-carboxylic acid {1-[2-(4,6-dimethoxy-pyrimidin-2-yloxy)-ethyl]-1H-pyrazol-4-yl}-amide;
  5-m-Tolyl-oxazole-4-carboxylic acid {1-[2-(4,6-dimethoxy-pyrimidin-2-ylamino)-ethyl]-1H-pyrazol-4-yl}-amide;

5-m-Tolyl-oxazole-4-carboxylic acid [1-(2-benzoimidazol-1-yl-ethyl)-1H-pyrazol-4-yl]-amide;
5-m-Tolyl-oxazole-4-carboxylic acid {1-[2-(5,6-dimethoxy-indol-1-yl)-ethyl]-1H-pyrazol-4-yl}-amide;
5-(3-Fluoro-phenyl)-oxazole-4-carboxylic acid {1-[2-(4,6-dimethoxy-pyrimidin-2-yloxy)-ethyl]-1H-pyrazol-4-yl}-amide;
5-m-Tolyl-oxazole-4-carboxylic acid {1-[2-(2,4-dimethoxy-pyrrolo[2,3-d]pyrimidin-7-yl)-ethyl]-1H-pyrazol-4-yl}-amide;
5-m-Tolyl-oxazole-4-carboxylic acid {1-[2-(4,6-dimethoxy-pyrrolo[2,3-b]pyridin-1-yl)-ethyl]-1H-pyrazol-4-yl}-amide;
5-m-Tolyl-oxazole-4-carboxylic acid {1-[2-(6-fluoro-indol-1-yl)-ethyl]-1H-pyrazol-4-yl}-amide;
5-m-Tolyl-oxazole-4-carboxylic acid {1-[2-(4,6-dimethoxy-pyrimidin-2-ylamino)-ethyl]-1H-imidazol-4-yl}-amide;
5-m-Tolyl-oxazole-4-carboxylic acid {1-[2-(4-methoxy-pyrimidin-2-ylamino)-ethyl]-1H-pyrazol-4-yl}-amide;
5-m-Tolyl-oxazole-4-carboxylic acid {1-[2-(5-methoxy-pyrrolo[2,3-c]pyridin-1-yl)-ethyl]-1H-pyrazol-4-yl}-amide;
5-m-Tolyl-oxazole-4-carboxylic acid {1-[2-(6-methoxy-pyrrolo[3,2-c]pyridin-1-yl)-ethyl]-1H-pyrazol-4-yl}-amide;
5-m-Tolyl-oxazole-4-carboxylic acid {1-[2-(5,6-dichloro-indol-1-yl)-ethyl]-1H-pyrazol-4-yl}-amide;
5-m-Tolyl-oxazole-4-carboxylic acid {1-[2-(2-methyl-benzoimidazol-1-yl)-ethyl]-1H-pyrazol-4-yl}-amide;
5-m-Tolyl-oxazole-4-carboxylic acid {1-[2-(6-chloro-pyrrolo[2,3-b]pyridin-1-yl)-ethyl]-1H-pyrazol-4-yl}-amide;
5-m-Tolyl-oxazole-4-carboxylic acid {1-[2-(benzooxazol-2-ylsulfanyl)-ethyl]-1H-pyrazol-4-yl}-amide;
5-m-Tolyl-oxazole-4-carboxylic acid [1-(2-indol-1-yl-ethyl)-1H-pyrazol-4-yl]-amide;
5-m-Tolyl-oxazole-4-carboxylic acid {1-[3-(4,6-dimethoxy-pyrimidin-2-ylamino)-propyl]-1H-pyrazol-4-yl}-amide;
5-m-Tolyl-thiazole-4-carboxylic acid {1-[2-(quinoxalin-2-ylamino)-ethyl]-1H-pyrazol-4-yl}-amide;
5-m-Tolyl-oxazole-4-carboxylic acid {1-[2-(quinazolin-2-ylamino)-ethyl]-1H-pyrazol-4-yl}-amide;
5-m-Tolyl-oxazole-4-carboxylic acid [1-(2-pyrrolo[2,3-b]pyridin-1-yl-ethyl)-1H-pyrazol-4-yl]-amide;
5-m-Tolyl-oxazole-4-carboxylic acid {1-[2-(7-fluoro-indol-1-yl)-ethyl]-1H-pyrazol-4-yl}-amide;
5-(3-Morpholin-4-yl-phenyl)-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid {1-[2-(5-methyl-indol-1-yl)-ethyl]-1H-pyrazol-4-yl}-amide;
5-m-Tolyl-oxazole-4-carboxylic acid {1-[2-(quinazolin-2-yloxy)-ethyl]-1H-pyrazol-4-yl}-amide;
5-m-Tolyl-oxazole-4-carboxylic acid {1-[2-(benzooxazol-2-ylamino)-ethyl]-1H-pyrazol-4-yl}-amide;
5-m-Tolyl-thiazole-4-carboxylic acid {1-[2-(benzooxazol-2-ylamino)-ethyl]-1H-pyrazol-4-yl}-amide;
5-m-Tolyl-oxazole-4-carboxylic acid {1-[2-(4,6-dimethyl-pyrimidin-2-ylamino)-ethyl]-1H-pyrazol-4-yl}-amide;
5-m-Tolyl-oxazole-4-carboxylic acid {1-[2-(quinoxalin-2-ylamino)-ethyl]-1H-pyrazol-4-yl}-amide;
5-m-Tolyl-oxazole-4-carboxylic acid {1-[2-(quinazolin-2-ylamino)-ethyl]-1H-imidazol-4-yl}-amide;
5-m-Tolyl-oxazole-4-carboxylic acid {1-[2-(7-methyl-indol-1-yl)-ethyl]-1H-pyrazol-4-yl}-amide;
5-m-Tolyl-oxazole-4-carboxylic acid {1-[2-(3-methoxy-phenyl)-ethyl]-1H-pyrazol-4-yl}-amide;
5-m-Tolyl-oxazole-4-carboxylic acid {1-[2-(benzo[1,3]dioxol-5-yloxy)-ethyl]-1H-pyrazol-4-yl}-amide;
5-m-Tolyl-oxazole-4-carboxylic acid {1-[2-(5-fluoro-pyridin-2-ylamino)-ethyl]-1H-pyrazol-4-yl}-amide;
5-m-Tolyl-oxazole-4-carboxylic acid {1-[2-(4,6-dimethyl-pyridin-2-yloxy)-ethyl]-1H-pyrazol-4-yl}-amide;
5-m-Tolyl-oxazole-4-carboxylic acid {1-[2-(6-methoxy-purin-7-yl)-ethyl]-1H-pyrazol-4-yl}-amide;
5-m-Tolyl-oxazole-4-carboxylic acid {1-[2-(5-chloro-benzooxazol-2-ylamino)-ethyl]-1H-pyrazol-4-yl}-amide;
5-m-Tolyl-oxazole-4-carboxylic acid {1-[2-(3-methoxy-phenoxy)-ethyl]-1H-pyrazol-4-yl}-amide;
5-m-Tolyl-oxazole-4-carboxylic acid {1-[2-(4-methoxy-pyrrolo[2,3-b]pyridin-1-yl)-ethyl]-1H-pyrazol-4-yl}-amide;
5-Phenyl-oxazole-4-carboxylic acid {1-[2-(2-methyl-benzoimidazol-1-yl)-ethyl]-1H-pyrazol-4-yl}-amide;
5-(4-Trifluoromethyl-phenyl)-oxazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[2-(5-chloro-indol-1-yl)-ethyl]-1H-pyrazol-4-yl}-amide;
5-m-Tolyl-oxazole-4-carboxylic acid {1-[3-(2,3-dihydro-indol-1-yl)-propyl]-1H-pyrazol-4-yl}-amide;
5-m-Tolyl-oxazole-4-carboxylic acid {1-[2-(5,6-dimethoxy-indol-1-yl)-ethyl]-3,5-dimethyl-1H-pyrazol-4-yl}-amide;
5-m-Tolyl-oxazole-4-carboxylic acid [1-(3-indol-1-yl-propyl)-1H-pyrazol-4-yl]-amide;
5-(2-Fluoro-phenyl)-oxazole-4-carboxylic acid {1-[2-(5,6-dimethoxy-indol-1-yl)-ethyl]-1H-pyrazol-4-yl}-amide;
5-m-Tolyl-oxazole-4-carboxylic acid {1-[2-(4-fluoro-pyridin-2-ylamino)-ethyl]-1H-pyrazol-4-yl}-amide;
5-m-Tolyl-oxazole-4-carboxylic acid {1-[2-(2,3-dihydro-indol-1-yl)-ethyl]-1H-pyrazol-4-yl}-amide;
5-m-Tolyl-oxazole-4-carboxylic acid {1-[(R)-2-(4,6-dimethoxy-pyrimidin-2-ylamino)-propyl]-1H-pyrazol-4-yl}-amide;
5-(3-Cyano-phenyl)-oxazole-4-carboxylic acid {1-[2-(4,6-dimethoxy-pyrimidin-2-ylamino)-ethyl]-1H-pyrazol-4-yl}-amide;
5-Phenyl-oxazole-4-carboxylic acid {1-[2-(5,6-dimethoxy-indol-1-yl)-ethyl]-1H-pyrazol-4-yl}-amide;
rac-5-m-Tolyl-oxazole-4-carboxylic acid {1-[1-(4,6-dimethoxy-pyrimidin-2-yl)-pyrrolidin-2-ylmethyl]-1H-pyrazol-4-yl}-amide;
5-m-Tolyl-oxazole-4-carboxylic acid [1-(2-pyrrolo[3,2-b]pyridin-1-yl-ethyl)-1H-pyrazol-4-yl]-amide;
5-m-Tolyl-oxazole-4-carboxylic acid {1-[(S)-2-(4,6-dimethoxy-pyrimidin-2-ylamino)-propyl]-1H-pyrazol-4-yl}-amide;
5-m-Tolyl-oxazole-4-carboxylic acid {1-[2-(1-methyl-1H-indol-3-yl)-ethyl]-1H-pyrazol-4-yl}-amide;
5-m-Tolyl-oxazole-4-carboxylic acid {1-[2-(4-methoxy-pyridin-2-ylamino)-ethyl]-1H-pyrazol-4-yl}-amide;
5-(3,4-Dimethyl-phenyl)-thiazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[3-(6-methoxy-2,3-dihydro-indol-1-yl)-propyl]-1H-pyrazol-4-yl}-amide;

5-(6-Methoxy-pyridin-3-yl)-thiazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[2-(6-methoxy-pyrrolo[3,2-c]pyridin-1-yl)-ethyl]-3,5-dimethyl-1H-pyrazol-4-yl}-amide;
5-(3-Methoxy-4-methyl-phenyl)-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid {1-[2-(1H-indol-3-yl)-ethyl]-1H-pyrazol-4-yl}-amide;
5-(4-Methoxy-phenyl)-oxazole-4-carboxylic acid {1-[2-(5,6-dimethoxy-indol-1-yl)-ethyl]-1H-pyrazol-4-yl}-amide;
5-(3-Pyrrolidin-1-yl-phenyl)-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid [1-(2-indol-1-yl-ethyl)-3,5-dimethyl-1H-pyrazol-4-yl]-amide;
5-m-Tolyl-oxazole-4-carboxylic acid {1-[2-(4,6-dimethoxy-5-methyl-pyrimidin-2-ylamino)-ethyl]-1H-pyrazol-4-yl}-amide;
5-(3-Fluoro-phenyl)-oxazole-4-carboxylic acid {1-[2-(5,6-dimethoxy-indol-1-yl)-ethyl]-1H-pyrazol-4-yl}-amide;
5-(3-Methoxy-4-methyl-phenyl)-oxazole-4-carboxylic acid {1-[2-(5-methoxy-1H-indol-3-yl)-ethyl]-1H-pyrazol-4-yl}-amide;
5-Phenyl-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid {1-[2-(4-methoxy-1H-indol-3-yl)-ethyl]-1H-pyrazol-4-yl}-amide;
5-(3-Methoxy-4-methyl-phenyl)-oxazole-4-carboxylic acid {1-[2-(5,6-dimethoxy-indol-1-yl)-ethyl]-1H-pyrazol-4-yl}-amide;
5-(4-Methoxy-phenyl)-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid {1-[2-(5-fluoro-1H-indol-3-yl)-ethyl]-1H-pyrazol-4-yl}-amide;
5-m-Tolyl-oxazole-4-carboxylic acid {1-[3-(4-ethoxy-6-methoxy-pyrimidin-2-yl)-propyl]-1H-pyrazol-4-yl}-amide;
5-Biphenyl-3-yl-oxazole-4-carboxylic acid {1-[2-(5-methoxy-1H-indol-3-yl)-ethyl]-1H-pyrazol-4-yl}-amide;
5-Phenyl-thiazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[2-(5,6-dimethoxy-benzoimidazol-1-yl)-ethyl]-1H-pyrazol-4-yl}-amide;
5-Isoxazol-3-yl-oxazole-4-carboxylic acid {1-[2-(5-methoxy-1H-indol-3-yl)-ethyl]-1H-pyrazol-4-yl}-amide;
5-(3,4-Dimethyl-phenyl)-oxazole-4-carboxylic acid {1-[2-(5-methoxy-1H-indol-3-yl)-ethyl]-1H-pyrazol-4-yl}-amide;
5-(3,4-Dimethyl-phenyl)-oxazole-4-carboxylic acid {1-[2-(4,6-dimethoxy-pyrimidin-2-ylamino)-ethyl]-1H-pyrazol-4-yl}-amide;
5-m-Tolyl-oxazole-4-carboxylic acid {1-[3-(6-methoxy-indol-1-yl)-propyl]-1H-pyrazol-4-yl}-amide;
5-m-Tolyl-oxazole-4-carboxylic acid {1-[3-(4-methoxy-pyrimidin-2-ylamino)-propyl]-1H-pyrazol-4-yl}-amide;
5-m-Tolyl-oxazole-4-carboxylic acid {1-[2-(5-chloro-6-methoxy-indol-1-yl)-ethyl]-1H-pyrazol-4-yl}-amide;
5-(4-Methoxy-phenyl)-oxazole-4-carboxylic acid {1-[2-(5-methoxy-1H-indol-3-yl)-ethyl]-1H-pyrazol-4-yl}-amide;
5-m-Tolyl-thiazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[2-(2,6-dimethoxy-pyrimidin-4-ylamino)-ethyl]-1H-pyrazol-4-yl}-amide;
5-m-Tolyl-oxazole-4-carboxylic acid {1-[3-(4,6-dimethoxy-pyrimidin-2-yl)-propyl]-1H-pyrazol-4-yl}-amide;
5-m-Tolyl-oxazole-4-carboxylic acid {1-[2-(5-methoxy-1H-indol-3-yl)-ethyl]-1H-imidazol-4-yl}-amide;
5-(3-Fluoro-phenyl)-oxazole-4-carboxylic acid {1-[2-(4,6-dimethoxy-pyrimidin-2-ylamino)-ethyl]-1H-pyrazol-4-yl}-amide;
5-(3,4-Dimethyl-phenyl)-oxazole-4-carboxylic acid {1-[2-(5,6-dimethoxy-indol-1-yl)-ethyl]-1H-pyrazol-4-yl}-amide;
5-m-Tolyl-oxazole-4-carboxylic acid {1-[2-(5-methoxy-1-methyl-1H-indol-3-yl)-ethyl]-1H-pyrazol-4-yl}-amide;
5-(3-Chloro-phenyl)-thiazole-4-carboxylic acid {1-[2-(5-methoxy-1H-indol-3-yl)-ethyl]-1H-pyrazol-4-yl}-amide;
5-(3-Methyl-isoxazol-5-yl)-oxazole-4-carboxylic acid {1-[2-(5-methoxy-1H-indol-3-yl)-ethyl]-1H-pyrazol-4-yl}-amide;
5-(3-Trifluoromethyl-phenyl)-oxazole-4-carboxylic acid {1-[2-(5-methoxy-1H-indol-3-yl)-ethyl]-1H-pyrazol-4-yl}-amide;
5-m-Tolyl-oxazole-4-carboxylic acid {1-[2-(5-methoxy-1H-pyrrolo[3,2-b]pyridin-3-yl)-ethyl]-1H-pyrazol-4-yl}-amide;
5-(3-Trifluoromethoxy-phenyl)-oxazole-4-carboxylic acid {1-[2-(5-methoxy-1H-indol-3-yl)-ethyl]-1H-pyrazol-4-yl}-amide;
5-(2-Fluoro-phenyl)-oxazole-4-carboxylic acid {1-[2-(5-methoxy-1H-indol-3-yl)-ethyl]-1H-pyrazol-4-yl}-amide;
5-(3-Fluoro-phenyl)-oxazole-4-carboxylic acid {1-[2-(5-methoxy-1H-indol-3-yl)-ethyl]-1H-pyrazol-4-yl}-amide;
5-(3-Chloro-phenyl)-oxazole-4-carboxylic acid {1-[2-(5-methoxy-1H-indol-3-yl)-ethyl]-1H-pyrazol-4-yl}-amide; and
5-Phenyl-oxazole-4-carboxylic acid {1-[2-(5-methoxy-1H-indol-3-yl)-ethyl]-1H-pyrazol-4-yl}-amide;

or a salt thereof.

11. A pharmaceutical composition comprising, as active principle, one or more compounds according to claim 1, or a pharmaceutically acceptable salt thereof, and at least one pharmaceutically acceptable carrier.

12. A method for the or treatment of an insomnia, post-traumatic stress disorder (PTSD), or cognitive dysfunction in learning and/or memory, comprising administering to a patient in need thereof an effective amount of a compound according to claim 1, in free form or a pharmaceutically acceptable salt thereof.

* * * * *

UNITED STATES PATENT AND TRADEMARK OFFICE
CERTIFICATE OF CORRECTION

PATENT NO.         : 9,303,023 B2
APPLICATION NO.    : 14/000172
DATED              : April 5, 2016
INVENTOR(S)        : Bolli et al.

Page 1 of 1

It is certified that error appears in the above-identified patent and that said Letters Patent is hereby corrected as shown below:

Claims

Column 77, line 66, claim 9, --(a)-- should be inserted before "L represents."

Column 78, line 16, claim 9, --(b)-- should be inserted before "L represents."

Column 78, line 27, claim 9, --(c)-- should be inserted before "L represents."

Column 82, line 59, claim 12, "or" should be deleted.

Signed and Sealed this
Nineteenth Day of July, 2016

Michelle K. Lee
*Director of the United States Patent and Trademark Office*